(12) United States Patent
Kochanek et al.

(10) Patent No.: US 9,534,233 B2
(45) Date of Patent: Jan. 3, 2017

(54) NUCLEIC ACID CONSTRUCT AND USE OF THE SAME

(71) Applicant: Stefan Kochanek, Ulm (DE)

(72) Inventors: Stefan Kochanek, Ulm (DE); Tanja Lucas, Regensburg (DE); Claudia Kueppers, Weil am Rhein (DE)

(73) Assignee: Stefan Kochanek, Ulm (DE)

( * ) Notice: Subject to any disclaimer, the term of this patent is extended or adjusted under 35 U.S.C. 154(b) by 0 days.

(21) Appl. No.: 14/395,589

(22) PCT Filed: May 7, 2013

(86) PCT No.: PCT/EP2013/001356
§ 371 (c)(1),
(2) Date: Oct. 20, 2014

(87) PCT Pub. No.: WO2013/167265
PCT Pub. Date: Nov. 14, 2013

(65) Prior Publication Data
US 2015/0087021 A1    Mar. 26, 2015

Related U.S. Application Data

(60) Provisional application No. 61/645,154, filed on May 10, 2012.

(30) Foreign Application Priority Data

May 7, 2012  (EP) .................................... 12003564

(51) Int. Cl.
*C12N 15/85*    (2006.01)
*C12N 15/861*   (2006.01)
*C12N 15/86*    (2006.01)

(52) U.S. Cl.
CPC ............... *C12N 15/85* (2013.01); *C12N 15/86* (2013.01); *C12N 15/861* (2013.01); *C12N 2710/10343* (2013.01); *C12N 2840/44* (2013.01); *C12N 2840/85* (2013.01)

(58) Field of Classification Search
None
See application file for complete search history.

(56) References Cited

U.S. PATENT DOCUMENTS

| 6,558,948 B1 * | 5/2003 | Kochanek | ............ | C12N 5/0605 424/233.1 |
| 2007/0110719 A1 * | 5/2007 | Holm | .................... | C12N 15/86 424/93.2 |

FOREIGN PATENT DOCUMENTS

WO    0136615 A2    5/2001

OTHER PUBLICATIONS

Ben-Porath et al. "The Signals and Pathways Activating Cellular Senescence", The International Journal of Biochemistry & Cell Biology 37(5), pp. 961-976, (2005).
Baron et al. "Tetracycline-Controlled Transcription in Eukaryotes: Novel Transactivators with Graded Transactivation Potential", Nucleic Acids Research, vol. 25, No. 14, pp. 2723-2729, Jul. 15, 1997.
Bangari et al. "Development of Nonhuman Adenoviruses as Vaccine Vectors", NIH Public Access, Vaccine, 24(7): pp. 849-862, Feb. 13, 2006.
Adra et al. "Cloning and Expression of the Mouse pgk-1 Gene and the Nucleotide Sequence of its Promoter", Gene 60, pp. 65-74, (1987).
Whittaker JL et al. "Isolation and characterization of four adenovirus type 12-transformed human embryo kidney cell lines". Mol Cell Biol. Jan. 1984;4(1):110-6.
Graham FL et al. "Characteristics of a human cell line transformed by DNA from human adenovirus type 5". J Gen Virol 1977;36(1):59-74.
Hoehn H et al. "Cultivated cells from diagnostic amniocentesis in second trimester pregnancies. I. Clonal morphology and growth potential". Pediatr Res. Aug. 1974;8(8):746-54.
Schiedner et al. "Efficient and Reproducible Generation of High-Expressing, Stable Human Cell Lines Without Need for Antibiotic Selection", BMC Biotechnology, vol. 8, No. 1, Feb. 12, 2008, XP021035682. Cited in specification and International Search Report in PCT/EP2013/001356, dated Aug. 30, 2013.
Schiedner et al. "Efficient Transformation of Primary Human Amniocytes by E1 Function of AD5: Generation of New Cell Lines for Adenoviral Vector Production", Human Gene Therapy, Mary Ann Liebert, Inc., vol. 11, No. 15, Oct. 10, 2000, XP000974022. Cited in specification and International Search Report in PCT/EP2013/001356, dated Aug. 30, 2013.
Fallaux et al. "New Helper Cells and Matched Early Region 1-Deleted Adenovirus Vectors Prevent Generation of Replication-Competent Adenoviruses", Human Gene Therapy, vol. 9, Sep. 1, 1998, XP002943497. Cited in specification and International Search Report in PCT/EP2013/001356, dated Aug. 30, 2013.
Fairbrother et al. "Predictive Identification of Exonic Splicing Enhancers in Human Genes", Science, vol. 297, 2002, pp. 1007-1013, XP008110822. Cited in specification and International Search Report in PCT/EP2013/001356, dated Aug. 30, 2013.
International Search Report issued in PCT/EP2013/001356, dated Aug. 30, 2013. Form PCTISA220_210.
Written Opinion issued in PCT/EP2013/001356, dated Aug. 30, 2013. Form PCTISA237.
Zheng "Regulation of alternative RNA splicing by exon definition and exon sequences in viral and mammalian gene expression", Journal of Biomedical Science, vol. 11, No. 3, May 2004, pp. 278-294, XP009164194. Cited in International Search Report in PCT/EP2013/001356, dated Aug. 30, 2013.

(Continued)

*Primary Examiner* — Addison D Ault
(74) *Attorney, Agent, or Firm* — Rossi, Kimms & McDowell LLP

(57) ABSTRACT

The present invention is related to a nucleic acid construct comprising
an expression unit for the expression of E1B, wherein the expression unit comprises a promoter, a nucleotide sequence coding for E1B, and a 3'UTR, wherein the promoter is operatively linked to the nucleotide sequence coding for E1B, wherein the 3'UTR comprises 30 or less than 30 Exonic Enhancer Elements (ESEs), preferably 20 or less than 20 Exonic Enhancer Elements (ESEs), and wherein the 3' UTR is a non-viral 3' UTR.

12 Claims, 6 Drawing Sheets

(56) References Cited

OTHER PUBLICATIONS

International Preliminary Report on Patentability issued in PCT/EP2013/001356, dated Nov. 11, 2014. Form PCT/IB/313.
Wurm et al. "Inducible Overproduction of the Mouse c-myc Protein in Mammalian Cells", Proc. Natl. Acad. Sci. USA, vol. 83, pp. 5414-5418, Aug. 1986.
Vogels et al. "Replication-Deficient Human Adenovirus Type 35 Vectors for Gene Transfer and Vaccination: Efficient Human Cell Infection and Bypass of Preexisting Adenovirus Immunity", Journal of Virology, vol. 77, No. 15, p. 8263-8271, Aug. 2003.
Umana et al. "Efficient FLPe Recombinase Enables Scalable Production of Helper-Dependent Adenoviral Vectors with Negligible Helper-Virus Contamination", Nature Biotechnology, vol. 19(6), 582-5, Jun. 2001.
Toussaint et al. "Cellular and Molecular Mechanisms of Stress-Induced Premature Senescense (SIPS) of Human Diploid Fibroblasts and Melanocytes", Experimental Gerontology; 35(8):927-45; Oct. 2000.
Singer-Sam et al. "Sequence of the Promoter Region of the Gene for Human X-linked 3-Phosphoglycerate Kinase", Gene, 32 pp. 409-417, (1984).
Silva et al. "Adenovirus Vector Production and Purification", Current Gene Therapy, 10, pp. 437-455, Dec. 2010.
Sieber et al. "Adenovirus Type 5 Early Region 1B 156R Protein Promotes Cell Transformation Independently of Repression of p53-Stimulated Transcription", Journal of Virology, vol. 81, No. 1, pp. 95-105, Jan. 2007.
Schreiner et al. "Adenovirus Type 5 Early Region 1B 55K Oncoprotein-Dependent Degradation of Cellular Factor Daxx is Required for Efficient Transformation of Primary Rodent Cells", Journal of Virology, vol. 85, No. 17, pp. 8752-8765, Sep. 2011.
Berk "Recent Lessons in Gene Expression, Cell Cycle Control, and Cell Biology from Adenovirus", Oncogene 24(52), pp. 7673-7685, Nov. 21, 2005.
Blackfor et al. "Adenovirus E1B 55-Kilodalton Protein: Multiple Roles in Viral Infection and Cell Transformation", Journal of Virology, vol. 83, No. 9, pp. 4000-4012, May 2009.
Sarnow et al. "A Monoclonal Antibody Detecting the Adenovirus Type 5 E 1b-58Kd Tumor Antigen: Characterization of the E 1b-58Kd Tumor Antigen in Adenovirus-Infected and -Transformed Cells", Virology; 120, pp. 510-517 (1982).
Proudfoot "Ending the Message: Poly(A) Signals Then and Now", Genes & Development; 25: pp. 1770-1782, (2011).
Pesole et al. "Structural and Functional Features of Eukaryotic mRNA Untranslated Regions", Gene; 276, pp. 73-81, (2001).
Parks et al. "A Helper-Dependent Adenovirus Vector System: Removal of Helper Virus by Cre-Mediated Excision of the Viral Packaging Signal", Proc. Natl. Acad. Sci. USA, vol. 93(24), pp. 13565-13570, Nov. 1996.
No et al. "Ecdysone-Inducible Gene Expression in Mammalian Cells and Transgenic Mice" Proc. Natl. Acad. Sci. USA, vol. 93, pp. 3346-3351, Apr. 1996.
Murakami et al. "A Single Short Stretch of Homology Between Aenoviral Vector and Packaging Cell Line Can Give Rise to Cytopathic Effect-Inducing, Helper-Dependent E1-Positive Particles", Human Gene Therapy 13: pp. 909-920, May 20, 2002.
Murakami et al. "Common Structure of Rare Replication-Deficient E1-Positive Particles in Adenoviral Vector Batches", Journal of Virology, vol. 78, No. 12, pp. 6200-6208, Jun. 2004.
McConnell et al. "Biology of Adenovirus and Its Use as a Vector for Gene Therapy", Human Gene Therapy 15(11), pp. 1022-1033, Nov. 2004.
Louis et al. "Cloning and Sequencing of the Cellular-Viral Junctions from the Human Adenovirus Type 5 Transformed 293 Cell Line", Virology 233(2), pp. 423-429, (1997).
Loew et al. "Improved Tet-Responsive Promoters with Minimized Background Expression", BMC Biotechnology, 10:81, Nov. 24, 2010.
Lochmuller et al. "Emergence of Early Region 1-Containing Replication-Competent Adenovirus in Stocks of Replication-Defective Adenovirus Recombinants (delta E1 + delta E3) During Multiple Passages in 293 Cells", Human Gene Therapy 5(12), pp. 1485-1491, Dec. 1994.
Kim et al. "The ASAP II Database: Analysis and Comparative Genomics of Alternative Splicing in 15 Animal Species", Nucleic Acids Research, vol. 35 Database issue D93-D98, (2007).
Imperiale et al. "Adenovirus Vectors: Biology, Design, and Production", Curr Top Microbiol Immunol, 27, pp. 335-358, 2004.
Hynes et al. "Mammary Tumor Formation and Hormonal Control of Mouse Mammary Tumor Virus Expression", Curr Top Microbiol Immunol, 101, pp. 51-74, 1982.
Hu et al. "The Inducible lac Operator-Repressor System is Functional in Mammalian Cells", Cell, vol. 48, pp. 555-566, Feb. 27, 1987.
Hehir et al. "Molecular Characterization of Replication-Competent Variants of Adenovirus Vectors and Genome Modifications to Prevent Their Occurrence", Journal of Virology, 70(12), pp. 8459-8467, Dec. 1996.
Harley et al. "Telomeres Shorten During Ageing of Human Fibroblasts", Nature, vol. 345(6274), pp. 458-460, May 31, 1990.
Gao et al. "Human Adenovirus Type 35: Nucleotide Sequence and Vector Development", Gene Therapy, 10(23), pp. 1941-1949, Nov. 2003.
Gallimore et al. "Transformation of Human Embryo Retinoblasts with Simian Virus 40, Adenovirus and ras Oncogenes", Anticancer Research, 6(3 PtB), pp. 499-508, (1986).
Boshart et al. "A Very Strong Enhancer is Located Upstream of an Immediate Early Gene of Human Cytomegalovirus", Cell, vol. 41, pp. 521-530, Jun. 1985.
Fallaux et al. "Characterization of 911: A New Helper Cell Line for the Titration and Propagation of Early Region 1-Deleted Adenoviral Vectors", Human Gene Therapy, 7(2), pp. 215-222, Jan. 20, 1996.
Fairbrother et al. "Rescue-ESE Identifies Candidate Exonic Splicing Enhancers in Vertebrate Exons", Nucleic Acids Research, vol. 32, Web Server issue W187-W190, (2004).
Burcin et al. "A Regulatory System for Target Gene Expression", Frontiers in Bioscience, 3, c1-7, Mar. 1, 1998.
Endter et al. "SUMO-1 Modification Required for Transformation by Adenovirus Type 5 Early Region 1B 55-kDa Oncoprotein", Proc Natl Acad Sci USA, vol. 98, No. 20, pp. 11312-11317, Sep. 25, 2001.
Dorsch-Hasler et al. "A Long and Complex Enhancer Activates Transcription of the Gene Coding for the Highly Abundant Immediate Early mRNA in Murine Cytomegalovirus", Proc. Natl. Acad. Sci. USA, vol. 82, pp. 8325-8329, Dec. 1985.
Davies et al. "A New Selective Agent for Eukaryotic Cloning Vectors", Am. J. Trop. Med. Hyg., 29(5) Suppl., pp. 1089-1092, (1980).
Byrd et al. "Malignant Transformation of Human Embryo Retinoblasts by Cloned Adenovirus 12 DNA", Nature, vol. 298, pp. 69-71, Jul. 1982.
Burset et al. "SpliceDB: Database of Canonical and Non-Canonical Mammalian Splice Sites", Nucleic Acids Research, vol. 29, No. 1., pp. 255-259, (2001).
Office Action issued in Israeli Appln. No. 235426 mailed Nov. 26, 2015. English translation provided.
Goverdhana et al. "Regulatable Gene Expression Systems for Gene Therapy Applications: Progress and Future challenges." Molecular Therapy. Aug. 2005: 189-211. vol. 12, No. 2. Cited in NPL 1.

* cited by examiner

NUCLEIC ACID CONSTRUCT AND USE OF THE SAME

The instant application contains a Sequence Listing which has been submitted in ASCII format via EFS-Web and is hereby incorporated by reference in its entirety. Said ASCII copy, created on Oct. 16, 2014,is named BOHM-0002A_ELECTRONIC_SEQ_LISTING.txt and is 82150 bytes in size.

A. BACKGROUND OF THE INVENTION

The present invention is related to a nucleic acid construct comprising an expression unit for the expression of E1A and an expression unit for the expression of E1B, a vector comprising such nucleic acid construct, a cell comprising the nucleic acid construct and/or the vector, a method for the production of a permanent amniocytic cell line comprising the step of introducing the nucleic acid construct and/or the vector, a permanent amniocyic cell line, the use of the cell, a method for the production of a gene transfer vector or an adenovirus mutant, and a method for the production of a protein.

1. Adenovirus and Adenovirus Infectious Cycle

Adenoviruses are non-enveloped viruses belonging to the virus family Adenoviridae. They carry a linear double-stranded DNA genome with a size of about 36 kilobases (kb). The viral genome contains at both ends the inverted terminal repeat sequences (ITRs) as origin of replication and at the left end a packaging signal. Adenoviruses have been isolated from many vertebrate species including humans and chimpanzees. More than 50 human serotypes can be distinguished based on DNA sequence. During an infectious cycle the viral particle enters the cell by receptor-mediated endocytosis and the viral genome enters the nucleus as DNA-protein complex. The adenoviral infection cycle is divided into an early and a late phase, which are separated by the start of adenoviral replication (Shenk, in: Virology, Fields ed., Lippincott-Raven Publishing, Philadelphia, pp. 2111-2148, 1996). In the early phase, i.e. before replication, there is expression of the early viral functions E1, E2, E3 and E4. The late phase is characterized by transcription of late genes, which are responsible for the expression of viral structural proteins and for the production of new viral particles.

E1A is the first viral gene expressed after the viral genome enters the nucleus. The E1A gene codes for the 12S and 13S proteins, which are formed by alternative splicing of the E1A RNA. By binding to several cellular proteins including pRB, p107, p130, p300 (CBP), p400, TRAP and others (Berk, 2005), the E1A proteins activate cellular DNA synthesis, promote S-phase entry, activate and repress, respectively, a large number of cellular genes, thereby instructing the cell to allow a viral infectious cycle. In addition, E1A activates most other adenovirus genes including E1B, E2, E3, E4 and the major late transcription unit (MLTU). Expression of E1A on its own leads to apoptosis.

E1B is one of the early viral genes activated by E1A. The E1B gene codes for several proteins, including the well-known E1B 55 kD and E1B 19 kD proteins, which are generated by alternative splicing of the E1B RNA. The E1B 55 kD (also called E1B 55K) protein modulates the progression of the cell cycle by interacting with the p53 tumor suppressor, is involved in preventing the transport of cellular mRNA in the late phase of the infection, and prevents E1A-induced apoptosis of cells. The E1B 19 kD (also called E1B 19K) protein is likewise important for preventing E1A-induced apoptosis of cells.

Rodent cells can be easily transformed in cell culture by expression of the E1A and E1B proteins and in rodent cells co-expression of the E1A and E1B proteins is considered to be necessary and sufficient for the transformation event to occur. In addition to transcripts coding for the E1B 55K and 19K proteins, three further E1B transcripts, also generated by alternative splicing have been identified (E1B-156R, E1B-93R and E1B-84R), one of which (E1B-156R) has been shown to promote transformation (Sieber et al. 2007). In the context of the wildtype adenoviral genome, all E1B transcripts use a common downstream splice acceptor that overlaps with part of the 5'-untranslated transcript of the pIX gene (i.e. between the pIX promoter and the translational start of pIX). In hAd5 (NCBI Reference Sequence: AC_000008) this splice acceptor is located at nucleotide 3595 of the hAd5 genomic sequence.

The next genes to be expressed during an infectious cycle are the E2A and E2B genes coding for three proteins (preterminal protein, pTP; DNA Polymerase, Pol; and DNA-binding protein, DBP), all involved in replication of the viral genome.

E3 is mainly involved in counteracting host defenses against adenoviral infection and is dispensable for virus grows in cell culture.

E4, also expressed early in an infectious cycle, codes for various proteins. In addition to other functions E4 blocks, together with the E1B 55K protein, the accumulation of cellular mRNAs in the cytoplasm, and at the same time it facilitates the transport of viral RNAs from the cell nucleus into the cytoplasm.

The initiation of DNA replication is followed by expression of structural proteins, which are necessary for the formation of the viral capsid and for condensation of the viral DNA. Late during an infectious cycle the viral DNA is packaged into the viral capsid. The exact mechanism of the packaging of the viral genome into the viral capsid is currently unknown, but involves interaction of several virus-encoded proteins with the packaging signal located at the left terminus of the viral genome.

2. Adenovirus Vectors

Different vector types based on adenovirus have been developed (McConnell et al. 2004; Imperiale et al. 2004).

Adenoviral vectors usually have at least deletions of the E1A and E1B genes and are therefore replication-deficient in human cells. Production takes place in human complementing cell lines, which express the E1A and E1B proteins and in which the E1A and E1B genes are chromosomally integrated.

The ΔE1Ad vector (also called E1-deleted Ad vector or first-generation Ad vector) is the dominant vector type, which is widely used as laboratory tool, in pre-clinical R&D, in clinical studies and product development in the context of gene therapy or genetic vaccination. This vector type is made replication-defective in primary cells by removal of the E1 region (ΔE1) encoding the E1A and E1B proteins.

Many ΔE1Ad vectors also contain partial or complete deletion of the E3 region (ΔE1/ΔE3 Ad vectors), since E3, among other functions modulating virus-host interaction and interfering with the immune system, is dispensable for vector production in cell culture. So far, most ΔE1Ad vectors are based on human adenovirus type 5 (hAd5). However, vectors based on other human (e.g. hAd6, hAd26, hAd35 and others) and non-human adenovirus types (e.g. derived from Chimpanzee) have been developed (Bangari et al. Vacci 2006).

Second-generation vectors are based on ΔE1Ad vectors that carry additional mutations in other early regions of the viral genome, including the E2 genes and/or the E4 genes (Imperiale et al. Curr Top Microbiol Immunol 2004, 273, 335-57). They are produced in cell lines, in which, in addition to the E1A and E1B genes, also the respective adenoviral gene or genes that is/are mutated in the vector's genome are expressed. For example, Ad vectors with deletion of the DNA binding protein (DBP) that is one of the E2 genes are produced in cell lines, which express the DBP in addition to the E1A and E1B genes.

In high-capacity Ad (HC-Ad) vectors (also called helper-dependent Ad vectors) all viral coding sequences are replaced by the transgene(s) of interest. In most cases additional stuffer DNA are included in the vector to prevent rearrangements during production. Current production systems are based on the use of a replication-deficient (ΔE1) helper virus providing all non-structural and structural viral functions in trans together with a production cell line expressing either Cre or Flp recombinase (Parks et al., 1996; Umana et al., 2001).

Production and purification methods of Ad vectors in adherent or in suspension cell culture are well known to the expert and have been described (Silva et al., 2010).

3. Generation of Producer Cell Lines by Transformation of Human Cells with the E1A and E1B Genes Traditionally, ΔE1Ad vectors have mainly been produced in 293 cells, which were generated by transfection of human embryonic kidney (HEK) cells with sheared DNA of human Adenovirus type 5 (Graham et al., 1977). In a total of eight transfection experiments, with an average of twenty HEK cultures used per experiment, only a single immortalized cell clone was obtained (Graham et al., 1977). HEK 293, the cell line established from this cell clone, contains chromosomally integrated nucleotides (nt.) 1 to 4344 of the Ad5 genome, including the E1A and E1B genes, left ITR and the adenoviral packaging signal (Louis et al., 1997).

Although rodent cells can easily be transformed with adenoviral E1 functions, primary human cells have been found to be notoriously difficult to transform with the E1A and E1B genes. Gallimore and coworkers attempted to transform primary HEK cells with E1 functions of Ad12 (Gallimore et al., 1986). These experiments were carried out unsuccessfully over a period of three years with more than 1 mg of the EcoRI cDNA fragment of Ad12, containing the E1A and E1B genes. Despite a large number of experiments carried out, only four Ad12-E1 HEK cell lines were isolated (Whittaker et al., 1984). Likewise, the same group failed to transform other primary human cells with E1 functions, including keratinocytes, skin fibroblasts, hepatocytes and urothelial cells (Gallimore et al., 1986). One cell type reproducibly transformed with adenoviral E1 functions are human embryonic retinal cells (HER cells) (Byrd et al., Nature 298, 69-71, 1982). Although the transformation efficiency of HER cells was lower than that of primary rat cells, it was more than 100 times higher than that of HEK cells. The investigations were initiated in order to produce complementing cell lines for the isolation of Ad12 E1 mutants.

Transfection of HERs with a construct containing an hAd5 fragment from nt 79 to 5789 resulted in a cell line, named 911, which supported the growth of ΔE1Ad vectors and at least matched production yield of 293 cells (Fallaux et al., 1996). However, due to extensive overlap with ΔE1Ad vectors both 911 and 293 cells are prone to the regular generation of replication competent adenovirus (RCA) as a result of homologous recombination events between the vector genome and the chromosomally integrated E1 region during production (Lochmüller et al., 1994; Hehir et al., 1996). Importantly, this is a frequent occurrence that can neither be controlled nor avoided in particular during serial passage of vectors and large-scale vector production. The U.S. Food and Drug Administration (FDA) guidelines demand the presence of less than one RCA in $3 \times 10^{10}$ vector particles for clinical applications (Biological Response Modifiers Advisory Committee, 2001).

To circumvent and/or prevent the risk of RCA emergence during Ad vector production, other E1-transcomplementing cell lines harbouring a minimized E1 DNA fragment lacking any homology with the DNA of commonly used Ad vectors have been developed. In particular, HER cells were transformed with a new E1A and E1B encoding construct, in which any identical sequences/sequence overlap with ΔE1Ad vectors were/was eliminated. By replacing the E1A promoter by the human phosphoglycerate kinase (PGK) promoter and the 3'-untranslated region (3'UTR) of E1B by the mRNA processing elements of the hepatitis B virus surface (HbS) antigen (not containing an intron), the E1-transformed cell line PER.C6 was generated solely encompassing hAd5 sequences from nt. 459 to 3510 (Fallaux et al., 1998). Accordingly, matching ΔE1Ad vectors lacking this region can be efficiently propagated in these cells without the occurrence of RCA due to homologous recombination. However, in two publications about PER.C6 cells unusual vector recombinants have been observed, that result in vector specimen carrying and expressing E1 functions. In the first report (Murakami et al., 2002), in which the vector did have an overlap of 177 nt. with the integrated E1 region, helper-dependent E1-positive particles (HDEPs) were generated caused by one homologous and one heterologous recombination event, resulting in the concomitant deletion of parts of the adenoviral vector backbone. As a result the Ad vector preparation contained two different particle species: the original ΔE1 vector and the E1 region-containing recombinant. In a second report (Murakami et al., 2004) E1 region-positive recombinant particles were described although the parental vector sequence did not overlap with the integrated E1 region. Detailed analysis of several different independent E1-positive isolates showed a similar structure of recombinants, consisting of a palindromic structure of several copies of the E1 region flanked by the adenoviral left ITR including the packaging signal. According to the authors' interpretation, the recombinants most likely were generated following heterologous recombination between the ΔE1Ad vector and the chromosomal DNA close to the E1-region. The authors further speculate, that the generation of the E1-positive recombinants is facilitated by the observed head-to-head dimer structure of (some of) the 10 to 20 E1 region integrates that are present in PER.C6 cells.

Some non-hAd5 based ΔE1Ad vectors, an example being vectors based on hAd35, cannot be propagated in regular production systems such as 293 cells or PER.C6 cells, since both express E1A and E1B of hAd5, while hAd35-based vectors require for their production E1B functions of hAd35. Thus, for production of such vectors, the missing function needs to be provided in the production cell line. In case of hAd35-based vectors, for example, an E1B function of hAd35 has to be provided by the cell line (Vogels et al., 2003, Gao et al., 2003).

More recently, human amniocytes were identified as an alternative cell source for the generation of cell lines following transformation with E1 functions (Schieder et al., 2000) and E1/pIX genes (Schieder et al., 2008). The design of the E1A and E1B expressing plasmid construct in the cell line N52.E6 (Schiedner et al., 2000), was similar as in PER.C6 cells, in principle excluding the generation of RCA during vector production due to the absence of any sequence overlap between vector DNA and the integrated E1 region.

There have been additional attempts to generate production cell lines for ΔE1 vectors. Unlike the cell lines discussed above, they all were based on established cell lines such as HeLa and A549 cells although, due to the poorly documented generation of the original cell lines, their tumorigenic origin and their high tumorigenicity, they are not suitable for production of clinical grade material (reviewed in Silva et al., 2010).

4. Immortalization of Primary Cells in Cell Culture

Mammalian cells, when isolated from an animal or a human, taken into a cell culture dish and provided with proper nutrients, can be cultured by serial passaging only for a limited time. This phenomenon has been first described by Hayflick (Hayflick and Moorhead, 1961) and is called cellular senescence. Senescent cells in cell culture undergo changes in their morphology and become large and flattened; they stop dividing while remaining metabolically active. There are distinct changes in gene expression, protein processing and metabolism and, as useful marker, cells stain positive for senescence-associated β-galactosidase (SA-β-gal) (Weinberg, R. A., The Biology of Cancer, 2007, Garland Science). The limitation in replicative potential of primary mammalian cells in cell culture and senescence is mainly associated both with cell-physiologic stress factors due to cell culture conditions (characterized by alteration in specific signaling pathways, such as frequent upregulation of p16/INK4a and others (Ben-Porath and Weinberg, 2005)) and with reduction of telomere length at the chromosomal ends due to the so-called endreplication problem that occurs during replication of cellular DNA (Weinberg, R. A., 2007 supra). Telomeres are structures located at the end of chromosomes, consisting of short hexanucleotide DNA repeats and being associated with a number of proteins, protecting the integrity of chromosomes and preventing, for example, fusion events between different chromosomes. Telomere length is maintained by the activity of several proteins including the essential telomerase holoenzyme that consists of the catalytic subunit hTERT and an RNA subunit (hTR). In primary cells, the activity of hTERT is too low to maintain telomere length constant, resulting in a gradual loss of telomeric repeats during replication of the cellular DNA. In humans, the number of replicative doublings a primary cell can maximally go through before entering senescence is ranging from about 50 to 60 population doublings (PD), slowly decreasing when cells are isolated from individuals with increasing age (Weinberg, R. A., 2007 supra). The number of PDs is also dependent on the specific cell type and the cell culture conditions. Some cells can be taken into cell culture only for a few PDs, other for a larger number, however not beyond far the limit mentioned above.

Cells, that can be maintained in cell culture indefinitely, when they are provided with appropriate nutrients, are said to be immortal and such cells can also be called a cell line or a permanent cell line. Primary normal human cells usually do not become immortalized spontaneously. However, immortalization can be achieved experimentally, for example by introducing cellular or viral oncogenes or by introducing mutations in tumour suppressor genes.

Crisis is a term that is mechanistically linked to the reduction of telomere length to a point that most cells will undergo cell death. This can be observed, for example, when tumour cells are taken into cell culture. After a certain number of replicative doublings, most of the cells will undergo cell death due to telomere length shortening. Only rarely individual cells will survive, generally selected for increased growth rate and survival by additional mutations. When primary human cells, for example human fibroblasts or epithelial cells are taken into cell culture, it is frequently observed that cells can be maintained by passaging for a small number of PDs until they acquire a senescent phenotype. This early type of senescence can be delayed, for example by the expression in these cells of the large T Antigen of SV40 (Weinberg, R. A., 2007 supra), resulting in the inactivation of the oncoproteins pRB and p53. However, after a certain number of PDs and depending on the length of the remaining telomeres the cells will enter crisis due to telomere collapse. Only cells, which manage to either activate telomerase or to engage an alternative way of telomere maintenance—called alternate lengthening of telomeres (ALT)—have a chance to survive. According to current understanding, crisis is the time, when structural abnormalities of the karyotype are preferentially established, due to fusion events between eroded (telomere depleted) chromosomal ends, followed by so-called breakage-fusion-bridge (BFB) cycles, resulting in karyotypic chaos (Weinberg, R. A., 2007 supra). These abnormalities, in combination with other mutations occurring during culture, furnish some cells with a selective growth advantage, enabling them to evade from crisis and become immortalized.

5. Use of Human Cells for the Production of Biologics

Human cells are of significant interest to the industry for the production of certain biologics such as viral vectors, proteins, viruses and vaccines for therapeutic, diagnostic or prophylactic human or veterinary use. Examples for viral vectors that can be used for therapeutic or prophylactic purposes are vectors that are based on different viruses including adenovirus, retrovirus, herpes simplex virus or parvovirus. Most of viral vectors used today are produced in human cell lines such as 293 cells. They can be used either for functional studies, for therapeutic purposes such as gene therapy or for therapeutic or prophylactic purposes such as genetic vaccination. Proteins that cannot be produced in simple organism such as bacteria or that are characterized by certain posttranslational modifications frequently require the use of mammalian cells for their production. Examples of biologics that can be produced in human cells are therapeutic or diagnostic antibodies or therapeutic glycoproteins including for example blood coagulation factors or fibrinolytic proteins. Many human vaccines are based on inactivated or attenuated human viruses that grow well on human cells. Also many subunit protein vaccines or complex vaccines such as virus-like-particles (VLPs) can be produced in human cells.

For production of biologics at an industrial scale, however, the use of permanent cell lines rather than of primary cells is a necessity. In general, primary cells can often not be expanded to a sufficient amount to allow production of proteins or viruses at a scale large enough for market supply. While permanent cell lines can be grown to a very large cell number, either as adherent cell culture or in suspension, it is well known, that genetic stability of cultured cells is difficult to maintain, for example due to telomere shortening during the process of immortalization or due to oxidative stress during cell culture resulting in mutations. However, genetic stability of cell lines is very important for the industrial production of well-characterized products of high quality (e.g. characterized by consistent glycosylation of glycoproteins), activity (e.g. characterized by consistent immunogenicity of vaccines) and uniformity (e.g. little variation of the product between different production runs).

Thus, the problem underlying the present invention is to provide means which allow the generation of a genetically stable cell line.

A further problem underlying the present invention is to provide a genetically stable cell line.

A still further problem underlying the present invention is to provide means which allow the practicing of a method for the improved generation of immortalized and genetically stable human cell lines which may, among others, be used in the production of therapeutic, diagnostic or prophylactic biologics for human or veterinary use.

B. SUMMARY OF THE INVENTION

These and other problems underlying the present invention are solved by the subject matter of the attached independent claims. Preferred embodiment may be taken from the attached dependent claims.

More specifically, the problem underlying the present invention is solved in a first aspect which is also the first embodiment of the first aspect, by a nucleic acid construct comprising an expression unit for the expression of E1B, wherein the expression unit comprises a promoter, a nucleotide sequence coding for E1B, and a 3'UTR and wherein the promoter is operatively linked to the nucleotide sequence coding for E1B, wherein the 3' UTR comprises 30 or less than 30 Exonic Enhancer Elements (ESEs).

In a second embodiment of the first aspect which is also an embodiment of the first embodiment of the first aspect, the nucleic acid construct comprises an expression unit for the expression of E1A, wherein the expression unit comprises a promoter, a nucleotide sequence coding for E1A, and a 3' UTR and wherein the promoter is operatively linked to the nucleotide sequence coding for E1A.

In a third embodiment of the first aspect which is also an embodiment of the first and the second embodiment of the first aspect, the nucleic acid construct is a one-piece nucleic acid molecule comprising both the expression unit for the expression of E1A and the expression unit for the expression of E1B.

In a fourth embodiment of the first aspect which is also an embodiment of the third embodiment of the first aspect, the expression unit for the expression of E1A and the expression unit for the expression of E1B are arranged within the one-piece nucleic acid molecule as follows:
5'-expression unit for the expression of E1A-expression unit for the expression of E1B-3'.

In a fifth embodiment of the first aspect which is also an embodiment of the first, the second, the third and the fourth embodiment of the first aspect, the nucleic acid construct is a two-piece nucleic acid molecule comprising a first nucleic acid molecule and a second nucleic acid molecule, wherein the first nucleic acid molecule comprises the expression unit for the expression of E1B and the second nucleic acid molecule comprises the expression unit for the expression of E1A.

In a sixth embodiment of the first aspect which is also an embodiment of the first, the second, the third, the fourth and the fifth embodiment of the first aspect, the 3' UTR of the expression unit for the expression of E1B comprises 20 or less than 20 Exonic Enhancer Elements (ESEs).

In a seventh embodiment of the first aspect which is also an embodiment of the first, the second, the third, the fourth, the fifth and the sixth embodiment of the first aspect, the 3'UTR of the expression unit for the expression of E1B comprises 5 or less than 5 Exonic Enhancer Elements (ESEs).

In an eighth embodiment of the first aspect which is also an embodiment of the first, the second, the third, the fourth, the fifth, the sixth and the seventh embodiment of the first aspect, the Exonic Enhancer Elements (ESEs) are contained within a stretch of nucleotides of the 3'UTR of the expression unit for the expression of E1B, whereby such stretch of nucleotides comprises the 200 nucleotides of the 5' end of the 3'UTR of the expression unit for the expression of E1B.

In a ninth embodiment of the first aspect which is also an embodiment of the first, the second, the third, the fourth, the fifth, the sixth, the seventh and the eighth embodiment of the first aspect, the expression unit for the expression of E1B comprises a splice donor site, an intron and a splice acceptor site.

In a tenth embodiment of the first aspect which is also an embodiment of the ninth embodiment of the first aspect, the splice donor site, the intron and the splice acceptor site are located in the expression unit for the expression of E1B between the nucleotide sequence coding for E1B and the 3'UTR.

In an eleventh embodiment of the first aspect which is also an embodiment of the ninth and the tenth embodiment of the first aspect, the intron comprising the splice donor site at the 5' end of the intron and the splice acceptor site at the 3' end of the intron is located downstream of the nucleotide sequence coding for E1B, preferably at the 3' end of the nucleotide sequence coding for E1B.

In a twelfth embodiment of the first aspect which is also an embodiment of the first, the second, the third, the fourth, the fifth, the sixth, the seventh, the eighth, the ninth, the tenth and the eleventh embodiment of the first aspect, the 3'UTR of the expression unit for the expression of E1B is different from a 3' UTR of Simian virus 40 (SV40).

In a 13$^{th}$ embodiment of the first aspect which is also an embodiment of the ninth, the tenth, the eleventh and the twelfth embodiment of the first aspect, the intron of the expression unit for the expression of E1B is different from an intron of Simian virus 40 (SV40).

In a 14$^{th}$ embodiment of the first aspect which is also an embodiment of the first, the second, the third, the fourth, the fifth, the sixth, the seventh, the eighth, the ninth, the tenth, the eleventh, the twelfth and the 13$^{th}$ embodiment of the first aspect, the 3' UTR of the expression unit for the expression of E1B is a non-viral 3' UTR, preferably a mammalian 3' UTR.

In a 15$^{th}$ embodiment of the first aspect which is also an embodiment of the ninth, the tenth, the eleventh, the twelfth, the 13$^{th}$ and the 14$^{th}$ embodiment of the first aspect, the intron is a constitutive intron.

In a 16$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$ and the 15$^{th}$ embodiment of the first aspect, the nucleic acid construct comprises a nucleotide sequence coding for protein E1B84R.

In a 17$^{th}$ embodiment of the first aspect which is also an embodiment of the 16$^{th}$ embodiment of the first aspect, protein E1B84R is expressed after transfer of the nucleic acid construct into a permissive cell.

In a 18$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$ and the 18$^{th}$ embodiment of the first aspect, the nucleic acid construct comprises a nucleotide sequence coding for pIX RNA or a part thereof.

In a 19$^{th}$ embodiment of the first aspect which is also an embodiment of the 18$^{th}$ embodiment of the first aspect, the nucleotide sequence coding for pIX RNA is not transcribed and/or not translated after transfer of the nucleic acid construct into a permissive cell.

In a 20$^{th}$ embodiment of the first aspect which is also an embodiment of the 18$^{th}$ and the 19$^{th}$ embodiment of the first aspect, the nucleotide sequence coding for the pIX RNA or part thereof is located at the 3' end of the nucleotide sequence coding for E1B or at the 3' end of the splice acceptor site, preferably so as to provide for a nucleotide sequence coding for the C-terminus of E1B84R.

In a 21$^{st}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$ and the 20$^{th}$ embodiment of the first aspect, the promoter of the expression unit for the expression of E1A is a constitutive promoter.

In a 22$^{nd}$ embodiment of the first aspect which is also an embodiment of the 21$^{st}$ embodiment of the first aspect, the promoter is a non-adenoviral promoter.

In a 23$^{rd}$ embodiment of the first aspect which is also an embodiment of the 21$^{st}$ and the 22$^{nd}$ embodiment of the first aspect, the promoter is selected form the group comprising human phosphoglycerate kinase (hPGK) promoter, murine phosphoglycerate kinase (hPGK) promoter, human Cytomegalovirus (hCMV) promoter and murine Cytomegalovirus (mCMV) promoter.

In a 24$^{th}$ embodiment of the first aspect which is also an embodiment of the 23$^{rd}$ embodiment of the first aspect, the promoter is the murine phosphoglycerate kinase (mPGK) promoter.

In a 25$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$ and the 20$^{th}$ embodiment of the first aspect, the promoter of the expression unit for the expression of E1A is an adenoviral promoter or an inducible promoter.

In a 26$^{th}$ embodiment of the first aspect which is also an embodiment of the 25$^{th}$ embodiment of the first aspect, the inducible promoter is selected from the group comprising metal ion-inducible promoters, IPTG-inducible promoters, steroid-inducible promoter, tetracycline-inducible promoters and mifepristone-inducible promoters.

In a 27$^{th}$ embodiment of the first aspect which is also an embodiment of the 26$^{th}$ embodiment of the first aspect, the inducible promoter is a tetracycline-inducible promoter.

In a 28$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$, the 23$^{rd}$, the 24$^{th}$, the 25$^{th}$, the 26$^{th}$ and the 27$^{th}$ embodiment of the first aspect, the nucleotide sequence coding for E1A codes for E1A12S and E1A13S.

In a 29$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$, the 23$^{rd}$, the 24$^{th}$, the 25$^{th}$, the 26$^{th}$, the 27$^{th}$ and the 28$^{th}$ embodiment of the first aspect, the nucleotide sequence coding for E1A comprises a nucleotide sequence according to SEQ ID NO: 2.

In a 30$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$ and the 23$^{rd}$ embodiment of the first aspect, the promoter of the expression unit for the expression of E1B is an adenoviral promoter, preferably the E1B promoter.

In a 31$^{st}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$, the 23$^{rd}$, the 24$^{th}$, the 25$^{th}$, the 26$^{th}$, the 27$^{th}$, the 28$^{th}$, the 29$^{th}$ and the 30$^{th}$ embodiment of the first aspect, the promoter of the expression unit for the expression of E1B is a constitutive promoter.

In a 32$^{nd}$ embodiment of the first aspect which is also an embodiment of the 31$^{5t}$ embodiment of the first aspect, the promoter is selected form the group comprising human phosphoglycerate kinase (hPGK) promoter, murine phosphoglycerate kinase (mPGK) promoter, human Cytomegalovirus (hCMV) promoter and murine Cytomegalovirus (mCMV) promoter.

In a 33$^{rd}$ embodiment of the first aspect which is also an embodiment of the 32$^{nd}$ embodiment of the first aspect, the promoter is the human phosphoglycerate kinase (hPGK) promoter.

In a 34$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$, the 23$^{rd}$, the 24$^{th}$, the 25$^{th}$, the 26$^{th}$, the 27$^{th}$, the 28$^{th}$, the 29$^{th}$, the 30$^{th}$, the 31$^{st}$, the 32$^{nd}$ and the 33$^{rd}$ embodiment of the first aspect, the nucleotide sequence coding for E1B codes for the protein E1B 55K and the protein E1B 19K.

In a 35$^{th}$ embodiment of the first aspect which is also an embodiment of the 34$^{th}$ embodiment of the first aspect, protein E1B 55K and protein E1B 19K are expressed after transfer of the nucleic acid construct into a permissive cell.

In a 36$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$, the 23$^{rd}$, the 24$^{th}$, the 25$^{th}$, the 26$^{th}$, the 27$^{th}$, the 28$^{th}$, the 29$^{th}$, the 30$^{th}$, the 31$^{st}$, the 32$^{nd}$ and the 33$^{rd}$ embodiment of the first aspect, the nucleotides sequence coding for E1B codes for protein E1B 55K, protein E1B 19K and protein E1B84R.

In a 37$^{th}$ embodiment of the first aspect which is also an embodiment of the 36$^{th}$ embodiment of the first aspect, protein E1B 55K, protein E1B 19K and protein E1B84R are expressed after transfer of the nucleic acid construct into a permissive cell.

In a 38$^{th}$ embodiment of the first aspect which is also an embodiment of the first, the second, the third, the fourth, the fifth, the sixth, the seventh, the eighth, the ninth, the tenth, the eleventh, the twelfth, the 13$^{th}$, the 14$^{th}$, the 15$^{th}$, the 16$^{th}$, the 17$^{th}$, the 18$^{th}$, the 19$^{th}$, the 20$^{th}$, the 21$^{st}$, the 22$^{nd}$, the 23$^{rd}$, the 24$^{th}$, the 25$^{th}$, the 26$^{th}$, the 27$^{th}$, the 28$^{th}$, the 29$^{th}$, the 30$^{th}$, the 31$^{st}$, the 32$^{nd}$, the 33$^{rd}$, the 34$^{th}$, the 35$^{th}$, the 36$^{th}$ and the 37$^{th}$ embodiment of the first aspect, the nucleotide sequence coding for E1B comprises a nucleotide sequence according to SEQ ID NO: 1.

In a 39th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th and the 38th embodiment of the first aspect, the expression unit for the expression of E1B comprises a nucleotide sequence according to SEQ ID NO: 7.

In a 40th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th and the 39th embodiment of the first aspect, the promoter of the expression unit for the expression of E1A is a murine phosphoglycerate kinase promoter and the promoter of the expression unit for the expression of E1B is an E1B promoter.

In a 41st embodiment of the first aspect which is also an embodiment of the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th and the 40th embodiment of the first aspect, the intron is different from an intron selected from the group comprising an adenoviral intron and an SV40 intron.

In a 42nd embodiment of the first aspect which is also an embodiment of the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th and the 41st embodiment of the first aspect, the intron is an constitutively spliced intron.

In a 43rd embodiment of the first aspect which is also an embodiment of the 42nd embodiment of the first aspect, the intron is a non-viral intron, preferably a mammalian intron.

In a 44th embodiment of the first aspect which is also an embodiment of the 42nd and the 43rd embodiment of the first aspect, the intron is an UBE2I intron.

In a 45th embodiment of the first aspect which is also an embodiment of the 44th embodiment of the first aspect, the intron comprises a nucleotide sequence according to SEQ ID NO: 10.

In a 46th embodiment of the first aspect which is also an embodiment of the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th and the 45th embodiment of the first aspect, the splice donor site is a splice donor site which is different from a splice donor site which is selected from the group consisting of an adenoviral splice donor site and an SV40 splice donor site.

In a 47th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th and the 46th embodiment of the first aspect, the splice donor site is a mammalian splice donor site.

In a 48th embodiment of the first aspect which is also an embodiment of the 46th and the 47th embodiment of the first aspect, the splice donor site is an UBE2I splice donor site.

In a 49th embodiment of the first aspect which is also an embodiment of the 46th, the 47th and the 48th embodiment of the first aspect, the splice donor site comprises a nucleotide sequence according to SEQ ID NO: 11.

In a 50th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 30st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th and the 49th embodiment of the first aspect, the splice acceptor site is a splice acceptor site which is different from a splice acceptor site which is selected from the group consisting of an adenoviral splice acceptor site and an SV40 splice acceptor site.

In a 51st embodiment of the first aspect which is also an embodiment of the 50th embodiment of the first aspect, the splice acceptor site is a mammalian splice acceptor site.

In a 52nd embodiment of the first aspect which is also an embodiment of the 50th and 50 embodiment of the first aspect, the splice acceptor site is a UBE2I splice acceptor site.

In a 53rd embodiment of the first aspect which is also an embodiment of the 50th, 51st and the 52nd embodiment of the first aspect, the splice acceptor site comprises a nucleotide sequence according to SEQ ID NO: 12.

In a 54th embodiment of the first aspect which is also an embodiment of the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 50, the 52nd and the 53rd embodiment of the first aspect, the intron comprising the splice donor site at the 5' end of the intron and the splice acceptor site at the 3' end of the intron comprises a nucleotide sequence according to SEQ ID NO: 13.

In a 55th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 50st, the 52nd, the 53rd and the 54th embodiment of the first aspect, the 3' UTR of the expression unit for the expression of E1B is a 3' UTR enabling posttranscriptional processing of an mRNA.

In a 56th embodiment of the first aspect which is also an embodiment of the 55th embodiment of the first aspect, the 3' UTR of the expression unit for the expression of E1B is a 3' UTR selected from the group comprising the ARF5, the DAXX, the HPRT, the RING1 and the UBE2I genes.

In a 57th embodiment of the first aspect which is also an embodiment of the 55th and the 56th embodiment of the first aspect, the 3' UTR of the expression unit for the expression of E1B is a 3' UTR of UBE2I.

In a 58th embodiment of the first aspect which is also an embodiment of the 55th, the 56th and the 57th embodiment of the first aspect, the 3' UTR of the expression unit for the expression of E1B comprises a nucleotide sequence according to SEQ ID NO: 14.

In a 59th embodiment of the first aspect which is also an embodiment of the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th and the 58th embodiment of the first aspect, the expression unit for the expression of E1A and the expression unit for the expression of E1B are arranged in a 5'->3' direction in the nucleic acid construct as follows: the promoter of the expression unit for the expression of E1A, the nucleotide sequence coding for E1A and the 3'UTR, the promoter of the expression unit for the expression of E1B, the nucleotide sequence coding for E1B, the splice donor site, the intron, the splice acceptor site and the 3' UTR.

In a 60th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th and the 59th embodiment of the first aspect, each of the nucleotide sequences which are to be expressed in a host cell, are operatively linked to a promoter.

In a 61st embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42n, the 43rd, the 44th, the 45th, the 46th, the 47th, the 48th, the 49th, the 50th, 51st, the 52nd, the 53rd, the 54th, the 55th, the 56th, the 57th, the 58th, the 59th and the 60th embodiment of the first aspect, the nucleic acid construct is coding for and capable of expressing E1A, E1B 55K, E1B 19K and/or E1B84R, preferably capable of expressing E1A, E1B 55K and E1B 19K, or preferably capable of expressing E1A, E1B 55K, E1B 19K and E1B84R.

In a 62nd embodiment of the first aspect which is also an embodiment of the 61st embodiment of the first aspect, either E1A and E1B are expressed in a host cell, or E1A, E1B and E1B84R are expressed in a host cell.

In a 63rd embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th, the 59th, the 60th, the 61st and the 62nd embodiment of the first aspect, the expression unit for the expression of E1A and the expression unit for the expression of E1B form a combined expression unit, wherein the combined expression unit comprises a nucleotide sequence according to SEQ ID NO: 5 or SEQ ID NO: 6.

In a 64th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th, the 59th, the 60th, the 61st and the 62nd embodiment of the first aspect, the expression unit for the expression of E1A and the expression unit for the expression of E1B form a combined expression unit, wherein the combined expression unit comprises a nucleotide sequence according to SEQ ID NO: 15.

In a 65th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th, the 59th, the 60th, the 61st, the 62nd and the 63rd embodiment of the first aspect, the nucleic acid construct comprises a nucleotide sequence according to SEQ ID NO: 9 or SEQ ID NO: 22.

In a 66th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th, the 59th, the 60th, the 61st, the 62nd and the 64th embodiment of the first aspect, the nucleic acid construct comprises a nucleotide sequence according to SEQ ID NO: 23.

In a 67th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th the 45th, the 46th, the 47th, the 48th, the 49th, the 50th, 51st, the 52nd, the 53rd, the 54th, the 55th the 56th, the 57th, the 58th, the 59th, the 60th, the 61st, the 62nd, the 63rd, the 64th, the 65th and the 66th embodiment of the first aspect, the nucleic acid construct comprises a 5' end and a 3' end and wherein the nucleic acid construct comprises at the 5' end and/or the 3' end at least a further nucleotide sequence.

In a 68th embodiment of the first aspect which is also an embodiment of the 67th embodiment of the first aspect, the at least a further nucleotide sequence is an adenoviral nucleotide sequence or a non-adenoviral nucleotide sequence.

In a 69th embodiment of the first aspect which is also an embodiment of the 68th embodiment of the first aspect, the adenoviral nucleotide sequence is selected from the group comprising a nucleotide sequence coding for adenoviral E2A, a nucleotide sequence coding for adenoviral E2B, a nucleotide sequence coding for adenoviral E4, a nucleotide sequence coding for a structural adenoviral protein and/or the non-adenoviral nucleotide sequence is a nucleotide sequence coding for Cre or Flp recombinase.

In a 70th embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th the 45th, the 46th, the 47th, the 48th, the 49th, the 50th, 51st, the 52nd, the 53rd, the 54th, the 55th the 56th, the 57th, the 58th, the 59th, the 60th, the 61st, the 62nd, the 63rd, the 64th, the 65th, the 66th, the 67th, the 68th and the 69th embodiment of the first aspect, the nucleic acid construct is a nucleic acid molecule.

In a 71st embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th, the 59th, the 60th, the 61st, the 62nd, the 63rd, the 64th, the 65th, the 66th, the 67th, the 68th, the 69th and the 70th embodiment of the first aspect, the nucleic acid construct is a DNA molecule.

In a 72nd embodiment of the first aspect which is also an embodiment of the first, the second, the third, the fourth, the fifth, the sixth, the seventh, the eighth, the ninth, the tenth, the eleventh, the twelfth, the 13th, the 14th, the 15th, the 16th, the 17th, the 18th, the 19th, the 20th, the 21st, the 22nd, the 23rd, the 24th, the 25th, the 26th, the 27th, the 28th, the 29th, the 30th, the 31st, the 32nd, the 33rd, the 34th, the 35th, the 36th, the 37th, the 38th, the 39th, the 40th, the 41st, the 42nd, the 43rd, the 44th, the 45th, the 46th, the 47th, the 48th, the 49th, the 50th, 51st, the 52nd, the 53rd, the 54th, the 55th, the 56th, the 57th, the 58th, the 59th, the 60th, the 61st, the 62nd, the 63rd, the 64th, the 65th, the 66th, the 67th, the 68th, the 69th, the 70th and the 71st embodiment of the first aspect, the nucleic acid construct is an RNA molecule.

The problem underlying the present invention is solved in a second aspect which is also the first embodiment of the second aspect, by a vector comprising the nucleic acid construct according to the first aspect.

In a second embodiment of the second aspect which is also an embodiment of the first embodiment of the second aspect, the vector is an expression vector.

In a third embodiment of the second aspect which is also an embodiment of the first and the second embodiment of the second aspect, the vector is selected from the group comprising a plasmid vector and a viral vector.

In a fourth embodiment of the second aspect which is also an embodiment of the third embodiment of the second aspect, the vector is a viral vector and wherein the viral vector is selected from the group comprising adenovirus, adeno-associated virus, retrovirus and lentivirus.

The problem underlying the present invention is solved in a third aspect which is also the first embodiment of the third aspect, by a cell comprising a nucleic acid construct according to the first aspect and/or a vector according to the second aspect.

In a second embodiment of the third aspect which is also an embodiment of the first embodiment of the third aspect, the nucleic acid construct is integrated into a chromosome of the cell.

In a third embodiment of the third aspect which is also an embodiment of the first and the second embodiment of the third aspect, the cell expresses E1A, E1B 55K and E1B 19K.

In a fourth embodiment of the third aspect which is also an embodiment of the first, the second and the third embodiment of the third aspect, the cell expresses E1A, E1B 55K, E1B 19K and E1B84R.

In a fifth embodiment of the third aspect which is also an embodiment of the third and the fourth embodiment of the third aspect, E1A, E1B and E1B84R are adenoviral E1A, E1B and E1B84R from adenovirus, whereby the adenovirus is preferably an adenovirus selected from the group comprising adenovirus serotype 5, adenovirus serotype 2 and adenovirus serotype 35.

In a sixth embodiment of the third aspect which is also an embodiment of the first, the second, the third, the fourth and the fifth embodiment of the third aspect, the cell expresses a recombinase, preferably a Cre or Flp recombinase.

In a seventh embodiment of the third aspect which is also an embodiment of the first, the second, the third, the fourth, the fifth and the sixth embodiment of the third aspect, the cell expresses at least one protein selected from the group comprising E2A protein, E2B protein, E4 protein, a structural protein of adenovirus and each and any combination thereof.

In an eighth embodiment of the third aspect which is also an embodiment of the first, the second, the third, the fourth, the fifth, the sixth and the seventh embodiment of the third aspect, the cell is a cell line.

In a ninth embodiment of the third aspect which is also an embodiment of the eighth embodiment of the third aspect, the cell line is a permanent cell line.

In a tenth embodiment of the third aspect which is also an embodiment of the eighth and the ninth embodiment of the third aspect, the cell line is an amniocytic cell line.

In an eleventh embodiment of the third aspect which is also an embodiment of the eighth, the ninth and the tenth embodiment of the third aspect, the cell line is a human cell line.

The problem underlying the present invention is solved in a fourth aspect which is also the first embodiment of the fourth aspect, by a method for the production of a permanent aminocytic cell line comprising the step of introducing into a amniocytic cell a nucleic acid construct according to the first aspect and/or a vector according to the second aspect and preferably allowing the nucleic acid construct and/or the vector to integrate into a chromosome of the amniocytic cell.

In a second embodiment of the fourth aspect which is also an embodiment of the first embodiment of the fourth aspect, the method further comprises the step of cultivating the cell into which the nucleic acid construct according to the first aspect and/or the vector according to the second aspect has been introduced.

In a third embodiment of the fourth aspect which is also an embodiment of the first and the second embodiment of the fourth aspect, the step of introducing the nucleic acid construct according to the first aspect and/or the vector according to the second aspect is a transfection.

In a fourth embodiment of the fourth aspect which is also an embodiment of the first, the second and the third embodiment of the fourth aspect, the amniocytic cell is a primary amniocyte, preferably the primary amniocyte is a human primary amniocyte.

In a fifth embodiment of the fourth aspect which is also an embodiment of the first, the second, the third and the fourth embodiment of the fourth aspect, the cell expresses at least an adenoviral protein selected from the group comprising E1A, E1B and E1B84R, preferably the cell expresses adenoviral proteins E1A, E1B, and E1B84R and each and any combination thereof.

The problem underlying the present invention is solved in a fifth aspect which is also the first embodiment of the fifth aspect, by a permanent aminocytic cell line obtainable by a method according to the fourth aspect.

The problem underlying the present invention is solved in a sixth aspect which is also the first embodiment of the sixth aspect, by a permanent amniocytic cell line, wherein the permanent aminocytic cell line is cell line SGT11 1T3.1D9 (deposited with DSM under accession number ACC3134) and cell line SGT11 1T3.1G3 (deposited with DSM under accession number ACC3135).

The problem underlying the present invention is solved in a seventh aspect which is also the first embodiment of the seventh aspect, by the use of a cell according to any one of the first, the second, the third, the fourth, the fifth, the sixth and the seventh embodiment of the third aspect and/or of a cell line according to any one of the eighth, the ninth, the tenth and the eleventh embodiment of the third aspect for producing a vector, preferably a gene transfer vector, more preferably a viral gene transfer vector.

In a second embodiment of the seventh aspect which is also an embodiment of the first embodiment of the seventh aspect, the vector is a virus.

The problem underlying the present invention is solved in an eighth aspect which is also the first embodiment of the eighth aspect, by the use of a cell according to any one of the first, the second, the third, the fourth, the fifth, the sixth and the seventh embodiment of the third aspect and/or of a cell line according to any one of the eighth, the ninth, the tenth and the eleventh embodiment of the third aspect for producing a protein, wherein the cell or cell line comprises a further nucleotide sequence coding for the protein and wherein the further nucleotide sequence is part of an expression unit.

In a third embodiment of the seventh aspect which is also an embodiment of the first and the second embodiment of the seventh aspect, the vector and the virus are each and independently from each other selected from the group comprising an adenovirus, an AAV (adeno-associated virus), a retrovirus, a lentivirus, a chimeric adenovirus-AAV, a chimeric adenovirus-retrovirus and a chimeric adenovirus-lentivirus.

The problem underlying the present invention is solved in a ninth aspect which is also the first embodiment of the ninth aspect, by the use of a cell according to any one of the first, the second, the third, the fourth, the fifth, the sixth and the seventh embodiment of the third aspect and/or of a cell line according to any one of the eighth, the ninth, the tenth and the eleventh embodiment of the third aspect for producing an adenovirus mutant.

The problem underlying the present invention is solved in a tenth aspect which is also the first embodiment of the tenth aspect, by a method for the production of a gene transfer vector or an adenovirus mutant comprising the step of cultivating a cell according to any one of the first, the second, the third, the fourth, the fifth, the sixth and the seventh embodiment of the third aspect and/or of a cell line according to any one of the eighth, the ninth, the tenth and the eleventh embodiment of the third aspect in a cell growth medium providing a supernatant, wherein the cell or cell line contains the nucleic acid construct according to the first aspect and as a further nucleotide sequence which is the nucleic sequence of the gene transfer vector or the adenovirus mutant, and wherein the method comprises the step of harvesting the gene transfer vector or the adenovirus mutant from the cell or from the supernatant.

The problem underlying the present invention is solved in an eleventh aspect which is also the first embodiment of the eleventh aspect, by a method for the production of a protein comprising the step of cultivating a cell according to any one of the first, the second, the third, the fourth, the fifth, the sixth and the seventh embodiment of the third aspect and/or of a cell line according to any one of the eighth, the ninth, the tenth and the eleventh embodiment of the third aspect in a cell growth medium providing a supernatant, wherein the cell or cell line contains the nucleic acid construct according to the first aspect and a nucleotide sequence coding for the protein, wherein said nucleotide sequence coding for the protein is expressed in said cell or cell line, and wherein the method comprises the step of harvesting the protein from the cell or from the supernatant.

Without wishing to be bound by any theory, the instant invention is based on the following surprising and unexpected findings.

When primary amniocytes, obtained by amniocentesis, are cultivated in vitro in cell culture dishes without feeder layer, they can be maintained for a limited number of passages before they change morphology, become large in size, acquire a senescent phenotype and stop proliferation. The number of passages until the appearance of the senescent phenotype varies with the number of primary cells used for initiation of the culture. Under standard conditions, i.e. starting with 1 or 2 ml of amniotic fluid, cells can be passaged about 10 times, corresponding to about a total of 30 to 35 PDs, until they acquire a senescent phenotype with the changes described above.

It has previously been found that transfection of primary amniocytes with pSTK146, a plasmid of the prior art expressing the E1A and E1B genes of hAd5, resulted in the appearance of cell clones, following chromosomal integration of the E1A and E1B expressing DNA, consisting of proliferating cells that could be expanded and from which permanent cell lines could be established, among them cell line N52.E6 (Schiedner et al., 2000; EP00979539), which can be used, for example, for production of adenovirus vectors.

Plasmid pSTK146 codes for the E1A proteins and the E1B 55K and E1B 21K proteins (the latter sometimes also being referred to as E1B 19K protein). In pSTK146 the E1B coding sequences is followed by DNA sequences from the SV40 virus containing an intron and the 3' UTR, both derived from SV40. The splice donor (SD) is derived from the E1B non-coding sequence of adenovirus type 5 and the splice acceptor is derived from SV40.

After transfection of primary amniocytes with plasmid pSTK146 between passages 7 and 9, appearance of a high number of cell clones consisting of small and proliferating cells was observed, which is in accordance with previously published results (Schiedner et al., 2000). After isolation and transfer to individual cell culture dishes (the first passage to an individual cell culture dish is referred to herein as polyclonal passage 1), the individual clones were further propagated and carefully analysed with respect to growth and morphology. It was observed that quite soon after polyclonal passage 1 the number of viable and surviving cell clones started to decrease. Only a rather small number of clones survived beyond polyclonal passage 10, corresponding to a total of approximately 65 PDs, when counting from the initial seeding of the primary amniocytes, and to approximately 30 to 35 PDs after transfection with plasmid pSTK146. Microscopic examination indicated that the failed cell clones underwent a crisis that was characterized mainly by a strong increase in cell size and complete stop of cell proliferation, and in part by signs of cell death and detachment, i.e. consistent with the acquisition of a senescent phenotype.

The instant invention overcomes these shortcomings More specifically, the nucleic acid construct of the present invention when introduced into primary aminocytes prevents this crisis of E1-immortalized primary amniocytes to a large extent. After transfection of amniocytes with the nucleic acid construct of the present invention, it was found that a far higher percentage of clones, containing the E1A and E1B genes chromosomally integrated, did not show any sign of crisis, and rather continued to proliferate permanently. It was also found that most of the thus established cell lines, including the cells and cells of the present invention which are disclosed herein grew to a much higher density in adherent cell culture than N52.E6 cells.

Furthermore, the present inventors surprisingly found that the chromosomal karyotype of cells immortalized with the nucleic acid construct of the present invention and of the cells of the present invention, although being polyploid as expected, was very stable over many passages, with surprisingly few structural abnormalities being present. This is advantageous with regard to the fact that for industrial production of biologics such as proteins, viruses, virus-like particles (VLPs), vaccines or viral vectors, which are used in humans as therapeutic or prophylactic drugs or as diagnostics and for acceptance by regulatory agencies such as the European Medicines Agency (EMA) or the FDA, producer cells and producer cell lines used for the production of such biologics must be well-characterized with respect to growth, stability and safety. Long-term genetic stability is a precondition for industrial production of well-characterized products of high quality (e.g. characterized by consistent glycosylation of glycoproteins), activity (e.g. characterized by consistent immunogenicity of vaccines) and uniformity.

A further finding underlying the present invention is that genetic stability of the cells and cell lines of the invention relates to the length of their telomeres: telomeres in the cells and cell lines of the invention were found to be much longer than those in N52.E6 cells. Insofar, the present invention provides means and methods for the immortalization of primary amniocytes and for the generation of permanent aminocyte cell lines with a strongly increased efficiency. In addition, the present invention also provides permanent amniocyte cell lines having high genetic stability.

A still further surprising advantage of the subject matter of the present invention is that the production of a ΔE1Ad vector in the cells and cell lines of the present invention did not result in the generation of replication competent adenoviruses RCAs or in HDEPs, despite the small overlap between the pIX gene sequences of the ΔE1Ad vector genome and the chromosomally integrated recombinant DNA.

DETAILED DESCRIPTION

The present invention is related in a first aspect to a nucleic acid construct comprising
an expression unit for the expression of E1B, wherein the expression unit comprises a promoter, a nucleotide sequence coding for E1B, and a 3'UTR and wherein the promoter is operatively linked to the nucleotide sequence coding for E1B, wherein the 3' UTR comprises 30 or less than 30 Exonic Enhancer Elements (ESEs).

As preferably used herein a nucleic acid construct is a nucleic acid molecule. The nucleic acid construct may be part of a larger nucleic acid molecule containing the nucleic acid construct. In an embodiment the nucleic acid construct is an isolated nucleic acid construct.

Such nucleic acid construct can be either a single-stranded nucleic acid molecule or a double-stranded nucleic acid molecule. In case the nucleic acid construct is a double-stranded nucleic acid molecule the nucleic acid preferably comprises two strands which are essentially complementary to each other. Such complementarity is typically defined by base pairing rules such as Watson-Crick base pairing rules. As preferably used herein, a double-stranded nucleic acid molecule is a one-piece nucleic acid molecule.

In an embodiment of the invention the nucleic acid construct of the invention comprises in addition to the expression unit for the expression of E1B an expression unit for the expression of E1A. Preferably, the expression unit for the expression of E1A comprises a promoter, a nucleotide sequence coding for E1A, and a 3' UTR and wherein the promoter is operatively linked to the nucleotide sequence coding for E1A.

In a further embodiment of the invention the nucleic acid construct comprises both the expression unit for the expression of E1B and the expression unit for the expression of E1A, whereby the nucleic acid construct forms a one-piece nucleic acid molecule. A one-piece nucleic acid molecule preferably means that the 5' terminal nucleotide of one of the expression units such as the expression unit of for the expression of E1A is linked, preferably covalently linked to the 3' terminal nucleotide of one of the other expression units such as the expression unit for the expression of E1B. A one-piece nucleic acid molecule can, alternatively, be one where the 5' terminal nucleotide of the expression unit for the expression of E1B is linked, preferably covalently linked to the 3' terminal nucleotide of the expression unit for the expression of E1A. In a further embodiment of a one-piece nucleic acid of the present invention, some nucleotides are shared by both the expression unit for the expression of E1A and the expression unit for the expression of E1B; in other words, some nucleotides are overlapping in/for both expression units. For example, in case the expression unit for the expression of E1B is arranged downstream, i.e. in 3' direction, of the expression unit for the expression of E1A, some nucleotides of the 3' UTR of the expression unit for the expression of E1A are also nucleotides of the 5' region of the promoter of the expression unit for the expression of E1B.

In an alternative embodiment, in case the expression unit for the expression of E1A is arranged downstream of the expression unit for the expression of E1B some nucleotides of the 3' UTR of the expression unit for the expression of E1B are also nucleotides of the 5' region of the promoter of the expression unit for the expression of E1A. It will be acknowledged by a person skilled in the art that the extent of such overlapping may vary, depending on the particularities of the overlapping sequences. In another embodiment of the present invention some nucleotides forming the expression unit for the expression of E1A overlap with some nucleotides forming the expression unit for the expression of E1B. In a further embodiment of the nucleic acid construct of the invention comprising both the expression unit for the expression of E1B and the expression unit for the expression of E1A, whereby the nucleic acid construct forms a one-piece nucleic acid molecule, such nucleic acid construct and nucleic acid molecule, respectively, is a double-stranded nucleic acid molecule, whereby the expression unit for the expression of E1B is located on the first strand of the double-stranded nucleic acid molecule and the expression unit for the expression of E1A is located on the second strand of the double-stranded nucleic acid molecule. In this embodiment, preferably, the strand bearing the expression unit for the expression of E1A is extended by a first extending nucleotide sequence and the strand bearing the expression unit for the expression of E1B is extended by a second extending nucleotide sequence, whereby if the first extending nucleotide sequence is attached to the 5' end of the expression unit for the expression of E1A, the second extending nucleotide sequence is attached to the 3' end of the expression unit for the expression of E1B; and if the first extending nucleotide sequence is attached to the 3' end of the expression unit for the expression of E1A, the second extending nucleotide sequence is attached to the 5' end of the expression unit for the expression of E1B; in these embodiments the first extending nucleotide sequence and the second extending nucleotide sequence are essentially complementary to each other. In an embodiment the first extending nucleotide sequence and the second extending nucleotide sequence are base pairing to an extent that a double-stranded structure is formed which is preferably stable under physiological conditions such as conditions existing in a living mammalian organism. In a preferred embodiment the first extending nucleotide sequence is essentially complementary to the nucleotide sequence of the expression unit for the expression of E1B, and the second extending nucleotide sequence is essentially complementary to the nucleotide sequence of the expression unit for the expression of E1A. In the embodiments of the nucleic acid construct of the present invention where the nucleic acid construct comprises both the expression unit for the expression of E1B and the expression unit for the expression of E1A, whereby the nucleic acid construct forms a one-piece nucleic acid molecule, such nucleic acid construct and nucleic acid molecule, respectively, is a double-stranded nucleic acid molecule, whereby the expression unit for the expression of E1B is located on the first strand of the double-stranded nucleic acid molecule and the expression unit for the expression of E1A is located on the second strand of the double-stranded nucleic acid molecule, the individual expression unit is thus a single-stranded molecule, whereby the double-stranded structure which is, in the art, regarded as being required for a transcription unit, is preferably formed the first and second, respectively, extending nucleotide sequence. It will be further acknowledged by a person skilled in the art that in said embodiments of the nucleic acid construct of the invention forming a double-stranded nucleic acid molecule with the first strand comprising the expression unit for the expression of E1A and the second strand comprising the expression unit for the expression of E1B, the expression unit for the expression of E1A and the expression unit for the expression of E1B are either arranged in the same direction or opposite direction.

In a further embodiment the nucleic acid construct of the invention is a two-piece nucleic acid molecule comprising a first nucleic acid molecule which is the first piece of the two-piece nucleic acid and a second nucleic acid molecule which is the second piece of the two-piece nucleic acid, wherein the first nucleic acid molecule comprises the expression unit for the expression of E1B and the second nucleic acid molecule comprises the expression unit for the expression of E1A. It is within the present invention that the first nucleic acid molecule and the second nucleic acid molecule are each and independently either a double-stranded nucleic acid or a single-stranded nucleic acid molecule. In an embodiment both the first nucleic acid molecule and the second nucleic acid molecule are a double-stranded nucleic acid molecule; in an alternative embodiment both the first nucleic acid molecule and the second nucleic acid molecule are a single-stranded nucleic acid molecule. In those embodiments of the nucleic acid construct of the invention where the nucleic acid molecule is a single-stranded RNA nucleic acid molecule, the nucleic acid construct can be a retroviral vector or part of a retroviral vector. In those embodiments of the nucleic acid construct of the invention where the nucleic acid molecule is a double-stranded DNA nucleic acid molecule, the nucleic acid construct can be a plasmid or part of a plasmid.

As preferably used herein an expression unit for the expression of a gene and gene product, respectively, comprises a promoter, a nucleotide sequence coding for the gene and gene product, respectively, and a 3' UTR. The promoter is operatively linked to the coding nucleotide sequence so that the coding sequence is translated if the expression unit is present in an expression permissive environment such as a permissive cell or an in vitro translation system.

A 3' UTR as preferably used herein is a particular section of messenger RNA (mRNA). Preferably, it starts with the nucleotide immediately following the stop codon of the coding region and ends with the nucleotide immediately before the mRNA cleavage site. Typically, several regulatory sequences are found in the 3' UTR: (a) A polyadenylation signal, usually AAUAAA, or a slight variant; this marks the site of cleavage of the transcript approximately 30 base pairs past the signal by an endonuclease, followed by the addition of several hundred adenine residues (poly-A tail) (Proudfoot, 2011); optionally, (b), not rarely binding sites for proteins, that may affect the mRNA's stability or location in the cell, like SECIS elements which may direct the ribosome to translate the codon UGA as selenocysteines rather than as a stop codon, or AU-rich elements (AREs), stretches consisting of mainly adenine and uracil nucleotides (which can either stabilize or destabilize the mRNA depending on the protein bound to it; and/or, optionally, (c) binding sites for microRNAs (miRNAs).

It will be acknowledged by a person skilled in the art that the nucleotide sequence coding for E1B may be the one of wild type adenovirus, preferably of wild type adenovirus serotype 5 (Ad5). Alternatively, the nucleotide sequence coding for E1B may be different therefrom, however, due to the degeneracy of the genetic code, codes for E1B having the amino acid sequence of wild type adenovirus preferably of wild type adenovirus serotype 5 (Ad5). In a preferred embodiment the nucleotide sequence coding for E1B is the one of SEQ ID NO: 1. The same considerations equally apply to the nucleotide sequence coding for E1A. In a preferred embodiment the nucleotide sequence coding for E1A is the one of SEQ ID NO: 2. It will also be acknowledged by a person skilled in the art that the nucleotide sequences coding for E1A and/or E1B may be codon-optimized to achieve the best possible expression levels of Ad5 E1A and/or E1B, a strategy that is commonly referred to as codon optimization. Such codon optimization may also encompass or entail a reduction in aberrant splicing, whereby such aberrant splicing is to be avoided in connection with the nucleic acid construct of the present invention.

Exonic splicing enhancers (ESE) within exons are believed to play an important role in the regulation of splice-site selection of constitutive and alternative splicing of pre-mRNA transcripts. The analysis of disease alleles by protocols based on SELEX (Systematic Evolution of Ligands by Exponential enrichment) initially identified ESE elements which were characterized by purine-rich sequences, but also by AC- or pyrimidine-rich motifs (Schaal T D and Maniatis T, 1999). Generally, it is suggested that ESEs are located close to splice sites (Berget S M, 1995). In contrast to transcriptional enhancers, ESEs are strongly position-dependent; they can (i) enhance splicing when present upstream of splice donor (SD) site and/or downstream of a splice acceptor (SA) site, and (ii) repress splicing when found in intronic sequences. ESE elements can compensate for non-consensus ("weak") splice signals in exons, whereas consensus splice sites eliminate the need of enhancer-dependency (reviewed by Fairbrother et al., 2002).

A computational method, RESCUE-ESE, was developed that predicts which sequences have ESE activity by statistical analysis of exon-intron and splice site composition (Fairbrother et al., 2002; Fairbrother et al., 2004). Hexameric sequences were regarded as having ESE activity when they satisfied two criteria: (i) significant enrichment within human exons relative to introns, and (ii) higher frequency in exons with non-consensus (weak) splice sites than in exons with consensus splice sites. By analysing a large data set of human gene sequences, this method identified out of 4096 possible hexamers a set of 238 hexameric ESE motifs (6%) (Table 3) that originally had been grouped in distinct motif clusters, based on sequence similarities. The selected hexameric ESE motifs display(ed) enhancer activity in vivo, whereas point mutations of these sequences resulted in a sharply reduced activity (Fairbrother et al., 2002). According to Fairbrother and colleagues ESE sequences should be strongly selected for in constitutively spliced exons and generally avoided in intronic sequences in the vicinity of splice sites (Fairbrother et al., 2002).

It is within the present invention that an ESE is one of the ESEs indicated in Table 3. However, it is also within the present invention that an ESE is a sequence, preferably a hexameric sequence which satisfies the two criteria (i) and (ii) as defined above. In connection therewith it is to be acknowledged that it is within the present invention that the nucleic acid construct contains 30 or less than 30 ESEs, whereby such 30 or less than 30 ESEs may be different or identical ESEs in terms of their nucleotide sequence. If, for example, the number of ESEs is 30, it is within the present invention that each and any of the 30 ESEs has the same nucleotide sequence. It is, however, also within the present invention that the nucleotide sequence of each and any of the 30 ESEs is different from the other 29 ESEs. Finally, it is within the present invention that the nucleotide sequence of some of the 30 ESEs is the same, whereas the nucleotide sequence of the remaining ESEs is different therefrom and, optionally also different within the group of the remaining ESEs.

As preferably used herein the expression that the 3' UTR comprises 30 or less than 30 Exonic Enhander Elements (ESEs) means that the 3'UTR comprises 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 or 0 Exonic Enhancer Elements (ESEs).

In an embodiment of the nucleic acid construct of the present invention the 3' UTR comprises 30 Exonic Enhancer Elements (ESEs) or less than 30 Exonic Enhancer Elements (ESEs) within a stretch of 200 consecutive nucleotides of the 3' UTR. In a further embodiment of the nucleic acid construct of the present invention the 3' UTR comprises 30 Exonic Enhancer Elements (ESEs) or less than 30 Exonic Enhancer Elements (ESEs), whereby the 3' UTR comprises less than 200 nucleotides. In an embodiment of the present invention a 3' UTR may also be an artificial 3'UTR. In a further embodiment, the 3'UTR comprises at least 50, or at least 100 nucleotides or at least 200 nucleotides. It will, however, be acknowledged by a person skilled in the art that 3' UTRs in humans have a length between 21 nucleotides and 8555 nucleotides and an average length of 1028 nucleotides (Pesole et al., 2001), and that each any any of these lengths or any of the lengths within the indicated values, in various embodiments of the present invention, may be a length of the 3' UTR as contained in the nucleic acid construct of the invention.

In a further embodiment of the nucleic acid construct of the present invention the 3' UTR comprises 25 Exonic Enhancer Elements (ESEs) or less than 25 Exonic Enhancer Elements (ESEs) In a further embodiment of the nucleic acid construct of the present invention the 3' UTR comprises 25 Exonic Enhancer Elements (ESEs) or less than 25 Exonic Enhancer Elements (ESEs), whereby the 3' UTR comprises less from about 150 to about 199 nucleotides. As preferably used herein the expression that the 3' UTR comprises 25 or less than 25 Exonic Enhander Elements (ESEs) means that the 3'UTR comprises 25, 24, 23, 22, 21, 20, 19, 18, 17, 16, 15, 14, 13, 12, 11, 10, 9, 8, 7, 6, 5, 4, 3, 2, 1 or 0 Exonic Enhancer Elements (ESEs).

In a further embodiment of the nucleic acid construct of the present invention the 3' UTR comprises 20 Exonic Enhancer Elements (ESEs) or less than 20 Exonic Enhancer Elements (ESEs) In a further embodiment of the nucleic acid construct of the present invention the 3' UTR comprises 20 Exonic Enhancer Elements (ESEs) or less than 20 Exonic Enhancer Elements (ESEs), whereby the 3' UTR comprises less from about 100 to about 149 nucleotides. As preferably used herein the expression that the 3' UTR comprises 25 or less than 25 Exonic Enhander Elements (ESEs) means that the 3'UTR comprises 25, 24, 23, 22, 21, 20, 19, 18, 17, 16, 15, 14, 13, 12, 11, 10, 9, 8, 7, 6, 5, 4, 3, 2, 1 or 0 Exonic Enhancer Elements (ESEs).

In accordance therewith, in order to identify the number of ESEs within the first 200 nt. of the 3' UTR, or of any other stretch of nucleotides within a given nucleotide sequence, that is located immediately downstream from the last intron, a sequence of interest is selected and analyzed by a software tool that is suitable for pair-wise nucleotide sequence alignment of each hexamer with a specific query sequence. Examples are the well known FASTA sequence alignment software package or one that has been developed by Faribrother et al., 2004. Alternatively, the ESE motifs can also be identified by using a simple word-processing software.

For searching of hexameric ESE motifs (either case sensitive or insensitive) within a selected 3'UTR, the first hexamer sequence (of a total number of 238) is typed into a standard search dialogue. The search always begins after the last selected nucleotide and is performed downwards from the beginning of the document. When the motif is found, the first instance encountered is highlighted in the document window. To continue the search to find the next instance of the first hexamer motif, the "Find next" option within the standard search dialogue of the software is selected. If the "Find" option is chosen again, the search position is reset to the beginning of the document and other hexameric motifs can be searched within the current sequence. The search is complete, when all of the 238 hexameric motifs have been searched. The number of overall matches is designated as "total matches", the number of individual hexameric matches as "unique matches". It is even possible to perform the alignment of the hexamers with the query sequence by visual inspection.

In an embodiment of the present invention, the 3'UTR of the expression unit for the expression of E1B is different from a 3' UTR of Simian virus 40 (SV40). Preferably the 3'UTR of Simian virus 40 is the nucleotide sequence according to SEQ ID NO: 3.

In a preferred embodiment the nucleotide sequence of an expression unit for the expression of E1B comprises a nucleotide sequence according to SEQ ID NO: 7.

In a preferred embodiment the nucleotide sequence of an expression unit for the expression of E1A comprises a nucleotide sequence according to SEQ ID NO: 8.

In one embodiment of the present invention the expression unit for the expression of E1B comprises a splice donor site, an intron and a splice acceptor site. This entity consisting of a splice donor site, an intron and a splice acceptor site is sometimes also referred to as intron. The advantage of including an intron in the E1B transcription unit is, that by doing so protein expression is enhanced because splicing enhances mRNA export from the nucleus to the cytoplasm where translation takes place. The RNA elements required for RNA splicing are well known (Lewin B, Genes VIII, Pearson Education International, 2004) and consensus sequences from mammalian splice donor and and splice acceptor sites have been derived (Burset et al., 2001). The splice donor site includes the almost invariant sequence GU (GU at RNA level corresponds to GT at the DNA level) at the 5' end of the intron and this dinucleotide is located within a larger, less highly conserved consensus region. The splice acceptor site includes the almost invariant sequence AG terminating the intron. A pyrimidine-rich region is located upstream of the splice acceptor site and further upstream from this pyrimidine-rich region is the branch point. The consensus sequence for the GT-AG group of splice sites derived by Burset et al (supra) for the splice donor is $M_{70}A_{60}G_{80}|GT R_{95}A_{71}G_{81}T_{46}$ and for the splice acceptor including the pyrimidine-rich region it is $Y_{73}Y_{75}Y_{78}Y_{79}Y_{80}Y_{79}Y_{78}Y_{81}Y_{86}Y_{86}NC_{71}AG|G_{52}$, where M corresponds to nucleotides A or C, R to A or G, Y to C or T and S to C or G. The consensus sequence for the rather rarely observed GC-AG group of splice sites can also be found in Burset et al. (supra).

While in principle sequences encoding introns, splice donor and splice acceptor sites with good splicing properties can be selected by trial and error, it is suggested here to choose an intron, that is known to function in a constitutive manner and that also is not involved in alternative splicing events. The term "constitutive" as used here with respect to introns is a term, well known to the expert, indicating, that the intron functions in many cell types and is not subject to a specific regulation resulting in alternative splicing. The term "alternative splicing" describes a process in which exons present in a precursor mRNA (pre-mRNA) can be connected in different ways during splicing resulting in different mRNAs. Thus, within the scope of the present invention preference is given to short introns that are constitutively spliced. Preference is given to mammalian, preferentially human, introns over introns derived from DNA viruses, since RNAs transcribed from DNA viruses are very frequently spliced in alternative ways. Introns functioning in a constitutive manner can be chosen for example using an algorithm as described by Kim and colleagues (Kim et al., 2007).

In an embodiment of the present invention, the intron of the expression unit for the expression of E1B is different from an intron of Simian virus 40 (SV40). Preferably, the nucleotide sequence of the intron of Simian virus 40 is the nucleotide sequence according to SEQ ID NO: 4.

As an alternative strategy for the selection of a combination of splice donor, intron, splice acceptor and 3'UTR including polyadenylation sites, and instead of choosing the individual elements that occur naturally in vertebrate genomes it is also possible to use artificial splice donor and splice acceptor sites corresponding to established consensus sequences as template (e.g. Burset et al., supra, for splice donor/splice site selection; Proudfoot, supra, for polyadenylation site selection).

In an embodiment of the present invention the nucleic acid construct comprises a nucleotide sequence coding for the adenoviral pIX gene or a part thereof.

In a further embodiment the nucleic acid construct comprises part of the 5'-UTR of the pIX gene, which overlaps with the most 3' UTR of the E1B transcription unit, to allow for generation of the E1B 84R protein (Sieber et al. 2007).

As preferably used, a permissive cell is a cell, preferably a mammalian cell which allows the expression of the nucleic acid construct of the present invention.

In an embodiment of the present invention, the expression of the E1A and E1B coding sequences if the nucleic acid construct of the present invention is under control of constitutive promoters. Preferably the E1A coding sequence is under control of a constitutive heterologous (i.e. non-adenoviral) promoter such as the human (Singer-Sam et al., 1984) or murine (Adra et al., 1987) phosphoglycerate kinase (PGK) promoter or the early promoter from human or murine cytomegalovirus (hCMV promoter or mCMV promoter, respectively) (Boshart et al., 1985, Dorsch-Hasler et al., 1985), and the E1B coding sequence is under the control of the natural E1B promoter. In a preferred composition according to the present invention, the E1A coding sequence is under control of the murine PGK promoter and the E1B coding sequence is under control of the natural E1B promoter. However, within the scope of this invention it is also possible to place the E1B coding sequence under control of a heterologous promoter such as the PGK promoter or another constitutive promoter.

In another embodiment, the promoter of the expression unit for the expression of E1A is an adenoviral promoter, a regulatable or an inducible promoter. In accordance therewith the E1A coding sequence is placed under control of a regulatable promoter, in which promoter activity can be controlled by adding or removing external factors (Overdhana S, et al., 2006). Examples include the use of promoters that can be regulated by metal ions (Wurm et al., 1986), by steroids (Hynes et al., 1982; No et al., 1996), by IPTG (Hu et al., 1987), by tetracycline (Baron et al., 1997; Loew et al., 2010), or by mifepristone (Burcin et al., 1998). There are several advantages of using an inducible promoter to control E1A expression. First, during generation and maintenance of the immortalized cell lines, the level of E1A expression can be fine-tuned and better controlled than using a constitutive promoter and thus E1A expression can be optimized to increase efficiency of immortalization and maintenance. It is well known that expression of E1A at high levels can be detrimental to cells due to the pro-apoptotic activity of E1A. Second, placing E1A under inducible promoter control will reduce or abolish the tumorigenicity of established cell lines, since in the absence of the inducible agent (such as Doxycyclin when using the Tet-on regulatable system) E1A is not expressed. When producing biologics for human therapeutic or prophylactic use, for safety reasons it is advantageous that the cell lines that are used for production of biologics would not be tumorigenic, even not in immune-compromised humans. Experimentally, tumorigenicity of cell lines used for production of biologics is usually tested by subcutaneous injection of a cell suspension in immunodeficient animals such as immunodeficient mice.

In an embodiment of the present invention, the E1A cDNA of adenovirus is placed under the control of a Tetracycline (Tet)-inducible promoter. The general strategy for establishing the Tet-On Advanced System (Clontech) is to first transfect target cells with pTet-On Advanced to create a cell line stably expressing the Tet-On Advanced transactivator.

In an embodiment of the nucleic acid construct of the invention the nucleic acid construct comprises a 5' end and a 3' end and wherein the nucleic acid construct comprises at the 5' end and/or the 3' end at least a further nucleotide sequence. In an embodiment of the nucleic acid construct of the invention where the nucleic acid construct is a one-piece nucleic acid molecule comprising both the expression unit for the expression of E1A and the expression unit for the expression of E1B such one-piece nucleic acid molecule comprises at the 5' end and/or the 3' end at least a further nucleotide sequence. In an embodiment of the nucleic acid construct of the invention where the nucleic acid construct is a two-piece nucleic acid molecule comprising a first nucleic acid molecule and a second nucleic acid molecule, wherein the first nucleic acid molecule comprises the expression unit for the expression of E1B and the second nucleic acid molecule comprises the expression unit for the expression of E1A, a further nucleotide sequence is attached to (a) the 5' end and/or the 3' end of the first nucleic acid molecule, (b) the 5' end and/or the 3' end of the second nucleic acid molecule, or (c) the 5' end and/or the 3' end of the first nucleic acid molecule and the 5' end and/or the 3' end of the second nucleic acid molecule. In an embodiment of each and any of the above recited embodiments, the further nucleotide sequence is a further nucleotide sequence as defined herein.

In an embodiment the E1B 55K protein comprises an amino acid sequence according to SEQ ID NO: 16; in a further embodiment the nucleotide sequence coding for the E1B 55K protein comprises a nucleotide sequence according to SEQ ID NO: 17.

In an embodiment the E1B 19K protein comprises an amino acid sequence according to SEQ ID NO: 18; in a further embodiment the nucleotide sequence coding for the E1B 19K protein comprises a nucleotide sequence according to SEQ ID NO: 19.

In an embodiment the E1B84R protein comprises an amino acid sequence according to SEQ ID NO: 20; in a further embodiment the nucleotide sequence coding for the E1B84R protein comprises a nucleotide sequence according to SEQ ID NO: 21.

In an embodiment of the invention the nucleic acid construct comprises at least one further nucleotide sequences. In an embodiment the further nucleotide sequence is an adenoviral sequence. The adenoviural sequence may be one coding for non-structural proteins; in accordance therewith the further nucleotide sequence comprises in an embodiment an adenoviral nucleotide sequence selected from the group comprising a nucleotide sequence coding for adenoviral E2A, a nucleotide sequence coding for adenoviral E2B, and a nucleotide sequence coding for adenoviral E4. In an embodiment the further nucleotide sequence comprises an adenoviral sequence coding for a structural adenoviral protein, whereby such structural adenoviral protein is selected from the group comprising fiber, pIX and penton base. In a further embodiment, the further nucleotide sequence comprises a non-adenoviral nucleotide sequence; in an embodiment the further nucleotide sequence comprises a nucleotide sequence codign for Cre or Flp recombinase. Nucleotide sequences coding for these proteins and functions, respectively, are known to a person skilled in the art and may, among others, be taken from public databases such as the NCBI database (e.g. NCBI: AC_000008.1 for the human adenovirus type 5 genome; for Cre from GenBank: X03453.1; for Flp from GenBank: J01347.1). The particular sequences coding for the viral and non-viral proteins can be used either as natural sequences or as sequences the have been codon-optimized for improved expression in mammalian cells.

It is within the present invention that this kind of further adenoviral nucleotide sequence is part of the nucleic acid construct of the invention, whereby the nucleic acid construct is either a one-piece nucleic acid molecule or a two-piece nucleic acid molecule. It is, however, also within the present invention that one or several of these adenoviral nucleotide sequences are part of a further nucleic acid molecule, preferably a vector such as a plasmid or a viral vector, whereby such vector is to be introduced into a cell of interest such as a host cell, prior, together with or after the nucleic acid construct of the invention has been introduced into such host cell.

In a preferred embodiment the nucleic acid construct is pSTK146 UBE2I. This construct comprises a nucleotide sequence according to SEQ ID NO: 9. This nucleic acid construct was designed to contain splice donor, intron, splice acceptor and 3' UTR sequence elements of the human UBE2I gene for optimized synthesis and processing of E1 mRNA transcripts: a) a mammalian, short and constitutive intron including a splice donor and a splice acceptor site at the 5' or at the 3' end, respectively, and b) a RNA cleavage and a polyadenylation site. As was found in the present invention, this construct enabled an at least three-fold stronger expression of the E1B 55K protein after transient transfection compared to the previously used pSTK146 plasmid and a 37 kDa E1B protein, resulting from aberrant splicing, was not detected. In addition, pSTK146 UBE2I has a short pIX sequence inserted immediately after the splice acceptor of the UBE2I gene to allow for expression of the E1B 84R protein.

In plasmid pSKT 146 UBE2I the various functional elements are located at the following positions, whereby reference is made to the nucleotide sequence of SEQ ID NO: 9:

Murine pgk promoter: nts. 2230-2741
Ad5 E1A: nts. 2808-3793
Ad5 E1B promoter: nts. 3885-3967
Ad E1B 55K: nts. 4267-5757
UBE2I intron: nts. 5767-5920
Ad5 E1B 84R C-terminus: nts. 5921-5936
UBE2I 3' UTR: nts. 5937-6416

In plasmid pTL13 the various functional elements are located at the following positions, whereby reference is made to the nucleotide sequence of SEQ ID NO: 23:
Ptight promoter (TREmod+ minimal PCMV): nts. 2-318
Ad5 E1A: nts. 400-1385
Ad5 E1B promoter: nts. 1477-1553
Ad E1B 55K: nts. 1859-3349
UBE2I intron: nts. 3359-3512
Ad5 E1B 84R C-terminus: nts. 3513-3530
UBE2I 3' UTR: nts. 3531-4008

In an embodiment the nucleic acid construct according to the present invention will also contain a 3' UTR elements enabling processing of the E1B RNA including cleavage and polyadenylation. The nature of this element is not critical to the present invention, except that such an element has to be present to allow for RNA processing. In a further preferred embodiment the downstream RNA processing element from the UBE2I gene is used.

It is within the present invention that the nucleic acid construct is present as either a DNA molecule or an RNA molecule.

In connection with the cells and cell lines of the present invention a preferred embodiment thereof are amniocytic cells or amniocytes. The term "amniocytes" or aminocytic cells, both terms are used in an interchangeable manner herein, means herein all cells present in the amniotic fluid and obtained by amniocentesis. They are derived either from the amnion, from the fetal tissue, which is in contact with the amniotic fluid, e.g. from fetal skin or urine. Three main classes of amniocytes are distinguished on the basis of morphological criteria, fibroblast-like cells (F cells), epitheloid cells (E cells) and amniotic fluid cells (AF cells) (Hoehn et al., Pediat. Res. 8, 746-754, 1974), but additional cell types may be present. Each of these three main classes of amniocytes is an amniocytic cell into which a nucleic acid construct of the present invention may be introduced. In accordance therewith an amniocytic cell of the present invention is any cell type that is present in amniotic fluid such as an F cell, an E cell and/or an AF cell.

Cells referred to as "primary cells" are those, which are obtained by removal from an organism, placed into a cell culture dish and can then be cultivated and propagated by cell passaging for a limited lifetime until they enter senescence.

In an embodiment, at least one nucleic acid construct of the present invention is introduced by transfection into primary amniocytes before they have entered senescence, enabling expression of the adenoviral E1A and E1B gene products, thus leading, following chromosomal integration of the E1A and E1B encoding nucleic acid, to immortalization of primary amniocytes and to the establishment of immortalized amniocyte cell lines. The term transfection is used to indicate the introduction of nucleic acids into the cells by any means, whether using for example chemical methods (e.g. by lipofection or by polyethylenimine (PEI)-mediated transfection), physical methods (e.g. by electroporation) or biological methods (e.g. by using a viral vector).

The "at least one nucleic acid" is preferably used in the form of one or several DNA expression units, which are present either on bacterial plasmid vectors or on viral vectors including for example naturally integrating vectors such as retrovirus or lentivirus vectors. The term "at least one nucleic acid" refers to the fact that the expression units coding for the different E1 proteins may be contained on one or of more than one vector.

It is within the present invention that further expression units coding for additional viral, in particular adenoviral, or non-viral functions, such as for example the non-structural adenoviral E2A, E2B and/or E4 proteins, structural adenoviral proteins such as fiber, pIX, or penton base or for recombinases such as Cre or Flp recombinase may form part of the nucleic acid construct of the present invention. However, it is also within the present invention that these further expression units are contained in one or several separate vectors. Such one or several vectors may be plasmids or viruses.

It is also possible to introduce these functions in a consecutive manner. Suitable techniques and processes for the production and, where appropriate, mutagenesis of nucleic acids and for gene expression and protein analysis are available to the skilled worker (see, for example, Sambrook, J. et al., Molecular Cloning: A Laboratory Manual, Cold Spring Harbor Laboratory Press (1989); Glover, D. M., DNA cloning: A practical approach, vol. II: Expression Systems, IRL Press (1995); Ausubel et al., Short protocols in molecular biology, John Wiley & Sons (1999); Rees, A. R. et al., Protein engineering: A practical approach, IRL press (1993)).

Methods for the preparation of the nucleic acid constructs of the present invention are as such known to a person skilled in the art. Such methods include, among others, cloning methods and methods of chemical synthesis.

In connection with the aspect of the present invention which is related to a method for the production of a gene transfer vector, preferably an adenoviral gene transfer vector, or an adenovirus mutant comprising the step of cultivating a cell of the invention comprising a nucleic acid construct of the invention and/or a cell line of the invention comprising a nucleic acid construct the cell and cell line, respectively, comprises a further nucleotide sequence, wherein the further nucleotide sequence is the gene transfer vector or the adenovirus mutant. Preferably, the gene transfer vector or the adenovirus mutant are expressed and/or produced in a or the host cell. The further nucleotide sequence comprising the nucleic acid sequence of the gene transfer vector or the adenovirus mutant may be part of or be comprised by the expression unit for the expression of E1B and/or may be part of or comprised by the expression unit for the expression of E1A. Alternatively, the further nucleotide sequence coding for the gene transfer vector or the adenovirus mutant is part of a vector which is different from the nucleic acid construct of the invention and, respectively, a vector containing the nucleic acid construct of the invention. In an embodiment, the vector comprising the further nucleotide sequence coding for the gene transfer vector or the adenovirus mutant is not covalently linked to the nucleic acid construct of the invention and, respectively, a vector containing the nucleic acid construct of the invention. In a further embodiment the vector comprises a selection marker for, preferably, allowing selecting and maintaining, respectively, only those cells which contain the vector comprising the further nucleotide sequence coding for the gene transfer vector or the adenovirus mutant, particularly in case of production of a gene transfer vector such as, among others, an AAV vector.

In an embodiment of this aspect of the present invention the method is one for the production of ΔE1Ad vectors in the immortalized cell lines of the present invention. The E1A and E1B expressing cells such as those generated by immortalization using plasmid pSTK146 UBE2I, are preferably infected with ΔE1Ad vectors using between 3 and 20 infectious units per cell (MOI (multiplicity of infection)=3 to 20). After about 36 to 72 hours, the cells show a cytopathic effect. The cells are harvested by standard protocols well known to the expert. Adenoviral vectors can be purified from cell extracts or supernatant by CsCl density gradient centrifugation or by chromatographic processes.

In a further embodiment of this aspect of the present invention the method is one for the production of second-generation Ad vectors. To produce second-generation adenoviral vectors, the functions which the vector itself does not express, due to inactivation and/or deletion, are provided by the cell line according to the present invention Amniocytic cell lines stably express E1A and E1B are further modified by transfection of expression cassettes which express the gene products coding for one or more other adenoviral functions. For example, to produce a second-generation adenoviral vector which has, in addition to the deletion of the E1A and E1B genes, also a deletion of an E2A, E2B and/or E4 gene, the appropriate gene or genes is/are introduced by transfection together with a selection antibiotic into the E1A- and E1B-expressing amniocytic cell line. Cell clones which, in addition to the expression of E1A and E1B functions, also express E2A, E2B and/or E4 functions can then be used to produce the particular second-generation vector. The E2 and/or E4 genes are usually under the transcriptional control of a heterologous promoter, which either is constitutively active or can be regulated for example using an inducible gene expression system. In these cells, Ad vectors are produced by infecting the cell lines with second-generation Ad vectors using between 3 and 20 infectious units per cell (MOI (multiplicity of infection)=3 to 20). After about 36 to 72 hours, the cells show a cytopathic effect. The cells are harvested by standard protocols well known to the expert. Adenoviral vectors can be purified from cell extracts or supernatant by CsCl density gradient centrifugation or by chromatographic processes.

In connection with the aspect of the present invention which is related to the use of a cell of the invention preferably containing a construct of the invention and/or of a cell line of the invention preferably containing a construct of the invention for producing a protein, the cell and cell line, respectively, comprises a further nucleotide sequence coding for the protein. Preferably, the further nucleotide sequence is expressed in a host cell. The further nucleotide sequence coding for the protein may be part of or comprised by the expression unit for the expression of E1B and/or may be part of or comprised by the expression unit for the expression of E1A. Alternatively, the further nucleotide sequence coding for the protein is part of a vector which is different from the nucleic acid construct of the invention and, respectively, a vector containing the nucleic acid construct of the invention. In an embodiment, the vector comprising the further nucleotide sequence coding for the protein is not covalently linked to the nucleic acid construct of the invention and, respectively, a vector containing the nucleic acid construct of the invention. In a further embodiment the vector comprises a selection marker for, preferably, allowing selecting and maintaining, respectively, only those cells which contain the vector comprising the further nucleotide sequence coding for the protein. The vector comprising the further nucleotide sequence coding for the protein is preferably a plasmid or a virus. The same considerations equally apply to the method of the invention for the production of a protein which comprises the cultivation of a cell of the invention or of a cell line of the invention each comprising a nucleic acid construct of the invention.

A protein in connection with these and each and any other aspects of the present invention is preferably a polypeptide consisting of one or several chains of amino acids that can be used for therapeutic purposes, for prophylactic purposes, such as a vaccine, or for diagnostic purposes. For protein production, one or several nucleic acids coding for the protein of interest are introduced as an expression unit into the E1A and E1B-expressing immortalized amniocytic cell line such as one of the present invention generated by immortalization with the pSTK146 UB2I nucleic acid construct by transfection. Such expression unit preferably comprises as minimal elements a nucleic acid coding for the particular protein, which is operatively linked to a constitutive or inducible promoter, and a 3'UTR with the mRNA processing functions. In general, identification of cell clones, having chromosomally integrated the nucleic acid coding for the protein of interest, is facilitated by either cotransfection with a second plasmid expressing a selectable marker or by using a plasmid that contains both the expression unit expressing the protein of interest and the selectable marker. A typical example for a selectable marker is a neo gene, coding for an aminoglycoside phosphotransferase and conferring resistance to the aminoglycoside neomycin or the antibiotic G418 (Davies et al., 1980). Another example of a selectable marker that can be used within the scope of the present invention is the gene coding for puromycin N-acetyl-transferase (PAC) that confers resistance to the aminonucleoside antibiotic Puromycin. Again other selectable markers well known to the person skilled in the art can be used instead of the two mentioned examples. But also other methods can be used for introduction of an expression unit coding for the protein of interest into into the amniotic cell line of the present invention, including the use of integrating vector systems such a retroviral or lentiviral vectors, in this particular case even making the use of a selectable marker in most cases unnecessary. The protein produced in the amniocytic cell lines is then harvested either from the cell extract or from the supernatant using standard methods that includes techniques of centrifugation, different solubility and chromatography such as, e.g., ion exchange, affinity or size exclusion chromatography and other procedures that are will known the expert. In a preferred embodiment the protein produced in accordance with the present invention is selected from the group comprising antibodies, including those that are used for the treatment of patients with cancer, those that are used for treating inflammatory diseases such as, or those that are used to treat infectious diseases; blood factors, including coagulation factors that are used for the treatment of patients with inherited or acquired hemophilias, and including erythropoietins used for the treatment of patients with anemia; interferons and interleukins, colony stimulating factors and growth factors, hormones and enzymes.

In a preferred embodiment the protein produced in accordance with the present invention is selected from the group comprising antibodies or antibody fragments, including those that are used for the treatment of patients with cancer, infectious diseases, degenerative diseases, allergic diseases, genetic diseases, autoimmune diseases, inflammatory diseases such as arthritis or psoriasis, cardiovascular diseases and transplant rejection. Examples include antibodies targeting glycoprotein IIb/IIIa (example: abciximab), targeting TNF alpha signalling (examples: adalimumab, certolizumab pegol, infliximab), targeting CD52 (example: alemtuzumab), targeting CD25 (examples: basiliximab, daclizumab), targeting B-cell activating factor (example: belimumab), targeting VEGF (examples: bevacizumab, ranibizumab), targeting CD30 (example: brentuximab vedotin), targeting IL-1 beta (example: canakinumab), targeting EGFR (examples: cetuximab, panitumumab), targeting RANK Ligand inhibitor (example: denosumab), targeting complement system proteins (example: eculizumab), targeting CD11a (example: efalizumab), targeting CD33 (example: gemtuzumab), targeting TNF alpha (example: golimumab), targeting CD20 (examples: ibritumomab tiuxetan, ofatumumab, rituximab, tositumomab), targeting CTLA-4 (example: ipilimumab), targeting CD3 (example: muromonab-CD3), targeting integrins (example: natalizumab), targeting IgE (example: omalizumab), targeting viral proteins (example: palivizumab), targeting interleukin receptors (examples: toxilizumab, atlizumab), targeting ErbB2 (example: trastuzumab).

In another preferred embodiment the protein produced in accordance with the present invention is selected from the group of enzymes that are preferably used for replacing missing enzymes in genetic disorders (frequently belonging to the so-called storage disorders). Examples are glucocerebrosidase for the treatment of M. Gaucher, iduronidase for the treatment of MPS type I, iduronate-2-sulfatase for the treatment of MPS type II, galsulfase for the treatment of MPS Typ Vi, alpha-glukosidase for the treatment of M. Pompe, agalsidase beta for the treatment of Fabry disease.

In other preferred embodiments the protein produced in accordance with the present invention is an erythropoietin (currently mainly used for the treatment of anemia), alpha-interferon (currently mainly used for the treatment of chronic hepatitis B, hepatitis C or in anti-cancer therapy), beta-interferon (currently mainly used for the treatment of multiple sclerosis and virus disease), gamma-interferon (currently mainly used in anti-cancer therapy), colony-stimulating factors G-CSF, M-CSF, GM-CSF and MEG-CSF (an example for the use of G-CSF is neutropenia, observed in patients under chemotherapy or bone marrow transplantion) or for stem cell mobilisation from the bone marrow in cases of stem cell transplantation; an example of the use GM-CSF is immunostimulation and treatment of neutropenia).

In another preferred embodiment the proteinproduced in accordance with the present invention is selected from the selected from the group of blood factors including coagulation factors, preferably those which are used in the treatment of patients with inherited or acquired hemophilias. Examples are blood coagulation factors VII, VIII, IX or von Willebrand Factor, that primarily are used in genetic disorders of blood coagulation, in eluding hemophilias A (F VIII deficiency), B (F IX deficiency) and von von Willebrand Disease (vWF deficiency, respectively. Plasminogen activators such as tissue plasminogen activator (tPA) are included in this group.

In another preferred embodiment the protein produced in accordance with the present invention is selected from the groups of hormones and growth factors. Examples for this group are human growth hormone (GH) that is used to treat patients with growth delay and short stature, and insulin that is used for the treatment of diabetes.

In another preferred embodiment the protein produced in accordance with the present invention is selected from the groups of chemokines including interleukins, interferones and colony stimulating factors. An example for this group is Interleukin-2 (IL-2) that is used for the treatment of renal cell carcinoma.

Again in another preferred embodiment the protein produced in accordance with the present invention is selected from the group of fusion proteins. An example for a fusion protein is etancercept, consisting of the extracellular ligand-binding domain of the human RNF receptor 2 (TNFR2/p75) and the Fc-part of IgG1-antibody.

The following is a table summarizing the various SEQ ID Nos: as used herein also indicating what the function of the respective sequences are and what kind of function, respectively, they encode.

SEQ ID NO: 1: nucleotide sequence coding for E1B
SEQ ID NO: 2: nucleotide sequence coding for E1A
SEQ ID NO: 3: 3'UTR of SV40 as contained in pSTK 146
SEQ ID NO: 4: intron of SV40 as contained in pSTK 146
SEQ ID NO: 5: nucleotide sequence of a nucleic acid construct of the instant application
SEQ ID NO: 6: nucleotide sequence of a nucleic acid construct of the instant application
SEQ ID NO: 7: nucleotide sequence of an expression unit for the expression of E1B
SEQ ID NO: 8: nucleotide sequence of an expression unit for the expression of E1A
SEQ ID NO: 9: nucleotide sequence of a nucleic acid construct of the present invention (pSTK146 UBE2I)
SEQ ID NO: 10: nucleotide sequence of the UBE2I intron
SEQ ID NO: 11: nucleotide sequence of the UBE2I splice donor site
SEQ ID NO: 12: nucleotide sequence of the UBE2I splice acceptor site
SEQ ID NO: 13: nucleotide sequence of the intron including a splice donor site and a splice acceptor site as used in a nucleic acid construct of the present invention
SEQ ID NO: 14: nucleotide sequence of the 3' UTR of the expression unit for the expression of E1B
SEQ ID NO: 15: nucleotide sequence of a nucleic acid construct of the present invention (pTL13)
SEQ ID NO: 16: amino acid sequence of E1B 55K
SEQ ID NO: 17: nucleotide sequence coding for E1B 55K
SEQ ID NO: 18: amino acid sequence of E1B 19K
SEQ ID NO: 19: nucleotide sequence coding for E1B 19K
SEQ ID NO: 20: amino acid sequence of E1B84R
SEQ ID NO: 21: nucleotide sequence coding for E1B84R
SEQ ID NO: 22: nucleotide sequence of plasmid pSTK146 UBE ΔE1B 84R/pIX
SEQ ID NO: 23: nucleotide sequence of plasmid pTL13
SEQ ID NO: 24: nucleotide sequence of plasmid pSTK146
SEQ ID NO: 25: nucleotide sequence of the 3'UTR of the human gene UBE2I
SEQ ID NO: 26: oligonucleotide #73
SEQ ID NO: 27: oligonucleotide #74
SEQ ID NO: 28: oligonucleotide #75
SEQ ID NO: 29: oligonucleotide #76
SEQ ID NO: 30: oligonucleotide #59
SEQ ID NO: 31: oligonucleotide #60

The present invention is further illustrated by the figures, examples and the sequence listing from which further features, embodiments and advantages may be taken, wherein FIG. 1 illustrates four embodiments of the nucleic acid construct of the present invention. The design of 4 different nucleic constructs of the present invention is shown. Expression of the E1A proteins is controlled by the murine PGK promoter (P-mpgk) (a, b) or by a heterologous promoter (c, d). Expression of the E1B proteins is controlled by the natural E1B promoter (P-E1B) or by a heterologous promoter (P-Y). The E1B coding sequence is followed by a splice donor site (SD), and intron and a splice acceptor site (SA), all derived from the UBE2I gene. In a) and c) this is followed by part of the non-coding part of the pIX gene, allowing for expression of the E1B 84R protein. The 3'UTR of the UBE2I gene is present in all four constructs shown in this figure. FIG. 1a) is a schematic representation of SEQ ID No 5 and FIG. 1b) is a schematic representation of SEQ ID No 6;

FIG. 2 illustrates two embodiments of nucleic acid construct of the present invention, in which E1A is under inducible promoter control. The design of 2 different nucleic constructs of the present invention is shown. Expression of the E1A proteins is controlled by the Tet-inducible promoter PTight. Expression of the E1B proteins is controlled by the natural E1B promoter (P-E1B. The E1B coding sequence is followed by a splice donor site (SD), and intron and a splice acceptor site (SA), all derived from the UBE2I gene. In a) this is followed by part of the non-coding part of the pIX gene, allowing for expression of the E1B 84R protein. The 3'UTR of the UBE2I gene is present in both constructs shown in this figure. FIG. 2a) is a schematic representation (without the plasmid backbone) of the essential elements in SEQ ID No 23;

Figure 5:
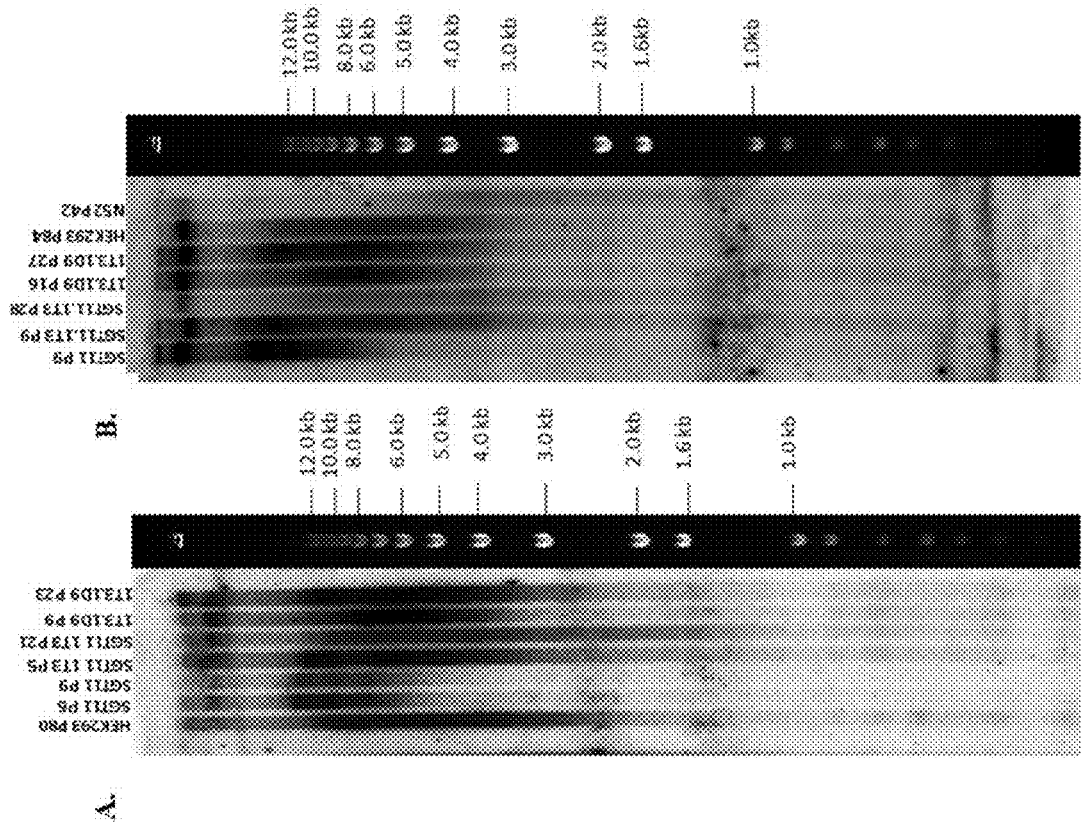
Figure 6:
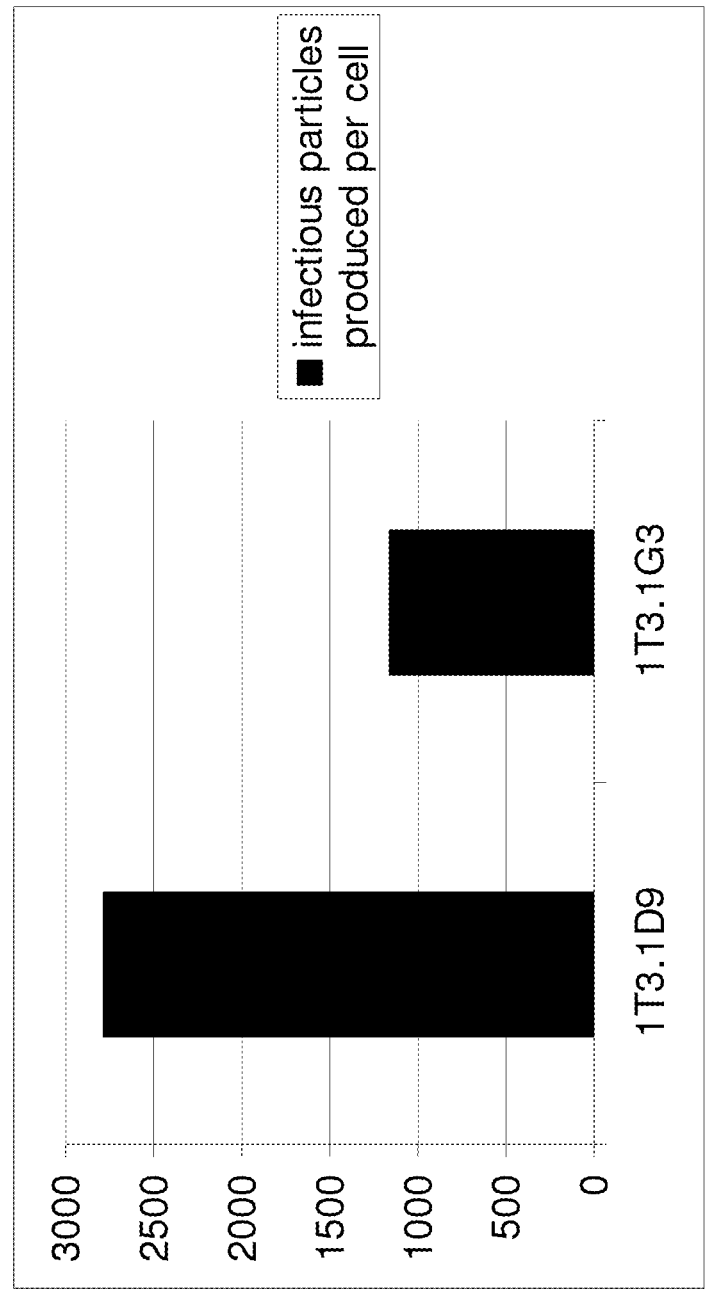

FIG. 5 shows Southern Blot analyses of mean telomere restriction fraction (TRF). The E1-transformed established HEK293 cells were used for comparison. On the left (A), TRF of primary human amniocytes (SGT11 P6 and P9) is shown in comparison with E1-transformed, polyclonal (SGT11 1T3 P5 and P21) and monoclonal (1T3.D9 P9 and P23) human amniocytes. On the right (B), the same cell lines and N52.E6 were analysed; and FIG. 6 shows the production of infectious particles of a ΔE1 Ad vector expressing EGFP (Ad1stGFP) in SGT11 1T3.1D9 and in SGT11 1T3.1G3 cells.

C. EXAMPLES

Example 1

Cloning of the Ad5 E1 Expressing Construct pSTK146UBE2I

Cloning Strategy

According to previous results human primary amniocytes can be transformed by E1 proteins of hAd5 (Schiedner et al., 2000). The E1 expressing construct pSTK146 of the prior art used in these experiments contains non-coding SV40 sequence elements including intron and 3' UTR that are often found in many transcription cassettes enhancing gene expression. An intron at the 3' end of the E1B 55K coding sequence including a splice acceptor is necessary for splicing of the MB mRNAs and efficient expression of E1B 55K protein. An embodiment of the nucleic acid construct of the present invention which his referred to herein as pSTK146 UBE2I, was generated, replacing the SV40 intron and 3' UTR by a short intron, including splice donor and splice acceptor and a 3' UTR of the human gene UBE2I (NCBI Reference Sequence: NT_010393.16, SEQ IC NO: 25. Additionally, a short sequence of the pIX gene was inserted which allows for expression of the minor E1B 84R protein. For an enhanced expression of E1B 84R and a reduced homology to corresponding Ad5 sequences, the E1B 84R-encoding sequence was codon-optimized. The latter measure is particularly useful in case the cell line containing the nucleic acid construct of the present invention is used for production of ΔE1Ad vectors. To further reduce sequence overlaps between transgene expression cassettes of the ΔE1 Ad vectors and the Ad5 sequences of E1-transformed cell lines the 3' UTR of SV40 including the polyadenylation site was replaced by a human 3' UTR of the UBE2I gene.

Actual Cloning

Figure 1:
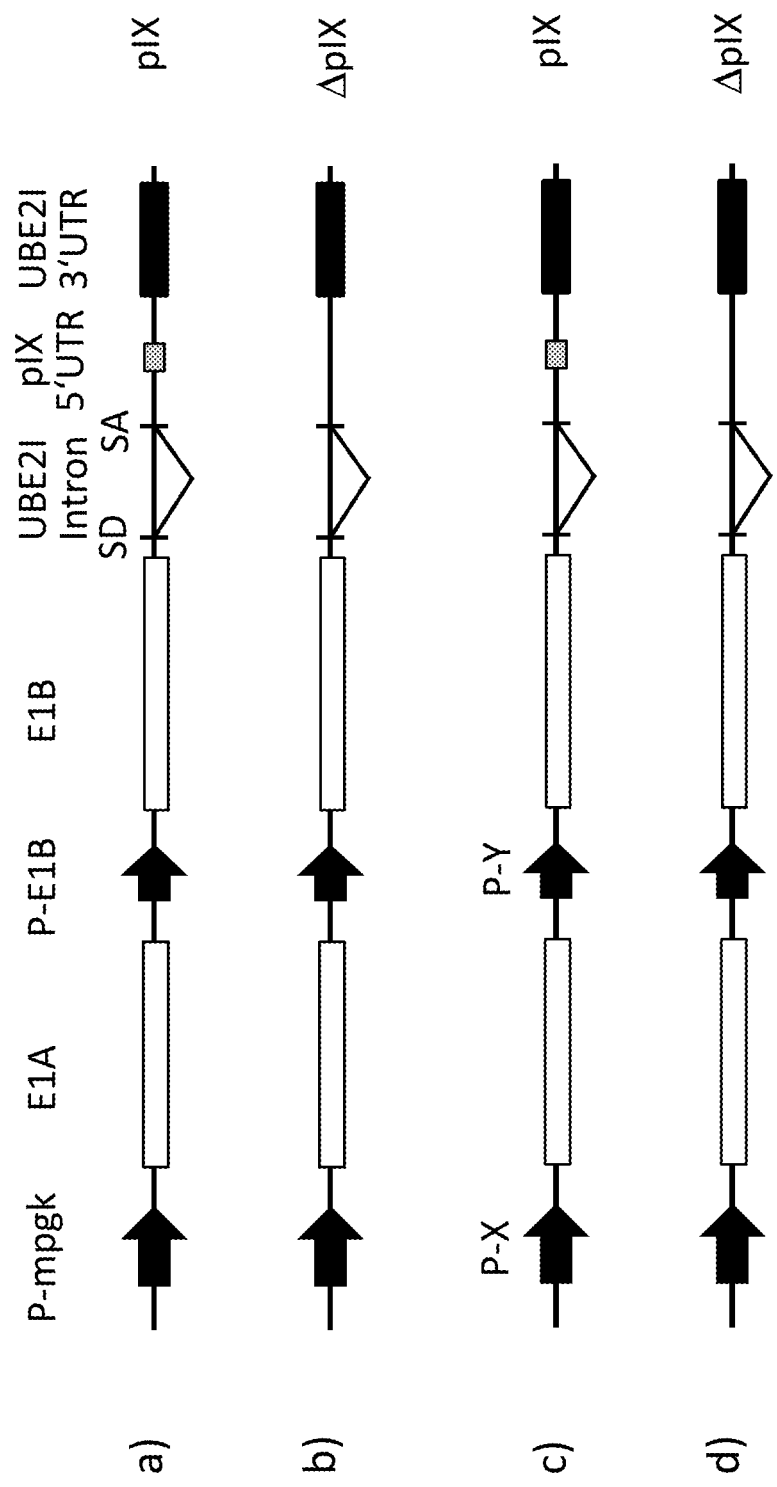

Starting from plasmid pBKSII E1B containing the E1B promoter, E1B coding sequence and SV40 sequences (intron and 3' UTR) a site-directed mutagenesis was performed to remove the splice donor site at nt. 3510 of Ad5 and to introduce a NdeI restriction site within the plasmid. The resulting plasmid pBKSII E1B QC NdeI was digested with BamHI and NdeI to release a 1 kb fragment thereby removing all SV40 sequences. The human UBE2I intron was obtained by polymerase chain reaction (PCR) using genomic DNA isolated from low passage human N52.E6 cells (Schiedner et al., 2000) and oligonucleotides #73 (5'-gttcag CATATGcaggtacggggcctccgcctctg-3' (SEQ ID NO: 26) and #74 (5'-TCAAGGTGGGGGAGGGTtctgtgccagaga-caaaaacacaagac-3'(SEQ ID NO: 27). The PCR product called "PCR intron" is flanked by a NdeI site (underlined) and codon-optimized Ad5 sequences (nt. 3595 to nt. 3612) encoding for the C-terminal part of E1B 84R at the 5' or 3 'end, respectively. The 3' UTR of UBE2I was isolated using oligonucleotides #75 (5'-gaACCCTCCTCCACCTTGAAT-TGCCCGTTTCCATACAGGGTC-3' (SEQ ID NO: 28) and #76 (5'-ctggatccGCGGTGGGGCTGCAGGTG-3'(SEQ ID NO: 29)) resulting in the PCR product "PCR 3' UTR" which is flanked by the same Ad5 sequences (nt. 3595 to nt. 3612) as mentioned above and a BamHI restriction site (underlined) at the 5' or 3' end, respectively. The overlapping Ad5 sequences at the 3' end of "PCR intron" and at the 5' end "PCR 3 UTR" allowed to fuse these two PCR products thereby using oligonucleotides #73 and #76. The resulting fusion PCR fragment flanked by NdeI and BamHI was then inserted between the NdeI and BamHI sites of pBSK E1B QC NdeI resulting in pBSK E1B UBE2I. To generate pSTK146 UBE2I the BglII/BamHI fragment from pBSK E1B UBE2I containing the UBE2I intron, codon-optimized C-terminal part of E1B 84R and UBE2I 3' UTR was subcloned between the BglII and BamHI sites of pSTK146. The resulting plasmid was named pSTK146UBE2I (Sequence ID NO 9) and is also depicted in FIG. 1a).

Example 2

Western Blot Analysis to Detect Steady-State Levels of E1 Proteins

To determine expression levels of the E1B 55K protein after transient transfection using various E1B 55K expressing nucleic acid constructs $1 \times 10^6$ Hela cells were seeded in 6 cm dishes. The next day the cells were washed with phosphate-buffered saline (PBS) and fresh medium was added. The cells were transfected with 3 µg of plasmid pSTK146 (expressing both E1A and E1B) and plasmid pBSKII E1B (expressing only E1B from the natural E1B promoter), pBSKII E1B UBE2I (expressing E1B from the natural E1B promoter and containing the UBE2I elements) and plasmid pSTK146 UBE2I using polyethylenimine (PEI) as transfection reagent. After 48 hours the cells were washed with PBS, detached with 50 mM EDTA in PBS and pelleted by centrifugation. Cell pellets were lysed with 200 µl RIPA lysis buffer (40 mM Tris/HCL, pH 8, 150 mM NaCl, 5 mM EDTA, 1% (v/v) Nonidet P-40, 0.1% (w/v) SDS, 0.5% (w/v) sodium desoxycholate) for 30 minutes on ice. After repeated freezing and thawing the cell debris was removed by centrifugation, and the protein concentration was determined (Bio-Rad protein assay). Fifty µg of whole cell extract was analysed by 10% SDS-PAGE and immunoblotting. The E1B 55K protein was detected using the E1B 55K-specific 2A6 antibody.

Figure 4:
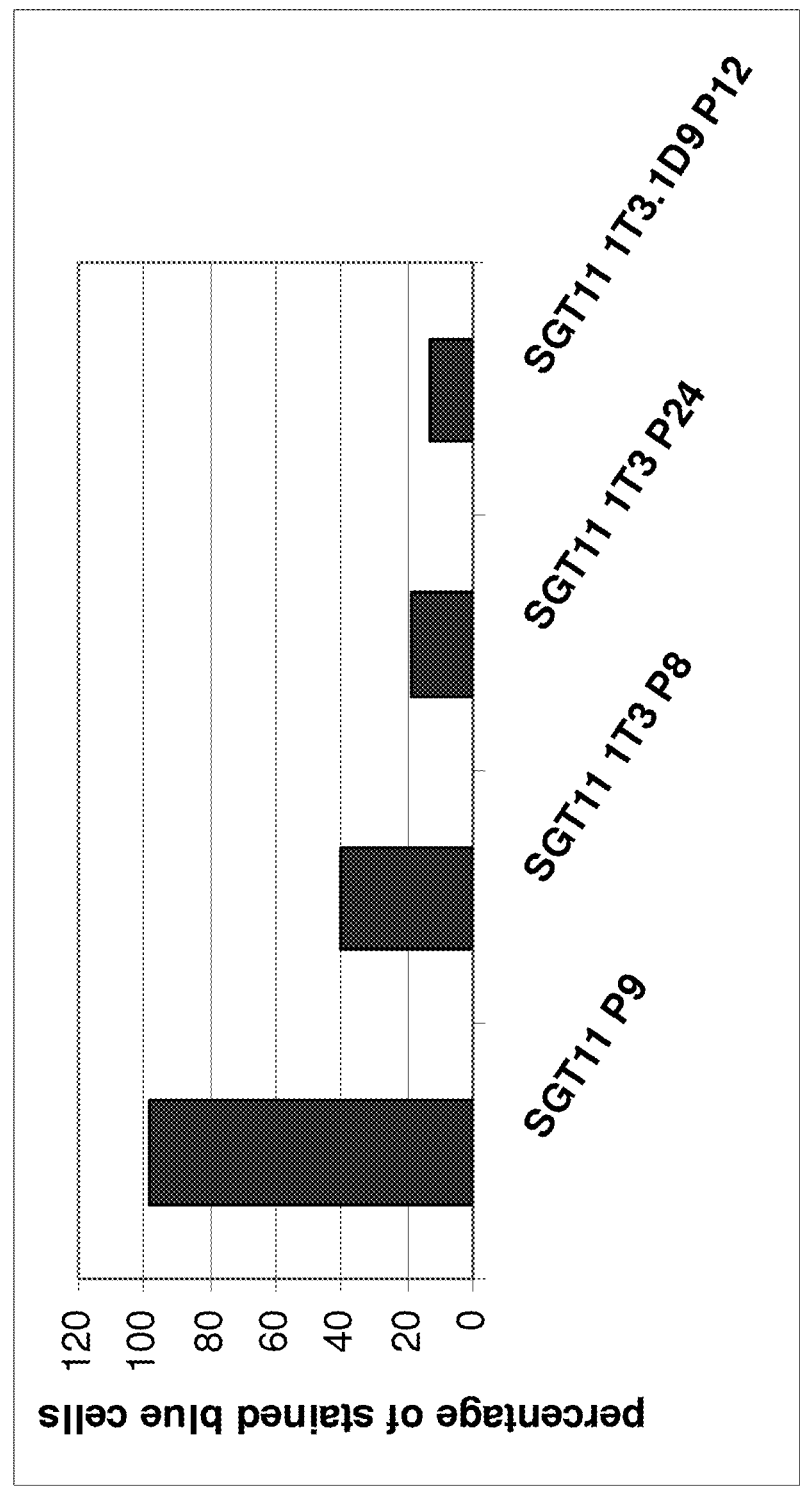
FIG. 4 shows analysis of SA β-galactosidase expression in primary and E1-immortalized amniocytes.

Expression of the E1B 55K protein after transfection of pBSKII E1B UBE2I and pSTK146 UBE2I was approximately 10-fold higher than after transfection of pBSKII E1B and of pSTK146 as shown in FIG. 4. Unexpectably, following transfection of pBSKII E1B and of pSTK146 a faster migrating E1B form was detected with a molecular weight of about 37 kDa (designated E1B 37K) that was not detectable in transfections of pSTK146 UBE2I.

Example 3

Determination of Aberrant Splicing of E1B mRNA Transcripts in pSTK146-Transfected Cells Western blot analysis of pSTK146-transfected cells by the N-terminal binding E1B-specific antibody 2A6 showed—in addition to E1B 55K—a faster migrating E1B protein named E1B 37K. To test at the mRNA level, if the E1B 37K protein resulted from aberrant splicing events, total RNA from pSTK146-transfected Hela cells was extracted with Trizol Reagent and further purified using Phase Lock Gel tubes (PLG, Eppendorf) and RNeasy Mini Kit (Qiagen) including DNAse treatment according to the manufacturers' instructions. Complementary DNA (cDNA) was synthesised with the SuperScript™ III First-Strand Synthesis System (Invitrogen, Carlsbad, USA) as described by manufacturer's protocol and RNA was reverse transcribed using an oligo-dT primer. PCR amplification of cDNA was performed with Taq Polymerase (NEB) using the forward oligonudeoxycleotide #59 (5'-CTGAACTGTATCCAGAACTGAG-3'(SEQ ID NO: 30)), which binds 3' to the splice donor (SD)1 that is normally used (located at nucleotide (nt.) sequence 2,255 of Ad5 or nt. 4,503 of pSTK146) and the SV40-specific, reverse oligonucleotide #60 (5'-ACTGCTCCCATTCATCA-GTTC-3'(SEQ ID NO: 31)), which binds 3' to SV40 splice acceptor (SA). The amplified cDNAs were gel-purified and their 3' overhangs were removed by T4-DNA Polymerase (NEB). The cDNAs were then inserted into the EcoRV site of the cloning vector pBluescript II SK, and sequenced (Entelechon GmbH, Regensburg, Germany).

Sequence analysis of E1B mRNA transcripts revealed aberrant splicing using an SD (nt. 2,324 of Ad5 or nt. 4,572 of pSTK146) 69 nt. downstream of SD1 and the SA of the SV40 3' UTR (nt. 5,832). The usage of the splice donor SD2, which is usually used for splicing of E1B 55K encoding mRNA transcripts, could not be detected. The resulting E1B 37K protein only shares the first 102 amino acids with E1B 55K. For efficient transformation, however, various motifs in the central part and C-terminus of E1B 55K are required. By introducing an intron and an 3'UTR region from UBE2I gene, cryptic splicing may be inhibited leading to the expression of a full length E1B 55K protein harbouring all sequence motifs contributing to transformation (Blackford et al., 2009, Endter et al., 2001, Schreiner et al., 2011). Taken together, following cell transfection with plasmid pSTK146, only a very small amount of the E1B 55K protein was detected, rather an abberrant "E1B 37 K" protein was found that results from aberrant splicing as shown by sequence analysis following RT-PCR.

Example 4

Transfection of Human Amniocytes with Plasmids pSTK146 and pSTK146 UBE2I

Transfection of human amniocytes essentially followed the procedure as described in Schiedner et al., 2000, and in EP00979539 with some modifications as detailed below.
Culture of Amniocytes Samples of amniotic fluid containing primary cells obtained by diagnostic amniocenteses, were added to cell culture medium in plastic culture dishes Amniotic fluid cells generally began to attach and proliferate within 2-4 days after seeding. Primary cell populations were cultured in adherent culture in plastic cell culture dishes initially in Ham's F10 medium supplemented with 10% fetal bovine serum, 4 mM glutamine and 2% Ultroser. Later, when the cells had been expanded to two 15 cm cell culture dishes, they were adapted during two passaging steps to OptiPro medium (Gibco) supplemented with 2% Ultroser (Cytogen) and 2% Glutamax (Gibco), in a first step to 50% OptiPro medium and in a second step to 100% OptiPro medium. Culture medium was changed every 3-4 days. At a visual confluency of 70-90%, primary amniocytes were detached with TrypLE Select (Gibco) and expanded to larger vessels or split by a factor of four. Starting in the fourth passage after seeding, several vials of cells were frozen in every passage (freezing procedure described below). The culture was maintained until over 50% of cells had acquired the senecent phenotype, characterized by enlargement and flattening of cells as well as arrested cell division. This change was generally observed between passage 7 and 11, corresponding to 30-38 population doublings.
Freezing and Storage of Cell Stocks For long-term storage of primary cells, cells were detached with TrypLE Select, collected and separated from culture medium by centrifugation. They were resuspended in fresh culture medium containing 5% cell culture grade dimethylsulfoxid (DMSO, Sigma) at a cell density of $1 \times 10^6$ to $1 \times 10^7$ cells per milliliter. The suspension was filled in vials for storage in liquid nitrogen (Nalgene). The tubes were placed in a Nalgene freezing device containing isopropanol as a cooling agent; the device was stored overnight at −80° C., resulting in a cooling rate of about 1K per minute. The frozen vials were then placed in the gaseous phase of a liquid nitrogen container for long-term storage.

The same freezing procedure was used also for cell clones and cell lines derived from primary amniocytes.
Preparation of Transfection Complexes, Transfection of Amniocytes Transfection was performed on primary amniocytes between passage 7 and 9, corresponding to PD 30 to 35, shortly before the onset of senescence.

Materials used:

Plasmid pSTK146 UBE2I DNA in Tris-EDTA buffer, pH 7.5, following linearization with restriction enzyme BspHI according to standard procedures. BspHI cleaves in the plasmid backbone, not within the E1A/E1B expression cassettes.

Solution of linear polyethyleneimine (PEI), 7.5 mM (0.32 µg/µl; PEI nitrogen molarity: 43 g/mol), pH 7.0, sterile filtered (0.2 µm)

Sodium chloride (NaCl) solution, 150 mM, sterile filtered (0.2 µm)

For each culture dish to be transfected, 2 µg of linearized plasmid DNA and 36 µl of PEI solution were separately diluted ad 250 µl with NaCl solution. Each PEI dilution was added to one DNA dilution, resulting in an N/P (nitrogen/phosphorous) ratio of 45. Preparations were mixed and incubated at room temperature for 15 to 20 minutes to allow for the formation of PEI-DNA complexes. Primary amniocytes, seeded in 6 cm culture dishes on the previous day at a visual density of 50-70%, were washed with PBS and supplied with fresh culture medium. Each transfection complex was added to one prepared dish.

Culture after Transfection

Twentyfour hours after transfection, cells were detached from culture dishes with TrypLE Select (Gibco) and transferred to 14 cm dishes. Over a period of 3 to 6 weeks, medium was changed every 3 to 4 days, or cells on one culture dish were passaged to two dishes, if cells reached a visual confluency over 90%. During this period, dishes were observed daily under 2.5-fold magnification to screen for emerging foci of transformed cells.

Harvesting and Expansion of Transformed Cell Clones

Three to six weeks after transfection, foci of transformed cells became visible among the primary amniocytes. Transformants were recognized by their distinctive morphology, small cell size and rapid growth among very large and non-dividing senescent primary cells. The round foci were removed mechanically from the culture surface by scraping and aspiration with a sterile pipette tip and seeded in a culture well. Each harvested clone was expanded to larger culture vessels for three passages before a first cell stock was frozen.

For clarity, the term "clone" or "cell clone" and its plural forms are preferably used herein to describe proliferating cells derived from isolated single cell foci that are generated after transfection with the E1-expressing plasmids. These single foci, as described above are removed from the cell culture dish by aspiration and seeded in individual cell culture dishes. At this stage they are assumed to be polyclonal, since multiple clones are derived from the same cell culture dish and it cannot be excluded that a clone consists of cells derived from more than one integration and immortalization event. The term "cell line" and its plural form are preferably used herein to describe immortalized and permanently proliferating cells obtained following single cell cloning so that they can be considered monoclonal.

Use of Different Ad5 E1 Expressing Plasmids pSTK146 and pSTK146UBE2I for Transfection and Generation of Immortalized Cell Lines The described transfection procedure was performed using two different E1-expressing constructs: pSTK146 and the pSTK146 UBE2I. Both transfections resulted in successful generation of foci consisting of small and rapidly proliferating cells. However, significant differences were observed in the long-term stability of clones in culture.

During the passages following isolation, a portion of clones underwent crisis characterized by morphological changes including strong increase in size and flattening, slow cell division and ultimately cessation of growth, and in part signs of cell death. The clones transformed with pSTK146 were much more susceptible to these changes: At least 60% of each clone batch (78% over all experiments) ceased to grow during the early phase of culture (polyclonal passage 1 to 4, PD<55). Subsequently, only seven of 14 clones selected for good growth and adenovirus vector productivity kept proliferating beyond polyclonal passage 10 (corresponding to a total of approximately 65 PDs after seeding of the primary cells), and none survived beyond polyclonal passage 13 (75 PDs).

Clones transformed with the pSTK146 UBE2I construct, however, survived the early passages at a much higher rate (average loss 29% up to passage 4), and only few clones entered crisis at a later point. Eight clones selected for high productivity were kept in culture up to polyclonal passage 23 or higher (100 PDs) and were considered for the generation of monoclonal cell lines.

Further details of the transformation experiments are summarized in the following Tables 1 and 2.

TABLE 1

Results following transfection of primary amniocytes with pSTK146 until polyclonal passage 4

| Passage no. | Culture vessel | no. of proliferating cell clones | % of isolated cell clones |
|---|---|---|---|
| 1 | 24-well dish | 473 | |
| 2 | 6-well dish | 226 | 48 |
| 3 | 9.2 cm dish | 156 | 33 |
| 4 | cryovial (frozen stock) | 103 | 22 |

TABLE 2

Results following transfection of primary amniocytes with pSTK146 UBE2I until polyclonal passage 4

| Passage no. | Culture vessel | no. of proliferating cell clones | % of isolated cell clones |
|---|---|---|---|
| 1 | 24-well dish | 221 | |
| 2 | 6-well dish | 185 | 84 |
| 3 | 9.2 cm dish | 164 | 74 |
| 4 | cryovial (frozen stock) | 157 | 71 |

Comparable results were obtained in amniocytes from two different amniocenteses.

Example 5

Single Cell Cloning of Amniocyte Cell Lines after Transformation with pSTK146 UBE2I Due to the mechanical method of isolation, described above, and the fact that multiple clones are isolated from each transfected cell culture dish, an isolated cell clone cannot be considered to be monoclonal, i.e. derived from a single cell. They are rather considered polyclonal at this stage. The following procedure was performed to obtain monoclonal cell lines from well-growing transformants.

Transformed cells in stable growing culture (polyclonal passage P 20, approx. 90 PDs) were detached, resuspended in culture medium and counted in a haemocytometer. Three dilutions were prepared of each cell suspension, containing 10, 20 or 50 viable cells/ml. Each of these dilutions was used to seed one flat-bottom 96-well dish with 100 µl of this cell suspension per well, resulting in a seeding density of 1, 2 or 5 viable cells per well.

For one week after seeding, each well was observed closely under 10-fold magnification to screen for attaching cells. Only wells with a single colony of cells, growing from a single attached cell, were chosen for further culture. From the point of seeding, each well was treated as a separate cell line, taking precautions against cross-contamination. The cell lines were expanded to larger culture vessels up to 9.2 cm dishes, at which point a first cell stock was frozen as described above. Cultures based on this stock were tested for the ability to produce ΔE1 Ad vectors, and highly productive cell lines were expanded for further cell banking. Two monoclonal cell lines with both good growth properties and good Ad vector production capability were named SGT11 1T3.1D9 and SGT11 1T3.1G3. These cell lines were deposited at the Deutsche Sammlung von Mikroorganismen and Zellkulturen GmbH (DSMZ), Inhoffenstrasse 7B, 38124 Braunschweig and received the number DSMZ ACC3134 (cell line SGT11 1T3.1D9) and DSM ACC3135 (cell line SGT11 1T3.1G3).

Example 6

Investigation of Senescence-Associated Beta-Galactosidase Expression

The changes in cellular morphology and the stop in proliferation of primary human amniocytes approaching passage 10 suggested that cells entered senescence at this point. Senescent cells express senescence-associated (SA) β-galactosidase at a much higher level than actively dividing immortal or tumor cells.

SA beta-galactosidase expression was evaluated in primary amniocytes, amniocytes at the polyclonal stage (clones) following transfection with plasmid pSTK146 UBE2I, immortalized monoclonal amniocyte cell lines and in 293 cells. The following samples were investigated:

a) primary human amniocytes of donor number 11 at passage 9 (SGT11 P9); at this stage the size of cells had already increased and the growth rate was reduced, i.e. the cells started to show a senescent phenotype;

b) polyclonal amniocyte cell clone of the same donor obtained from one focus after transfection with pSTK146 UBE2I at passages 8 and 24 (SGT11 1T3 P8 and SGT11 1T3 P24); and c) immortalized amniocyte cell line established from the above polyclonal cell clone after single cell cloning at passage 12 (1T3.1D9 P12).

The staining procedure was performed using the Senescence Cells Histochemical Staining Kit (Sigma-Aldrich, Saint Louis, Mo., USA) following standard procedures and the manufacturer's recommendations. Following staining, evaluation was performed using phase contrast with an inverted microscope. 10 images were randomly taken from each sample and SA β-galactosidase-positive cells were counted.

As the result 98.5% of SGT11 P9 were positive for SA β-galactosidase expression, 40.41% of SGT11 1T3 P8, 18.73% of SGT11 1T3 P24 and 13.29% of 1T3.1D9 P12. Results of these experiments are shown in FIG. 4.

This data indicated, that the change in morphology and growth arrest of primary amniocytes at around passage 10 was, indeed, senescence-associated and that this state was overcome by transfection of the primary cells with plasmid pSTK146 UBE2I.

Example 7

Determination of Telomere Length in Primary Amniocytes and Cell Lines

Human telomeric DNA is usually about 10 kb in length on average in primary cells. To investigate whether primary human amniocytes enter replicative senescence due to a telomere erosion-mediated DNA damage response, the length of the telomeric DNA of primary amniocytes and of established cell lines after transfection with pSTK146 UBE2I was determined. The N52.E6 cell lines that had been established by plasmid pST146 (Schiedner et al., 2000) served as control.

The length of telomeres is conveniently measured by a standard method, determining the telomere restriction fraction (TRF) (Harley et al., 1990). Genomic DNA is treated with restriction enzymes, which do not cleave within the repeating hexanucleotide 5'-TTAGGG-3' sequence constituting telomeric DNA. The cleaved DNA is separated by gel electrophoresis and the length of the TRFs is determined by hybridization with a probe that recognizes this hexanucleotide. As telomeres within one cell differ from chromosome to chromosome, and shortening may differ from cell to cell, the distribution of telomeric DNA in each sample is quite heterogeneous. The TRFs of the DNA samples from the following primary cells and cell lines in different passages were analysed:

a) primary human amniocytes of donor SGT11 at passages 6 and 9: SGT11 P6 and SGT11 P9;

b) polyclonal cell clones of the same donor after transfection with plasmid pSTK146 UBE2I at polyclonal passage 5 and 21: SGT11 1T3 P5 and SGT11 1T3 P21;

c) monoclonal cell lines of the same donor at monoclonal passages 9 and 23: 1T3.D9 P9 and 1T3.1D9P23; and d) as control, N52.E6 cells (transfected with pSKT146) were used.

The mean TRF of SGT11P6 and SGT11P9 was determined to be 10.3 and 9.8, respectively. The mean TRF of SGT11 1T3 P5 and SGT11 1T3 P21 was determined to be 7.8 and 8.4 kb, respectively. The mean TRF of SGT11 1T3.D9 P9 and SGT11 1T3.1D9 P23 was determined to be 7.9 and 7.9 kb, respectively. The mean TRF of N52.E6 cells was determined to be 4.6 kb. The TRFs from N52.E6 cells was determined from cells in a cell passage that corresponded to SGT11 1T3.1D9P23 cells. Results of these experiments are shown in FIG. 5.

From this experiment, two conclusions can be drawn: first, the senescence phenotype of primary human amniocytes at late passage (P11) is not caused by obvious telomere erosion. Rather it is likely due to so-called stress-induced premature senescence (SIPS), which is thought to be caused by accumulation of stresses in culture cells (Toussaint et al., 2000; Weinberg, R. A., 2007 supra). Second, the mean TRFs of N52.E6 cells, generated by transformation with pSTK146, are very short compared to cells that have been immortalized with pSTK146 UBE2I. This data, together with the observation that primary amniocytes do not enter crisis when immortalized with pSTK146 UBE2I, but do undergo crisis when transfected with pSTK146, indicates that replicative senescence is prevented by transformation of primary amniocytes with plasmid pSTK146 UBE2I.

Example 8

Production of ΔE1 Adenovirus Vectors in Amniocyte-Derived Clones and Cell Lines

The following screening protocol was used to compare and quantify the vector production capability of isolated and expanded clones. The results of these screenings, in addition to the stability of cell growth, were the basis for selection of clones for further culture and single-cell cloning.

Following standard procedures, one day after seeding at a defined density, cells were infected with a ΔE1 Ad vector carrying a GFP expression cassette (Ad1stGFP) at an infectious multiplicity of infection (MOI) of 5 to 20. Cells were harvested mechanically using a cell scraper 48 hours after infection, separated from culture medium by centrifugation, resuspended in buffer and lysed by three rounds of freezing in liquid nitrogen and thawing in a 37° C. water bath. The resulting lysate, containing the produced vector particles, was cleared of cell debris by centrifugation.

Dilutions of the clarified lysates were used to infect A549 cells (in which ΔE1 Ad vectors cannot replicate), also seeded at a defined density. Further 48 hours after infection, A549 were harvested and analyzed by flow cytometry, using the mean fluorescence intensity (corresponding to the level of intracellular GFP expression) as a measure for the number of infectious vector particles received per A549 cell. For a certain range of infectious MOI, the correlation between infectious dose and mean fluorescence intensity in A549 is linear. Therefore, by infection of A549 with defined infectious MOI to establish a standard curve, the average number of infectious particles produced per cell can be calculated.

It was found that the monoclonal cell lines SGT11 1T3.1D9 and SGT11 1T3.1G3 allowed production of Ad1stGFP at high levels with production of more than 2500 infectious Ad1stGFP particles per cell in SGT11 1T3.1D9 cells and more than 1000 infectious Ad1stGFP particles per cells in SGT11 1T3.1G3 cells as may also be taken from FIG. 6.

Example 9

Generation of RCA During Vector Production

The possible risk of RCA generation during vector production in the new cell lines was assessed by serial passage of a ΔE1Ad vector in two different permanent amniocyte cell lines SGT11 1T3.1D9 and SGT11 1T3.1G3. Since it is known that ΔE1Ad vectors, when produced in HEK293 cells, frequently result in the generation of RCA HEK293 cells were used as a control. RCA is generated by DNA recombination due to sequence overlap between DNA of the ΔE1Ad vector and the chromosomally integrated adenoviral DNA. The assay was performed in two different formats.

In a first format, 10 wells of each cell line ($1.5 \times 10^6$ cells/well in 6-well cell culture dishes) were infected with an MOI of 10 infectious particles per cell of the ΔE1 Ad vector Ad1stGFP and harvested after 48 h. Cells were lysed by three times freezing and thawing. 10% of each cell lysate (high infection format) was used to infect cells of the same cell line for another cycle of 48 h. This procedure was repeated for a total 15 passages.

In a second format of this assay, cells were infected with 0.1% of cell lysate from the previous passage (low infection format) and harvested when a cytopathic effect (CPE) became visible after 5-8 days. This procedure was also repeated for 15 passages.

RCA detection was performed essentially as described previously (Fallaux et al. Hum Gene Ther 1998, 9, 1909-17). The assay is performed on human cell lines (A549 cells and HeLa cells) that do not allow replication of a ΔE1 Ad vector. Only in the case of RCA generation and the presence of RCA, a full infectious cycle can occur resulting in a classical CPE. Thus, the final lysate was incubated on HeLa cells for 4 days. Then, HeLa cells were lysed by freezing and thawing and the lysate was added to A549 cells for 10 days. A visible CPE on A549 indicated the presence of RCA, as a first-generation vector could not replicate in either HeLa or A549. To test the detection limit of this assay, control HeLa dishes were infected with lysates spiked with Ad5 wild-type particles at very low multiplicity of infection. The assay has been found sensitive enough to detect 6 RCA particles per infected HeLa dish.

After 15 virus passages, no RCA was detected in any lysate of amniocyte-based cell lines (40 lysates tested), while three in 20 final lysates of HEK293 cells were found to contain RCA. Also, there was no evidence for the generation of HDEPs in SGT11 1T3.1D9 and in SGT11 1T3.1G3 cells. HDEPs would have become apparent as CPE, when A549 or HeLa cells were exposed to the cell lysates obtained from the serial passages.

Example 10

Karyotype Analyses

Karyotype analyses were performed from metaphases following standard procedures as they are routinely used in cytogenetic laboratories. Metaphases were analysed using the METAFER 4 equipment of MetaSystems GmbH, Altlussheim, Germany. Images were edited with the IKAROS software in order to obtain the following karyogramms Primary amniocytes, polyclonal cell clones at 2 different passages (Passages 10 and 20) and monoclonal cell lines (passages 14 and 23) were analysed.

The following results were obtained:

a) Primary amniocytes from individual SGT11 in passage 8 (SGT11 P8), corresponding to an estimated total PD of 30.
Karyotype: 46,XX (normal female karyotype)

b) Polyclonal clone established from the same individual in polyclonal passage 10 (SGT11 1T3 P10), corresponding to an estimated total PD of 68 to 70.
Karyotype: 71,XXX, +mar(del(8)t(X,8)(q;p)

c) Polyclonal clone established from the same individual in polyclonal passage 20 (SGT11 1T3 P20), corresponding to an estimated total PD of 90.
Karyotype: 75, XXX, +mar(del(8)t(X,8)(q;p)+elongation of 1q d) Monoclonal cell line established from the same individual in monoclonal passage 14 (SGT11 1T3.1D9 P14), corresponding to an estimated total PD of 140.
Karyotype: 55, XX, +mar(del(8)t(X,8)(q;p)

e) Monoclonal cell line established from the same individual in monoclonal passage 23 (SGT11 1T3.1D9 P23), corresponding to an estimated total PD of 160.
Karyotype: 61,XX, +mar(del(8)t(X,8)(q;p)+homologous stained region (HSR) on 1p Starting from a normal female karyotype (46,XX) in primary amniocytes, a polyploid karyotype was observed with chromosome numbers between 75 and 55 and one consistent translocation (t(X;8)(q;p) observed in the polyclonal cell clone in passage 10 (total PD of 68 to 70) and in passage 20 (total PD of 90), and in the monoclonal cell line in passage 14 (total PD of 140) and in passage 23 (total PD of 160). Only an elongation of 1q visible in passage 20 in the polyclonal status, and one HSR on 1p visible in passage 23 in the single cell cloned status of the cell line. No additional structural abnormalities were detected despite long-term cultivation, indicating a remarkable stability of the karyotype.

Example 11

Structural Characteristics of the E1 Region of Ad 5

The E1 region of Ad5 like is characterized by a complex structure with overlapping reading frames encoding for several E1A and E1B proteins. Within the E1B sequence two SD and three SA site are present enabling alternative splicing of the E1B mRNA transcript. In addition to the consensus splice sites, the use of cryptic splice sites in this region may give rise to unwanted E1B protein products and/or may result in a lower expression of the major E1B protein E1B 55K. When analysing different genomic 3'UTR sequences for the presence of ESEs using the 238 ESEs shown in Table 3 it was found that these sequences exhibited a decreased number of ESEs compared to the SV40 sequences present in pSTK146.

TABLE 3

List of 238 candidate ESEs as predicted by Fairbrother et al., 2002

| | |
|---|---|
| 1 | AAAACC |
| 2 | AAAAGA |
| 3 | AAAAGC |
| 4 | AAACAG |
| 5 | AAACCA |
| 6 | AAACCT |
| 7 | AAACGA |
| 8 | AAAGAA |
| 9 | AAAGAC |
| 10 | AAAGAG |
| 11 | AAAGAT |
| 12 | AAAGCA |
| 13 | AAAGCT |
| 14 | AAAGGA |
| 15 | AAATCC |
| 16 | AACAAC |
| 17 | AACAAG |
| 18 | AACAGA |
| 19 | AACCAA |
| 20 | AACGAA |
| 21 | AACTGG |
| 22 | AACTTC |
| 23 | AAGAAA |
| 24 | AAGAAC |
| 25 | AAGAAG |
| 26 | AAGAAT |
| 27 | AAGACA |
| 28 | AAGACT |
| 29 | AAGAGA |
| 30 | AAGAGG |
| 31 | AAGATC |

TABLE 3-continued

List of 238 candidate ESEs as predicted by Fairbrother et al., 2002

| | |
|---|---|
| 32 | AAGATG |
| 33 | AAGCAA |
| 34 | AAGCAG |
| 35 | AAGCCA |
| 36 | AAGCTA |
| 37 | AAGGAA |
| 38 | AAGGAC |
| 39 | AAGGAT |
| 40 | AATCAA |
| 41 | AATCCA |
| 42 | AATGAC |
| 43 | AATGGA |
| 44 | ACAAAG |
| 45 | ACAACG |
| 46 | ACAACT |
| 47 | ACAAGA |
| 48 | ACAGAA |
| 49 | ACCTGA |
| 50 | ACGAAA |
| 51 | ACGAAG |
| 52 | ACGACT |
| 53 | ACTGAA |
| 54 | ACTTCA |
| 55 | ACTTCG |
| 56 | AGAAAA |
| 57 | AGAAAC |
| 58 | AGAAAG |
| 59 | AGAACA |
| 60 | AGAACT |
| 61 | AGAAGA |
| 62 | AGAAGC |
| 63 | AGAAGG |
| 64 | AGAAGT |
| 65 | AGAATT |
| 66 | AGACAA |
| 67 | AGACAT |
| 68 | AGACGA |
| 69 | AGAGAA |
| 70 | AGAGAT |

TABLE 3-continued

List of 238 candidate ESEs as predicted by Fairbrother et al., 2002

| | |
|---|---|
| 71 | AGAGGA |
| 72 | AGATGA |
| 73 | AGATGC |
| 74 | AGATGT |
| 75 | AGCAAA |
| 76 | AGCAGA |
| 77 | AGGAAA |
| 78 | AGGAAC |
| 79 | AGGAAG |
| 80 | AGGACA |
| 81 | AGGAGA |
| 82 | AGTGAA |
| 83 | ATCAAA |
| 84 | ATCAAG |
| 85 | ATCAAT |
| 86 | ATCAGA |
| 87 | ATCCAA |
| 88 | ATGAAG |
| 89 | ATGAGA |
| 90 | ATGATG |
| 91 | ATGCAA |
| 92 | ATGGAA |
| 93 | ATGGCG |
| 94 | ATTCAG |
| 95 | ATTGGA |
| 96 | CAAAAC |
| 97 | CAAAAG |
| 98 | CAAAGA |
| 99 | CAACTT |
| 100 | CAAGAA |
| 101 | CAAGAT |
| 102 | CAAGTA |
| 103 | CAATCA |
| 104 | CAGAAA |
| 105 | CAGAAG |
| 106 | CAGAAT |
| 107 | CAGAGG |
| 108 | CAGGAA |

TABLE 3-continued

List of 238 candidate ESEs as predicted by Fairbrother et al., 2002

| | |
|---|---|
| 109 | CCTGAA |
| 110 | CGAAAA |
| 111 | CGAACA |
| 112 | CGAAGA |
| 113 | CGACGA |
| 114 | CGTATG |
| 115 | CTGAAA |
| 116 | CTGAAG |
| 117 | CTTCAG |
| 118 | GAAAAA |
| 119 | GAAAAC |
| 120 | GAAAAG |
| 121 | GAAACA |
| 122 | GAAACC |
| 123 | GAAACG |
| 124 | GAAACT |
| 125 | GAAAGA |
| 126 | GAAAGC |
| 127 | GAAATC |
| 128 | GAACAA |
| 129 | GAACAT |
| 130 | GAACTG |
| 131 | GAACTT |
| 132 | GAAGAA |
| 133 | GAAGAC |
| 134 | GAAGAG |
| 135 | GAAGAT |
| 136 | GAAGCA |
| 137 | GAAGGA |
| 138 | GAAGTA |
| 139 | GAAGTT |
| 140 | GAATCA |
| 141 | GACAAA |
| 142 | GACAAT |
| 143 | GACGAA |
| 144 | GACGAC |
| 145 | GAGAAA |
| 146 | GAGAAG |
| 147 | GAGAGA |

TABLE 3-continued

List of 238 candidate ESEs as predicted by Fairbrother et al., 2002

| | |
|---|---|
| 148 | GAGATG |
| 149 | GAGGAA |
| 150 | GAGGAG |
| 151 | GAGGAT |
| 152 | GATATC |
| 153 | GATATG |
| 154 | GATCAA |
| 155 | GATCAT |
| 156 | GATGAA |
| 157 | GATGAG |
| 158 | GATGAT |
| 159 | GATGCA |
| 160 | GATGGA |
| 161 | GATTCA |
| 162 | GCAAAA |
| 163 | GCAAGA |
| 164 | GCAGAA |
| 165 | GGAAAA |
| 166 | GGAAAC |
| 167 | GGAAGA |
| 168 | GGAGAA |
| 169 | GGAGGA |
| 170 | GGATCA |
| 171 | GTCAAG |
| 172 | GTGAAG |
| 173 | TACAAG |
| 174 | TACAGA |
| 175 | TATGGA |
| 176 | TCAAGA |
| 177 | TCAGAA |
| 178 | TCAGGA |
| 179 | TGAAAC |
| 180 | TGAAAG |
| 181 | TGAAGA |
| 182 | TGAAGC |
| 183 | TGAAGG |
| 184 | TGAAGT |
| 185 | TGAOAA |

TABLE 3-continued

List of 238 candidate ESEs as predicted by Fairbrother et al., 2002

| | |
|---|---|
| 186 | TGATGA |
| 187 | TGCAAC |
| 188 | TGGAAA |
| 189 | TGGAAG |
| 190 | TGGAAT |
| 191 | TGGATC |
| 192 | TTCAGA |
| 193 | TTCGAA |
| 194 | TTGAAG |
| 195 | TTGCGA |
| 196 | TTGGAA |
| 197 | TTGGAT |
| 198 | TTTGGA |
| 199 | AAAAAG |
| 200 | AAACTC |
| 201 | AACATG |
| 202 | AACCAG |
| 203 | AACTAC |
| 204 | AAGGAG |
| 205 | AATACG |
| 206 | AATCAG |
| 207 | AATGAA |
| 208 | ACATGA |
| 209 | ACGCAA |
| 210 | ACTACA |
| 211 | ACTGGA |
| 212 | AGTGAC |
| 213 | ATCTTC |
| 214 | ATGAAA |
| 215 | ATGGAT |
| 216 | ATGGTC |
| 217 | CAAACA |
| 218 | CAGATC |
| 219 | CATCAG |
| 220 | CGAATG |

TABLE 3-continued

List of 238 candidate ESEs as predicted by Fairbrother et al., 2002

| 221 | CGTCGC |
|---|---|
| 222 | CTACAT |
| 223 | CTCCAT |
| 224 | GAAAAT |
| 225 | GAACCA |
| 226 | GCGAAT |
| 227 | GGAGAT |
| 228 | GTCGAC |
| 229 | GTGTCG |
| 230 | GTTGGA |
| 231 | TATGAA |
| 232 | TCAACG |
| 233 | TCATCA |
| 234 | TCGTCG |
| 235 | TCTTCA |
| 236 | TGACTG |
| 237 | TGGAAC |
| 238 | TGTGGA |

A comparison of this analysis for pSTK146 and for pSTK146 UBE2I is shown in Table 4. In this table also the results of the ESE analysis for other suitable 3'UTRs, derived from the ARF5, the DAXX, the HPRT and RING1 locus are shown.

Example 12

Generation of Immortalized Amniocyte Cell Lines with a Nucleic Acid Construct where the E1A Genes are Under Regulatable Promoter Control In the nucleic acid construct of the present invention used in this example, the E1A cDNA of hAd5 was placed under the control of a Tetracycline (Tet)-inducible promoter.

The Tet-On Advanced System (Clontech) was used to generate a nucleic acid construct, in which the E1A is tetracycline-inducible. This system is based on expression of the Tet-On Advanced transactivator, which is a fusion protein derived from a mutant version of the *E. coli* Tet repressor protein, rTetR, which is joined to three minimal transcription activation domains from the HSV VP16 protein. In the presence of doxycycline (Dox), Tet-On Advanced binds to the tetracycline response element (TREMod) in PTight, which is placed in front of a coding sequence of choice, resulting in activation of gene expression.

Figure 2:
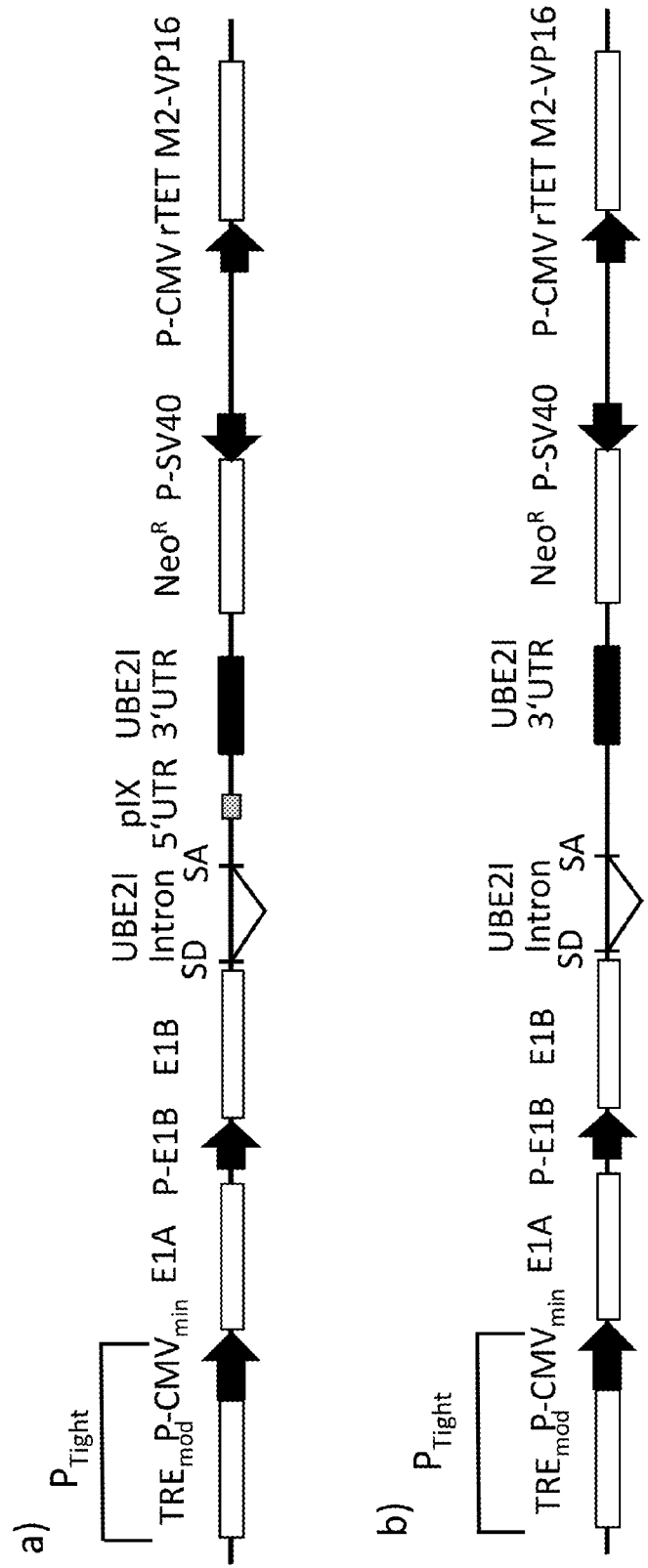
Figure 3:
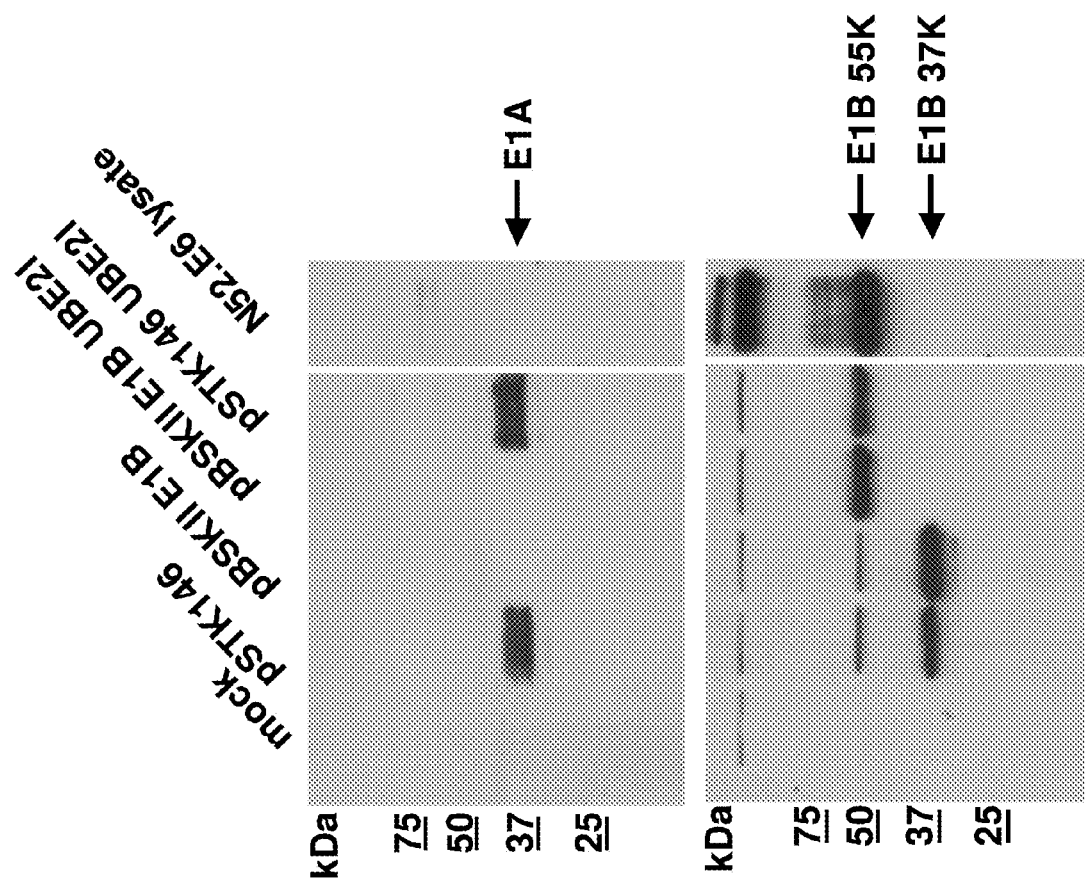
FIG. 3 shows the result of a Western blot analysis, whereby the expression of E1A (detected by E1A-specific antibody M73 (Calbiochem), E1B 55 kD and E1B 37 kD (detected by 2A6 antibody binding to the N-terminus of E1B proteins (Sarnow et al., 1982) is shown using the indicated nucleic acid constructs for transfection.

A nucleic construct was generated containing both the transactivator and the transgene sequence on one nucleic acid molecule named plasmid pTL13 (FIG. 2 and SEQ ID NO:23). This DNA construct encompassed the following elements:

a) the expression cassette coding for the Tet-On Advanced transactivator (rTET M2-VP16), b) the E1A cDNA under the control of the Tet-inducible promoter (PTight), and c) the E1B cDNA operatively linked to the natural E1B promoter and followed by the UBE2I intron, part of the pIX5'UTR (to allow for expression of the E1B84R protein) and the UBE2I 3' UTR.

For construction of pTL13, the plasmid pSTK146 UBE2I was digested with EcoRV and NotI to release a 3.7 kb fragment containing the Ad5 E1A coding sequence, the Ad5 E1B cDNA operatively linked to the natural E1B promoter and followed by the UBE2I intron, the C-terminus of E1B

TABLE 4

ESEs present in pSTK146, in pSTK146BE2I and in additional sequences

| Origin of Intron | Origin of 3' UTR | DNA | Number of ESEs in 200 nucleotide length of 3'UTR |
|---|---|---|---|
| SV40 poly late gi\|9628421\|ncbi\|NC_001669.1 | SV40 poly late gi\|9628421\|ncbi\|NC_001669.1 | pSTK146 | 40 |
| UBE2I gi\|224589807: 1359180-1375390\| ncbi\|NC_000016.9\| | UBE2I gi\|224589807: 1359180-1375390\| ncbi\|NC_000016.9\| | pSTK146 UBE2I | 1 |
| ARF5 gi\|224589819: 127228406-127231759\| ncbi\|NC_000007.13 | ARF5 gi\|224589819: 127228406-127231759\| ncbi\|NC_000007.13 | | 1 |
| DAXX gi\|224589818: c33290793-33286335\| ncbi\|NC_000006.11 | DAXX gi\|224589818: c33290793-33286335\| ncbi\| NC_000006.11 | | 24 |
| HPRT gi\|224589822: 133594175-133634698\| ncbi\|NC_000023.10 | HPRT gi\|224589822: 133594175-133634698\| ncbi\|NC_000023.10 | | 13 |
| RING1 gi\|224589818: 33176286-33180499\| ncbi\|NC_000006.11 | RING1 gi\|224589818: 33176286-33180499\| ncbi\|NC_000006.11 | | 15 |

84R and the UBE2I 3' UTR. This fragment was then cloned into the pTRE-Tight (Clontech) vector's multiple cloning site (SuraI, NotI) located downstream of the Tet-inducible promoter Ptight to obtain a construct named pTL12. To generate pTL13, the 4.4. kb BamHI fragment—containing the transactivator sequence—obtained from the plasmid pTet-On-Advanced (Clontech) was then subcloned into the BamHI site of pTL12.

For generation of immortalized amniocyte cell lines plasmid pTL13 is transfected into primary amniocytes as described above for the pSTK146 UBE2I plasmid, with doxycycline added to the cell culture medium at a concentration following the manufacturer's recommendation and in general being at a range between 0.01 and 2 µg/ml.

Example 13

Immortalization of Primary Human Amniocytes by Transfection with Two Plasmids Expressing E1A and E1B Independently This example illustrates the nucleic acid construct of the present invention, whereby the nucleic acid construct is a two-piece nucleic acid construct.

This two-step transfection procedure essentially follows the one-step transfection described above in example 4, with minor modifications. The two nucleic acid constructs, one expressing E1A, the second E1B, are transfected into primary human amniocytic cells, either at the same time (e.g. by mixing the two plasmid DNAs) or in two consecutive transfections. The latter procedure (i.e. two transfections) increases the chance of integration of the two nucleic acid constructs at different chromosomal sites, which may further reduce the risk of RCA generation if the resulting cell line is used for production of ΔE1 Ad vectors. The amount of PEI as transfection reagent is lowered in the separate transfection steps to minimize its cytotoxic effects.

Materials Used:
Plasmid DNA in Tris-EDTA buffer, pH 7.5, linearized with restriction enzyme BspHI
pBSK E1B UBE2I
pmPGK E1A, expressing E1A from the murine PGK promoter
Solution of linear PEI, 7.5 mM, pH 7.0, sterile filtered
NaCl solution, 150 mM, sterile filtered The sequence of the functional sequence elements contained in plasmid pBSK E1B UBE2I is provided as SEQ ID NO 7: it contains the E1B promoter, the E1B 19K and 55K coding region, the UBE2I intron and comprising part of the 5'-UTR of the pIX gene, and the UBE2I 3'UTR. Thus, in this example plasmid pBSK E1B UBE2I expresses E1B under control of its natural promoter. The 3' UTR region is identical to that of the pSTK146 UBE2I plasmid described above. The second nucleic construct required for immortalization of primary amniocytes comprises an expression unit coding for the E1A functions. The sequence of an expression unit coding for E1A is provided in SEQ ID NO 8. It contains as a constitutive promoter the murine pgk promoter, the E1A coding region and the 3'UTR from the UBE2I gene.

If transfection of the two plasmids is performed at the same time, the two plasmid DNAs can be mixed and transfection is performed as described above for plasmids expressing both the E1A and E1B functions.

If transfection of the two plasmids is performed consecutively, the procedure is performed as follows:

For each culture dish to be transfected, 2 µg of linearized pmPGK E1A expressing E1A and 18 µl of PEI solution are separately diluted ad 250 µl with NaCl solution. Each PEI dilution is added to one DNA dilution. Preparations are mixed and incubated at room temperature for 15 to 20 minutes. Primary human amniocytes, seeded in 6 cm culture dishes on the previous day, are washed with PBS and supplied with fresh culture medium. Each transfection complex is added to one prepared dish. Two days later, the same procedure is performed with the E1B expressing plasmid pBSK E1B UBE2I. The day after the second transfection, cells are passaged to 14 cm culture dishes, and subsequently treated according to the same protocols as the single-plasmid transfected cultures.

The procedure can also be performed vice versa, i.e. transfecting first the E1B expressing plasmid, followed by the E1A expressing plasmid. The procedure can also be performed by using other transfection reagents then PEI or by using retroviral or lentiviral vectors for delivery of both nucleic acid constructs coding for E1A and E1B, respectively, into primary amniocytic cells.

REFERENCES

The complete bibliographic data of the documents recited herein the disclosure of which is incorporated by reference is, if not indicated to the contrary, as follows.

Adra C N, Boer P H, and McBurney M W. Cloning and expression of the mouse pgk-1 gene and the nucleotide sequence of its promoter. Gene 1987; 60:65-74.

Bangari D S, Mittal S K. Development of nonhuman adenoviruses as vaccine vectors. Vaccine 2006; 24(7):849-62.

Baron U, Gossen M, Bujard H. Tetracycline-controlled transcription in eukaryotes: novel transactivators with graded transactivation potential. Nucleic Acids Res. 1997 Jul. 15; 25(14):2723-9.

Ben-Porath I, Weinberg R A. The signals and pathways activating cellular senescence. Int J Biochem Cell Biol. 2005 May; 37(5):961-76.

Berk A J. Recent lessons in gene expression, cell cycle control, and cell biology from adenovirus. Oncogene. 2005 Nov. 21; 24(52):7673-85.

Blackford A N, Grand R J. Adenovirus E1B 55-kilodalton protein: multiple roles in viral infection and cell transformation. J Virol. 2009 May; 83(9):4000-12.

Boshart M, Weber F, Jahn G, Dorsch-Hasler K, Fleckenstein B, and Schaffner W A very strong enhancer is located upstream of an immediate early gene of human cytomegalovirus. Cell 1985; 41:521-530.

Burcin M M, O'Malley B W, Tsai S Y. A regulatory system for target gene expression. Front. Biosci 1998; 3:c1-c7.

Burset M, Seledtsov I A, Solovyev V V, SpliceDB: database of canonical and non-canonical mammalian splice sites. Nucleic Acids Res. 2001; 29:255-9.

Byrd P, Brown K W, Gallimore P H. Malignant transformation of human embryo retinoblasts by cloned adenovirus 12 DNA. Nature 1982; 298(5869):69-71.

Davies J, Jimenez A. A new selective agent for eukaryotic cloning vectors (1980). Am J Trop Med Hyg 29 (5 Suppl):1089-92.

Dorsch-Hasler K, Keil G M, Weber F, Jasin M, Schaffner W, and Koszinowski U H. A long and complex enhancer activates transcription of the gene coding for the highly abundant immediate early mRNA in murine cytomegalovirus. Proc Natl Acad Sci USA. 1985; 82:8325-8329.

Endter C, Kzhyshkowska J, Stauber R, Dobner T. SUMO-1 modification required for transformation by adenovirus type 5 early region 1B 55-kDa oncoprotein. Proc Natl Acad Sci USA. 2001 Sep. 25; 98(20):11312-7.

Fairbrother W G., Yeh R F., Sharp P A., and Burge C B. (2002). Predictive identification of exonic splicing enhancers in human genes. Science 297, 1007-1013.

Fairbrother W G, Yeo G W, Yeh R, Goldstein P, Mawson M, Sharp, P A, and Burge C B. (2004). RESCUE-ESE identifies candidate exonic splicing enhancers in vertebrate exons. Nucleic Acids Res. 32, W187-190.

Fallaux F J, Bout A, van der Velde I, van den Wollenberg D J, Hehir K M, Keegan J, Auger C, Cramer S J, van Ormondt H, van der Eb A J, Valerio D, Hoeben R C. New helper cells and matched early region 1-deleted adenovirus vectors prevent generation of replication-competent adenoviruses. Hum Gene Ther. 1998 Sep. 1; 9(13):1909-17.

Fallaux F J, Kranenburg O, Cramer S J, Houweling A, Van Ormondt H, Hoeben R C, Van Der Eb A J Characterization of 911: a new helper cell line for the titration and propagation of early region 1-deleted adenoviral vectors. Hum Gene Ther. 1996 Jan. 20; 7(2):215-22.

Gallimore P H, Grand R J, Byrd P J. Transformation of human embryo retinoblasts with simian virus 40, adenovirus and ras oncogenes. Anticancer Res 1986; 6(3 Pt B):499-508

Gao W, Robbins P D, Gambotto A. Human adenovirus type 35: nucleotide sequence and vector development. Gene Ther. 2003 November; 10(23):1941-9.

Graham F L, Smiley J, Russell W C, Nairn R. Characteristics of a human cell line transformed by DNA from human adenovirus type 5. J Gen Virol 1977; 36(1):59-74.

Harley C B, Futcher A B, Greider C W. Telomeres shorten during ageing of human fibroblasts. Nature. 1990 May 31; 345(6274):458-60

Hehir K M, Armentano D, Cardoza L M, Choquette T L, Berthelette P B, White G A, Couture L A, Everton M B, Keegan J, Martin J M, Pratt D A, Smith M P, Smith A E, Wadsworth S C. Molecular characterization of replication-competent variants of adenovirus vectors and genome modifications to prevent their occurrence. J Virol. 1996 December; 70(12):8459-67.

Hoehn H, Bryant E M, Karp L E, Martin G M Cultivated cells from diagnostic amniocentesis in second trimester pregnancies. I. Clonal morphology and growth potential. Pediatr Res. 1974 August; 8(8):746-54.

Hu M C, Davidson N. The inducible lac operator-repressor system is functional in mammalian cells. Cell 1987; 48:555-566.

Hynes N E, Groner B. Mammary tumor formation and hormonal control of mouse mammary tumor virus expression. Curr Top Microbiol Immunol. 1982; 101:51-74.

Imperiale M J, Kochanek S. Adenovirus vectors: biology, design, and production. Curr Top Microbiol Immunol. 2004; 273:335-57.

Kim N, Alekseyenko A V, Roy M, and Lee C. The ASAP II database: analysis and comparative genomics of alternative splicing in 15 animal species. Nucleic Acids Res. 2007; 35, D93-98.

Lewin B, Genes VIII, Pearson Education International, 2004, ISBN: 0-13-123924-4.

Loew R, Heinz N, Hampf M, Bujard H, Gossen M Improved Tet-responsive promoters with minimized background expression. BMC Biotechnol. 2010 Nov. 24; 10:81

Louis N, Evelegh C, Graham F L. Cloning and sequencing of the cellular-viral junctions from the human adenovirus type 5 transformed 293 cell line. Virology 1997; 233(2): 423-9

Lochmüller H, Jani A, Huard J, Prescott S, Simoneau M, Massie B, Karpati G, Acsadi G. Emergence of early region 1-containing replication-competent adenovirus in stocks of replication-defective adenovirus recombinants (delta E1+delta E3) during multiple passages in 293 cells. Hum Gene Ther. 1994 December; 5(12):1485-91.

McConnell M J, Imperiale M J. Biology of adenovirus and its use as a vector for gene therapy. Hum Gene Ther 2004; 15(11):1022-33.

Murakami P, Havenga M, Fawaz F, Vogels R, Marzio G, Pungor E, Files J, Do L, Goudsmit J, McCaman M Common structure of rare replication-deficient E1-positive particles in adenoviral vector batches. J Virol. 2004 June; 78(12):6200-8.

Murakami P, Pungor E, Files J, Do L, van Rijnsoever R, Vogels R, Bout A, McCaman M. A single short stretch of homology between adenoviral vector and packaging cell line can give rise to cytopathic effect-inducing, helper-dependent E1-positive particles. Hum Gene Ther. 2002 May 20; 13(8):909-20.

No D, Yao T P, Evans R M. Ecdysone-inducible gene expression in mammalian cells and transgenic mice. Proc Natl Acad Sci USA. 1996; 93:3346-3351.

Parks R J, Chen L, Anton M, Sankar U, Rudnicki M A, Graham F L. A helper-dependent adenovirus vector system: removal of helper virus by Cre-mediated excision of the viral packaging signal. Proc Natl Acad Sci USA. 1996 Nov. 26; 93(24):13565-70.

Pesole G, Mignone F, Gissi C, Grillo G, Licciulli F, Liuni S. Structural and functional features of eukaryotic mRNA untranslated regions. Gene 2001; 276:73-8

Proudfoot N J. Ending the message: poly(A)signals then and now. Genes Dev. 2011, 25:1770-82.

Sarnow P, Sullivan C A, Levine A J. A monoclonal antibody detecting the adenovirus type 5-E1b-58Kd tumor antigen: characterization of the E1b-58Kd tumor antigen in adenovirus-infected and -transformed cells. Virology 1982 Jul. 30; 120(2):510-7.

Schiedner G, Hertel S, Bialek C, Kewes H, Waschütza G, Volpers C. Efficient and reproducible generation of high-expressing, stable human cell lines without need for antibiotic selection. BMC Biotechnol. 2008 Feb. 12; 8:13.

Schiedner G, Hertel S, Kochanek S. Efficient transformation of primary human amniocytes by E1 functions of Ad5: generation of new cell lines for adenoviral vector production. Hum Gene Ther. 2000 Oct. 10; 11(15):2105-16.

Sieber T, Dobner T. Adenovirus type 5 early region 1B 156R protein promotes cell transformation independently of repression of p53-stimulated transcription. J Virol. 2007 January; 81(1):95-105.

Silva A C, Peixoto C, Lucas T, Küppers C, Cruz P E, Alves P M, Kochanek S. Adenovirus vector production and purification. Curr Gene Ther. 2010 December; 10(6):437-55.

Singer-Sam J, Keith D H, Tani K, Simmer R L., Shively L, Lindsay S, Yoshida A, and Riggs A D. Sequence of the promoter region of the gene for human X-linked 3-phosphoglycerate kinase. Gene 1984; 32: 409-417.

Schreiner S, Wimmer P, Groitl P, Chen S Y, Blanchette P, Branton P E, Dobner T. Adenovirus type 5 early region 1B 55K oncoprotein-dependent degradation of cellular factor Daxx is required for efficient transformation of primary rodent cells. J Virol. 2011 September; 85(17):8752-65.

Toussaint O, Medrano E E, von Zglinicki T. Cellular and molecular mechanisms of stress-induced premature senescence (SIPS) of human diploid fibroblasts and melanocytes. Exp Gerontol. 2000 October; 35(8):927-45.

Umaña P, Gerdes C A, Stone D, Davis J R, Ward D, Castro M G, Lowenstein P R. Efficient FLPe recombinase enables scalable production of helper-dependent adenoviral vectors with negligible helper-virus contamination. Nat Biotechnol. 2001 June; 19(6):582-5.

Vogels R, Zuijdgeest D, van Rijnsoever R, Hartkoorn E, Damen I, de Béthune M P, Kostense S, Penders G, Helmus N, Koudstaal W, Cecchini M, Wetterwald A, Sprangers M, Lemckert A, Ophorst O, Koel B, van Meerendonk M, Quax P, Panitti L, Grimbergen J, Bout A, Goudsmit J, Havenga M. Replication-deficient human adenovirus type 35 vectors for gene transfer and vaccination: efficient human cell infection and bypass of pre-existing adenovirus immunity. J Virol. 2003 August; 77(15):8263-71.

Whittaker J L, Byrd P J, Grand R J, Gallimore P H. Isolation and characterization of four adenovirus type 12-transformed human embryo kidney cell lines. Mol Cell Biol. 1984 January; 4(1):110-6.

Weinberg R A. The Biology of Cancer, Garland Science, 2007, ISBN 0-8153-4076-1.

Wurm F M, Gwinn K A, Kingston R E. Inducible overproduction of the mouse c-myc protein in mammalian cells. Proc Natl Acad Sci USA. 1986; 83:5414-5418.

The features of the present invention disclosed in the specification, the claims and/or the drawings may both separately and in any combination thereof be material for realizing the invention in various forms thereof.

The invention claimed is:

1. A nucleic acid construct comprising
(i) an expression unit for the expression of E1 B, wherein the expression unit comprises a promoter, a nucleotide sequence coding for E1 B, and a 3' UTR, wherein the promoter is operatively linked to the nucleotide sequence coding for E1 B, wherein the 3' UTR comprises 30 or fewer than 30 Exonic Splicing Enhancer elements (ESEs), and wherein the 3' UTR is a non-viral 3' UTR, and (ii) an expression unit for the expression of E1A, wherein the expression unit comprises a promoter, a nucleotide sequence coding for E1A, and a 3' UTR,
wherein the promoter is operatively linked to the nucleotide sequence coding for E1A, wherein the expression unit for the expression of E1A and the expression unit for the expression of EIB form a combined expression unit, wherein the combined expression unit comprises the nucleotide sequence of SEQ ID NO: 9 or SEQ ID NO: 15.

2. The nucleic acid construct of claim 1, wherein the 3' UTR comprises 20 or fewer than 20 Exonic Splicing Enhancer elements (ESEs).

3. The nucleic acid construct of claim 1, wherein the nucleic acid construct is a single nucleic acid molecule comprising both the expression unit for the expression of E1A and the expression unit for the expression of E1 B.

4. The nucleic acid construct according to claim 1, wherein the Exonic Splicing Enhancer elements (ESEs) are contained within a stretch of nucleotides of the 3' UTR of the expression unit for the expression of E1 B, and wherein said stretch of nucleotides comprises the 200 nucleotides of the 5' end of the 3' UTR of the expression unit for the expression of E1 B.

5. The nucleic acid construct according to claim 1, wherein the 3' UTR of the expression unit for the expression of E1 B is a mammalian 3' UTR.

6. The nucleic acid construct according to claim 1, wherein the expression unit for the expression of E1A and the expression unit for the expression of E1 B are arranged in a 5'->3' direction in the nucleic acid construct as follows: the promoter of the expression unit for the expression of E1A, the nucleotide sequence coding for E1A and the 3' UTR, the promoter of the expression unit for the expression of E1 B, the nucleotide sequence coding for E1 B, a splice donor site, an intron, a splice acceptor site and the 3' UTR.

7. The nucleic acid construct according to claim 1, wherein the nucleic acid construct is coding for and capable of expressing E1A, E1 B 55K, E1 B 19K and/or E1 B 84R.

8. The nucleic acid construct according to claim 7, wherein the nucleic acid construct is capable of expressing E1A, E1 B 55K, and E1 B 19K.

9. A vector comprising the nucleic acid construct according to claim 1.

10. A cell comprising a the vector according to claim 9.

11. The cell according to claim 10, wherein the cell is an amniocytic cell line.

12. The nucleic acid construct according to claim 7, wherein the nucleic acid construct is capable of expressing E1A, E1 B 55 K, E1 B 19 K and E1 B 84R.

* * * * *

SEQUENCE LISTING

<160> NUMBER OF SEQ ID NOS: 31

<210> SEQ ID NO 1
<211> LENGTH: 1899
<212> TYPE: DNA
<213> ORGANISM: Adenovirus serotype 5

<400> SEQUENCE: 1

```
atggaggctt gggagtgttt ggaagatttt tctgctgtgc gtaacttgct ggaacagagc      60
tctaacagta cctcttggtt ttggaggttt ctgtggggct catcccaggc aaagttagtc     120
tgcagaatta aggaggatta caagtgggaa tttgaagagc ttttgaaatc ctgtggtgag     180
ctgtttgatt ctttgaatct gggtcaccag gcgcttttcc aagagaaggt catcaagact     240
ttggattttt ccacaccggg gcgcgctgcg gctgctgttg ctttttttgag ttttataaag     300 gataaatgga gcgaagaaac ccatctgagc gggggtacc tgctggattt tctggccatg     360
catctgtgga gagcggttgt gagacacaag aatcgcctgc tactgttgtc ttccgtccgc     420
ccggcgataa taccgacgga ggagcagcag cagcagcagg aggaagccag gcggcggcgg     480
caggagcaga gcccatggaa cccgagagcc ggcctggacc ctcgggaatg aatgttgtac     540
aggtggctga actgtatcca gaactgagac gcattttgac aattacagag gatgggcagg     600
ggctaaaggg ggtaaagagg gagcggggg cttgtgaggc tacagaggag gctaggaatc     660
tagcttttag cttaatgacc agacaccgtc ctgagtgtat tacttttcaa cagatcaagg     720
ataattgcgc taatgagctt gatctgctgg cgcagaagta ttccatagag cagctgacca     780
cttactggct gcagccaggg gatgattttg aggaggctat tagggtatat gcaaaggtgg     840
cacttaggcc agattgcaag tacaagatca gcaaacttgt aaatatcagg aattgttgct     900
acatttctgg gaacggggcc gaggtggaga tagatacgga ggatagggtg gcctttagat     960
gtagcatgat aaatatgtgg ccgggggtgc ttggcatgga cggggtggtt attatgaatg    1020
taaggtttac tggccccaat tttagcggta cggttttcct ggccaatacc aaccttatcc    1080
tacacggtgt aagcttctat gggtttaaca atacctgtgt ggaagcctgg accgatgtaa    1140
gggttcgggg ctgtgccttt tactgctgct ggaaggggt ggtgtgtcgc cccaaaagca    1200
gggcttcaat taagaaatgc ctctttgaaa ggtgtacctt gggtatcctg tctgagggta    1260
actccagggt gcgccacaat gtggcctccg actgtggttg cttcatgcta gtgaaaagcg    1320
tggctgtgat taagcataac atggtatgtg gcaactgcga ggacagggcc tctcagatgc    1380
tgacctgctc ggacggcaac tgtcacctgc tgaagaccat tcacgtagcc agccactctc    1440
gcaaggcctg gccagtgttt gagcataaca tactgacccg ctgttccttg catttgggta    1500
acaggagggg ggtgttccta ccttaccaat gcaatttgag tcacactaag atattgcttg    1560
```

| | |
|---|---|
| agcccgagag catgtccaag gtgaacctga acggggtgtt tgacatgacc atgaagatct | 1620 |
| ggaaggtgct gaggtacgat gagacccgca ccaggtgcag accctgcgag tgtggcggta | 1680 |
| aacatattag gaaccagcct gtgatgctgg atgtgaccga ggagctgagg cccgatcact | 1740 |
| tggtgctggc ctgcacccgc gctgagtttg gctctagcga tgaagataca gattgaggta | 1800 |
| ctgaaatgtg tgggcgtggc ttaagggtgg gaaagaatat ataaggtggg ggtcttatgt | 1860 |
| agttttgtat ctgttttgca gcagccgccg ccgccatga | 1899 |

<210> SEQ ID NO 2
<211> LENGTH: 986
<212> TYPE: DNA
<213> ORGANISM: Adenovirus serotype 5

<400> SEQUENCE: 2

| | |
|---|---|
| atgagacata ttatctgcca cggaggtgtt attaccgaag aaatggccgc cagtcttttg | 60 |
| gaccagctga tcgaagaggt actggctgat aatcttccac ctcctagcca ttttgaacca | 120 |
| cctaccctte acgaactgta tgatttagac gtgacggccc ccgaagatcc caacgaggag | 180 |
| gcggtttcgc agatttttcc cgactctgta atgttggcgg tgcaggaagg gattgactta | 240 |
| ctcactttc cgccggcgcc cggttctccg gagccgcctc acctttcccg gcagcccgag | 300 |
| cagccggagc agagagcctt gggtccggtt tctatgccaa accttgtacc ggaggtgatc | 360 |
| gatcttacct gccacgaggc tggctttcca cccagtgacg acgaggatga agagggtgag | 420 |
| gagtttgtgt tagattatgt ggagcacccc gggcacggtt gcaggtcttg tcattatcac | 480 |
| cggaggaata cggggggaccc agatattatg tgttcgcttt gctatatgag gacctgtggc | 540 |
| atgtttgtct acagtaagtg aaaattatgg gcagtgggtg atagagtggt gggtttggtg | 600 |
| tggtaattt tttttttaatt tttacagttt tgtggtttaa agaattttgt attgtgattt | 660 |
| ttttaaaagg tcctgtgtct gaacctgagc ctgagcccga ccagaaccg agcctgcaa | 720 |
| gacctacccg ccgtcctaaa atggcgcctg ctatcctgag acgcccgaca tcacctgtgt | 780 |
| ctagagaatg caatagtagt acggatagct gtgactccgg tccttctaac acacctcctg | 840 |
| agatacaccc ggtggtcccg ctgtgcccca ttaaaccagt tgccgtgaga gttggtgggc | 900 |
| gtcgccaggc tgtggaatgt atcgaggact tgcttaacga gcctgggcaa cctttggact | 960 |
| tgagctgtaa acgccccagg ccataa | 986 |

<210> SEQ ID NO 3
<211> LENGTH: 704
<212> TYPE: DNA
<213> ORGANISM: Simian Virus-40

<400> SEQUENCE: 3

| | |
|---|---|
| attccaacct atggaactga tgaatgggag cagtggtgga atgcctttaa tgaggaaaac | 60 |
| ctgttttgct cagaagaaat gccatctagt gatgatgagg ctactgctga ctctcaacat | 120 |
| tctactcctc caaaaaagaa gagaaaggta gaagacccca aggactttcc ttcagaattg | 180 |
| ctaagttttt tgagtcatgc tgtgtttagt aatagaactc ttgcttgctt tgctatttac | 240 |
| accacaaagg aaaagctgc actgctatac aagaaaatta tggaaaaata ttctgtaacc | 300 |
| tttataagta ggcataacag ttataatcat aacatactgt tttttcttac tccacacagg | 360 |
| catagagtgt ctgctattaa taactatgct caaaaattgt gtacctttag cttttttaatt | 420 |
| tgtaaagggg ttaataagga atatttgatg tatagtgcct tgactagaga tcataatcag | 480 |
| ccataccaca tttgtagagg ttttacttgc tttaaaaaac ctcccacacc tccccctgaa | 540 |

```
cctgaaacat aaaatgaatg caattgttgt tgttaacttg tttattgcag cttataatgg    600
ttacaaataa agcaatagca tcacaaattt cacaaataaa gcattttttt cactgcattc    660
tagttgtggt ttgtccaaac tcatcaatgt atcttatcat gtct                    704
```

<210> SEQ ID NO 4
<211> LENGTH: 73
<212> TYPE: DNA
<213> ORGANISM: Simian Virus-40

<400> SEQUENCE: 4

```
gtactgaaat ggaattcaat ttttaagtgt ataatgtgtt aaactactga ttctaattgt     60
ttgtgtattt tag                                                        73
```

<210> SEQ ID NO 5
<211> LENGTH: 4182
<212> TYPE: DNA
<213> ORGANISM: artificial
<220> FEATURE:
<223> OTHER INFORMATION: synthetic

<400> SEQUENCE: 5

```
taccgggtag gggaggcgct tttcccaagg cagtctggag catgcgcttt agcagccccg     60
ctggcacttg cgctacacac agtggcctct ggcctcgcac acattccaca tccaccggta    120
ggcgccaacc ggctccgttc tttggtggcc ccttcgcgcc accttctact cctcccctag    180
tcaggaagtt ccccccgcc ccgcagctcg cgtcgtgcag gacgtgacaa atggaagtag    240
cacgtctcac tagtctcgtg cagatggaca gcaccgctga gcaatggaag cgggtaggcc    300
tttggggcag cggccaatag cagctttgct ccttcgcttt ctgggctcag aggctgggaa    360
ggggtgggtc cggggcggg ctcaggggcg ggctcagggg cggggcgggc gcccgaaggt    420
cctccggagg cccggcattc tcgcacgctt caaaagcgca cgtctgccgc gctgttctcc    480
tcttcctcat ctccgggcct ttcgaccagc ttgatatcga gtgccagcga gtagagtttt    540
ctcctccgag ccgctccgac accgggactg aaaatgagac atattatctg ccacggaggt    600
gttattaccg aagaaatggc cgccagtctt ttggaccagc tgatcgaaga ggtactggct    660
gataatcttc cacctcctag ccatttttgaa ccacctaccc ttcacgaact gtatgattta    720
gacgtgacgg ccccgaaga tcccaacgag gaggcggttt cgcagatttt tcccgactct    780
gtaatgttgg cggtgcagga agggattgac ttactcactt ttccgccggc gcccggttct    840
ccggagccgc ctcacctttc ccggcagccc gagcagccgg agcagagagc cttgggtccg    900
gtttctatgc caaaccttgt accggaggtg atcgatctta cctgccacga ggctggcttt    960
ccacccagtg acgacgagga tgaagagggt gaggagtttg tgttagatta tgtggagcac   1020
cccgggcacg gttgcaggtc ttgtcattat caccggagga atacggggga cccagatatt   1080
atgtgttcgc tttgctatat gaggacctgt ggcatgtttg tctacagtaa gtgaaaatta   1140
tgggcagtgg gtgatagagt ggtgggtttg gtgtggtaat ttttttttta attttttacag   1200 ttttgtggtt taaagaattt tgtattgtga tttttttaaa aggtcctgtg tctgaacctg   1260
agcctgagcc cgagccagaa ccggagcctg caagacctac ccgccgtcct aaaatggcgc   1320
ctgctatcct gagacgcccg acatcacctg tgtctagaga atgcaatagt agtacggata   1380
gctgtgactc cggtccttct aacacacctc ctgagataca cccggtggtc ccgctgtgcc   1440
ccattaaacc agttgccgtg agagttggtg ggcgtcgcca ggctgtggaa tgtatcgagg   1500
```

-continued

```
acttgcttaa cgagcctggg caacctttgg acttgagctg taaacgcccc aggccataag    1560
gtgtaaacct gtgattgcgt gtgtggttaa cgcctttgtt tgctgaatga gttgatgtaa    1620
gtttaataaa gggtgagata atgtttaact tgcatggcgt gttaaatggg gcggggctta    1680
aagggtatat aatgcgccgt gggctaatct tggttacatc tgacctcatg gaggcttggg    1740 agtgttttgga agatttttct gctgtgcgta acttgctgga acagagctct aacagtacct    1800
cttggttttg gaggtttctg tggggctcat cccaggcaaa gttagtctgc agaattaagg    1860
aggattacaa gtgggaattt gaagagcttt tgaaatcctg tggtgagctg tttgattctt    1920
tgaatctggg tcaccaggcg cttttccaag agaaggtcat caagactttg gattttccca    1980
caccggggcg cgctgcggct gctgttgctt ttttgagttt tataaaggat aaatggagcg    2040
aagaaaccca tctgagcggg gggtacctgc tggattttct ggccatgcat ctgtggagag    2100
cggttgtgag acacaagaat cgcctgctac tgttgtcttc cgtccgcccg gcgataatac    2160
cgacggagga gcagcagcag cagcaggagg aagccaggcg gcgcggcag gagcagagcc    2220 catggaaccc gagagccggc ctggaccctc gggaatgaat gttgtacagg tggctgaact    2280
gtatccagaa ctgagacgca ttttgacaat tacagaggat gggcagggc taaaggggt    2340 aaagagggag cgggggggctt gtgaggctac agaggaggct aggaatctag cttttagctt    2400
aatgaccaga caccgtcctg agtgtattac ttttcaacag atcaaggata attgcgctaa    2460
tgagcttgat ctgctggcgc agaagtattc catagagcag ctgaccactt actggctgca    2520
gccaggggat gattttgagg aggctattag ggtatatgca aggtggcac ttaggccaga    2580 ttgcaagtac aagatcagca aacttgtaaa tatcaggaat tgttgctaca tttctgggaa    2640
cggggccgag gtggagatag atacggagga tagggtggcc tttagatgta gcatgataaa    2700
tatgtggccg ggggtgcttg gcatggacgg ggtggttatt atgaatgtaa ggtttactgg    2760
ccccaatttt agcggtacgg ttttcctggc caataccaac cttatcctac acggtgtaag    2820
cttctatggg tttaacaata cctgtgtgga agcctggacc gatgtaaggg ttcggggctg    2880
tgccttttac tgctgctgga aggggtggt gtgtcgcccc aaaagcaggg cttcaattaa    2940
gaaatgcctc tttgaaaggt gtaccttggg tatcctgtct gagggtaact ccagggtgcg    3000
ccacaatgtg gcctccgact gtggttgctt catgctagtg aaaagcgtgg ctgtgattaa    3060
gcataacatg gtatgtggca actgcgagga cagggcctct cagatgctga cctgctcgga    3120
cggcaactgt cacctgctga agaccattca cgtagccagc cactctcgca aggcctggcc    3180
agtgtttgag cataacatac tgacccgctg ttccttgcat ttgggtaaca ggagggggt    3240 gttcctacct taccaatgca atttgagtca cactaagata ttgcttgagc ccgagagcat    3300
gtccaaggtg aacctgaacg gggtgtttga catgaccatg aagatctgga aggtgctgag    3360
gtacgatgag acccgcacca ggtgcagacc ctgcgagtgt ggcggtaaac atattaggaa    3420
ccagcctgtg atgctggatg tgaccgagga gctgaggccc gatcacttgg tgctggcctg    3480
cacccgcgct gagtttggct ctagcgatga agatacagat tgacatatgc aggtacgggg    3540
cctccgcctc cggcacgggc agggctgcct tagtctcccc tccggacacg tgggtctgtg    3600
gtcattctct gtggctgagg ccgagtctca cggtgtctcc cttcaaact gctcacaccc    3660 gtcttgtgtt tttgtctctg gcacagaacc ctccccccacc ttgaattgcc cgtttccata    3720
cagggtctct tccttcggtc ttttgtattt tgattgtta tgtaaaactc gcttttattt    3780
taatattgat gtcagtattt caactgctgt aaaattataa acttttatac ttgggtaagt    3840
cccccagggg cgagttcctc gctctgggat gcaggcatgc ttctcaccgt gcagagctgc    3900
```

```
acttggcctc agctggctgt atggaaatgc accctccctc ctgccgctcc tctctagaac    3960
cttctagaac ctgggctgtg ctgcttttga gcctcagacc ccagggcagc atctcggttc    4020
tgcgccactt cctttgtgtt tatatggcgt tttgtctgtg ttgctgttta gagtaaataa    4080
actgtttata taaaggtttt ggttgcatta ttatcattga aagtgagagg aggcggcctc    4140
ccagtgcccg gccctcccca cccacctgca gccccaccgc gg                      4182
```

<210> SEQ ID NO 6
<211> LENGTH: 4165
<212> TYPE: DNA
<213> ORGANISM: artificial
<220> FEATURE:
<223> OTHER INFORMATION: synthetic

<400> SEQUENCE: 6

```
taccgggtag gggaggcgct tttcccaagg cagtctggag catgcgcttt agcagccccg      60
ctggcacttg cgctacaca agtggcctct ggcctcgcac acattccaca tccaccggta     120
ggcgccaacc ggctccgttc tttggtggcc ccttcgcgcc accttctact cctcccctag     180
tcaggaagtt ccccccgcc ccgcagctcg cgtcgtgcag gacgtgacaa atggaagtag     240
cacgtctcac tagtctcgtg cagatggaca gcaccgctga gcaatggaag cgggtaggcc     300
tttggggcag cggccaatag cagctttgct ccttcgcttt ctgggctcag aggctgggaa     360
ggggtgggtc cggggcgggg ctcaggggcg ggctcagggg cggggcgggc gcccgaaggt     420
cctccggagg cccggcattc tcgcacgctt caaaagcgca cgtctgccgc gctgttctcc     480
tcttcctcat ctccgggcct ttcgaccagc ttgatatcga gtgccagcga gtagagtttt     540
ctcctccgag ccgctccgac accgggactg aaaatgagac atattatctg ccacggaggt     600
gttattaccg aagaaatggc cgccagtctt ttggaccagc tgatcgaaga ggtactggct     660
gataatcttc cacctcctag ccattttgaa ccacctaccc ttcacgaact gtatgattta     720
gacgtgacgg ccccgaaga tcccaacgag gaggcggttt cgcagatttt tcccgactct     780
gtaatgttgg cggtgcagga agggattgac ttactcactt ttccgccggc gcccggttct     840
ccggagccgc ctcaccttc ccggcagccc gagcagccgg agcagagagc cttgggtccg     900
gtttctatgc caaaccttgt accggaggtg atcgatctta cctgccacga ggctggcttt     960
ccacccagtg acgacgagga tgaagagggt gaggagtttg tgttagatta tgtggagcac    1020
cccgggcacg gttgcaggtc ttgtcattat caccggagga atacgggga cccagatatt    1080 atgtgttcgc tttgctatat gaggacctgt ggcatgtttg tctacagtaa gtgaaaatta    1140
tgggcagtgg gtgatagagt ggtgggtttg gtgtggtaat tttttttta atttttacag    1200 ttttgtggtt taaagaattt tgtattgtga ttttttttaaa aggtcctgtg tctgaacctg    1260
agcctgagcc cgagccagaa ccggagcctg caagacctac ccgccgtcct aaaatggcgc    1320
ctgctatcct gagacgcccg acatcacctg tgtctagaga atgcaatagt agtacggata    1380
gctgtgactc cggtccttct aacacacctc ctgagataca cccggtggtc ccgctgtgcc    1440
ccattaaacc agttgccgtg agagttggtg ggcgtcgcca ggctgtggaa tgtatcgagg    1500
acttgcttaa cgagctgggg caaccttggg acttgagctg taaacgcccc aggccataag    1560
gtgtaaacct gtgattgcgt gtgtggttaa cgcctttgtt tgctgaatga gttgatgtaa    1620
gtttaataaa gggtgagata atgtttaact tgcatggcgt gttaaatggg cgggggctta    1680
aagggtatat aatgcgccgt gggctaatct tggttacatc tgacctcatg gaggcttggg    1740
```

```
agtgtttgga agattttcct gctgtgcgta acttgctgga acagagctct aacagtacct    1800
cttggttttg gaggttctg tgggctcat cccaggcaaa gttagtctgc agaattaagg      1860
aggattacaa gtgggaattt gaagagcttt tgaaatcctg tggtgagctg tttgattctt    1920
tgaatctggg tcaccaggcg cttttccaag agaaggtcat caagactttg gattttccca    1980
caccggggcg cgctgcggct gctgttgctt ttttgagttt tataaaggat aaatggagcg    2040
aagaaaccca tctgagcggg gggtacctgc tggattttct ggccatgcat ctgtggagag    2100
cggttgtgag acacaagaat cgcctgctac tgttgtcttc cgtccgcccg gcgataatac    2160
cgacggagga gcagcagcag cagcaggagg aagccaggcg gcggcggcag gagcagagcc    2220
catggaaccc gagagccggc ctggaccctc gggaatgaat gttgtacagg tggctgaact    2280
gtatccagaa ctgagacgca ttttgacaat tacagaggat gggcagggc taaagggggt     2340
aaagagggag cgggggggctt gtgaggctac agaggaggct aggaatctag cttttagctt   2400
aatgaccaga caccgtcctg agtgtattac ttttcaacag atcaaggata attgcgctaa    2460
tgagcttgat ctgctggcgc agaagtattc catagagcag ctgaccactt actggctgca    2520
gccaggggat gattttgagg aggctattag ggtatatgca aggtggcac ttaggccaga     2580
ttgcaagtac aagatcagca aacttgtaaa tatcaggaat gttgctaca tttctgggaa     2640
cggggccgag gtggagatag atacggagga tagggtggcc tttagatgta gcatgataaa    2700
tatgtggccg ggggtgcttg gcatggacgg ggtggttatt atgaatgtaa ggtttactgg    2760
ccccaatttt agcggtacgg ttttcctggc aataccaac cttatcctac acggtgtaag     2820
cttctatggg tttaacaata cctgtgtgga agcctggacc gatgtaaggg ttcggggctg    2880
tgccttttac tgctgctgga aggggtggt gtgtcgcccc aaaagcaggg cttcaattaa     2940
gaaatgcctc tttgaaaggt gtaccttggg tatcctgtct gagggtaact ccagggtgcg    3000
ccacaatgtg gcctccgact gtggttgctt catgctagtg aaaagcgtgg ctgtgattaa    3060
gcataacatg gtatgtggca actgcgagga cagggcctct cagatgctga cctgctcgga    3120
cggcaactgt cacctgctga agaccattca cgtagccagc cactctcgca aggcctggcc    3180
agtgttgag cataacatac tgacccgctg ttccttgcat ttgggtaaca ggagggggt      3240
gttcctacct taccaatgca atttgagtca cactaagata ttgcttgagc ccgagagcat    3300
gtccaaggtg aacctgaacg gggtgtttga catgaccatg aagatctgga aggtgctgag    3360
gtacgatgag acccgcacca ggtgcagacc ctgcgagtgt ggcggtaaac atattaggaa    3420
ccagcctgtg atgctggatg tgaccgagga gctgaggccc gatcacttgg tgctggcctg   3480
cacccgcgct gagtttggct ctagcgatga agatacagat tgacatatgc aggtacgggg    3540
cctccgcctc cggcacgggc agggctgcct tagtctcccc tccggacacg tgggtctgtg    3600
gtcattctct gtggctgagg ccgagtctca cggtgtctcc ctttcaaact gctcacaccc    3660
gtcttgtgtt tttgtctctg gcacagaatt gcccgtttcc atacagggtc tcttccttcg    3720
gtcttttgta ttttgattg ttatgtaaaa ctcgctttta ttttaatatt gatgtcagta     3780
tttcaactgc tgtaaaatta taaacttta tacttgggta agtccccag gggcgagttc      3840
ctcgctctgg gatgcaggca tgcttctcac cgtgcagagc tgcacttggc ctcagctggc    3900
tgtatggaaa tgcaccctcc ctcctgccgc tcctctctag aaccttctag aacctgggct    3960
gtgctgcttt tgagcctcag accccagggc agcatctcgg ttctgcgcca cttcctttgt    4020
gtttatatgc cgtttgtct gtgttgctgt ttagagtaaa taaactgttt atataaaggt     4080
tttggttgca ttattatcat tgaaagtgag aggaggcggc ctcccagtgc ccggccctcc    4140
```

```
ccacccacct gcagccccac cgcgg                                     4165
```

<210> SEQ ID NO 7
<211> LENGTH: 2532
<212> TYPE: DNA
<213> ORGANISM: artificial
<220> FEATURE:
<223> OTHER INFORMATION: synthetic

<400> SEQUENCE: 7

```
tgcatggcgt gttaaatggg gcggggctta aagggtatat aatgcgccgt gggctaatct    60
tggttacatc tgacctcatg gaggcttggg agtgtttgga agattttttct gctgtgcgta   120
acttgctgga acagagctct aacagtacct cttggttttg gaggtttctg tggggctcat   180
cccaggcaaa gttagtctgc agaattaagg aggattacaa gtgggaattt gaagagcttt   240
tgaaatcctg tggtgagctg tttgattctt tgaatctggg tcaccaggcg ctttttccaag  300
agaaggtcat caagactttg gatttttcca caccggggcg cgctgcggct gctgttgctt   360
ttttgagttt tataaaggat aaatggagcg aagaaaccca tctgagcggg gggtacctgc   420
tggattttct ggccatgcat ctgtggagag cggttgtgag acacaagaat cgcctgctac   480
tgttgtcttc cgtccgcccg gcgataatac cgacggagga gcagcagcag cagcaggagg   540
aagccaggcg gcggcggcag gagcagagcc catggaaccc gagagccggc ctggaccctc   600
gggaatgaat gttgtacagg tggctgaact gtatccagaa ctgagacgca ttttgacaat   660
tacagaggat gggcaggggc taaagggggt aaagagggag cgggggggctt gtgaggctac   720
agaggaggct aggaatctag cttttagctt aatgaccaga caccgtcctg agtgtattac   780
ttttcaacag atcaaggata attgcgctaa tgagcttgat ctgctggcgc agaagtattc   840
catagagcag ctgaccactt actggctgca gccagggat gattttgagg aggctattag   900
ggtatatgca aggtggcac ttaggccaga ttgcaagtac aagatcagca aacttgtaaa   960
tatcaggaat tgttgctaca tttctgggaa cggggccgag gtggagatag atacggagga  1020
tagggtggcc tttagatgta gcatgataaa tatgtggccg ggggtgcttg gcatggacgg  1080
ggtggttatt atgaatgtaa ggtttactgg ccccaatttt agcggtacgg ttttcctggc  1140
caataccaac cttatcctac acggtgtaag cttctatggg tttaacaata cctgtgtgga  1200
agcctggacc gatgtaaggg ttcggggctg tgccttttac tgctgctgga aggggggtggt  1260
gtgtcgcccc aaaagcaggg cttcaattaa gaaatgcctc tttgaaaggt gtaccttggg  1320
tatcctgtct gagggtaact ccaggtgcg ccacaatgtg gcctccgact gtggttgctt   1380
catgctagtg aaaagcgtgg ctgtgattaa gcataacatg gtatgtggca actgcgagga  1440
cagggcctct cagatgctga cctgctcgga cggcaactgt cacctgctga agaccattca  1500
cgtagccagc cactctcgca aggcctggcc agtgtttgag cataacatac tgacccgctg  1560
ttccttgcat ttgggtaaca ggagggggt gttcctacct taccaatgca atttgagtca   1620
cactaagata ttgcttgagc ccgagagcat gtccaaggtg aacctgaacg gggtgtttga  1680
catgaccatg aagatctgga aggtgctgag gtacgatgag acccgcacca ggtgcagacc  1740
ctgcgagtgt ggcggtaaac atattaggaa ccagcctgtg atgctggatg tgaccgagga  1800
gctgaggccc gatcacttgg tgctggcctg cacccgcgct gagtttggct ctagcgatga  1860
agatacagat tgcatatatgc aggtacgggg cctccgcctc cggcacgggc agggctgcct  1920
tagtctccc tccggacacg tgggtctgtg gtcattctct gtggctgagg ccgagtctca   1980
```

| | |
|---|---|
| cggtgtctcc ctttcaaact gctcacaccc gtcttgtgtt tttgtctctg gcacagaacc | 2040 |
| ctcccccacc ttgaattgcc cgtttccata cagggtctct tccttcggtc ttttgtattt | 2100 |
| ttgattgtta tgtaaaactc gcttttattt taatattgat gtcagtattt caactgctgt | 2160 |
| aaaattataa acttttatac ttgggtaagt cccccagggg cgagttcctc gctctgggat | 2220 |
| gcaggcatgc ttctcaccgt gcagagctgc acttggcctc agctggctgt atggaaatgc | 2280 |
| accctccctc ctgccgctcc tctctagaac cttctagaac ctgggctgtg ctgcttttga | 2340 |
| gcctcagacc ccagggcagc atctcggttc tgcgccactt cctttgtgtt tatatggcgt | 2400 |
| tttgtctgtg ttgctgttta gagtaaataa actgtttata taaaggtttt ggttgcatta | 2460 |
| ttatcattga aagtgagagg aggcggcctc ccagtgcccg gccctcccca cccacctgca | 2520 |
| gccccaccgc gg | 2532 |

<210> SEQ ID NO 8
<211> LENGTH: 2037
<212> TYPE: DNA
<213> ORGANISM: artificial
<220> FEATURE:
<223> OTHER INFORMATION: synthetic

<400> SEQUENCE: 8

| | |
|---|---|
| taccgggtag gggaggcgct tttcccaagg cagtctggag catgcgcttt agcagccccg | 60 |
| ctggcacttg gcgctacaca gtggcctct ggcctcgcac acattccaca tccaccggta | 120 |
| ggcgccaacc ggctccgttc tttggtggcc ccttcgcgcc accttctact cctcccctag | 180 |
| tcaggaagtt ccccccgcc ccgcagctcg cgtcgtgcag gacgtgacaa atggaagtag | 240 |
| cacgtctcac tagtctcgtg cagatggaca gcaccgctga gcaatggaag cgggtaggcc | 300 |
| tttggggcag cggccaatag cagctttgct ccttcgcttt ctgggctcag aggctgggaa | 360 |
| ggggtgggtc cggggggcggg ctcaggggcg ggctcagggg cggggcgggc gcccgaaggt | 420 |
| cctccggagg cccggcattc tcgcacgctt caaaagcgca cgtctgccgc gctgttctcc | 480 |
| tcttcctcat ctccgggcct ttcgaccagc ttgatatcga gtgccagcga gtagagtttt | 540 |
| ctcctccgag ccgctccgac accgggactg aaaatgagac atattatctg ccacggaggt | 600 |
| gttattaccg aagaaatggc cgccagtctt ttggaccagc tgatcgaaga ggtactggct | 660 |
| gataatcttc cacctcctag ccattttgaa ccacctaccc ttcacgaact gtatgattta | 720 |
| gacgtgacgg ccccgaaga tcccaacgag gaggcggttt cgcagatttt tcccgactct | 780 |
| gtaatgttgg cggtgcagga agggattgac ttactcactt ttccgccggc gcccggttct | 840 |
| ccggagccgc ctcacctttc ccggcagccc gagcagccgg agcagagagc cttgggtccg | 900 |
| gtttctatgc caaaccttgt accggaggtg atcgatctta cctgccacga ggctggcttt | 960 |
| ccacccagtg acgacgagga tgaagagggt gaggagtttg tgttagatta tgtggagcac | 1020 |
| cccgggcacg gttgcaggtc ttgtcattat caccggagga atacggggga cccagatatt | 1080 |
| atgtgttcgc tttgctatat gaggacctgt ggcatgtttg tctacagtaa gtgaaaatta | 1140 |
| tgggcagtgg gtgatagagt ggtgggtttg tgtgtggtaat tttttttttta attttttacag | 1200 |
| ttttgtggtt taaagaattt tgtattgtga tttttttaaa aggtcctgtg tctgaacctg | 1260 |
| agcctgagcc cgagccagaa ccggagcctg caagacctac ccgccgtcct aaaatggcgc | 1320 |
| ctgctatcct gagacgcccg acatcacctg tgtctagaga atgcaatagt agtacggata | 1380 |
| gctgtgactc cggtccttct aacacacctc ctgagataca cccggtggtc ccgctgtgcc | 1440 |
| ccattaaacc agttgccgtg agagttggtg ggcgtcgcca ggctgtggaa tgtatcgagg | 1500 |

```
acttgcttaa cgagcctggg caacctttgg acttgagctg taaacgcccc aggccataaa    1560
ttgcccgttt ccatacaggg tctcttcctt cggtcttttg tattttttgat tgttatgtaa   1620 aactcgcttt tattttaata ttgatgtcag tatttcaact gctgtaaaat tataaacttt    1680
tatacttggg taagtcccccc aggggcgagt tcctcgctct gggatgcagg catgcttctc   1740
accgtgcaga gctgcacttg gcctcagctg gctgtatgga aatgcaccct ccctcctgcc    1800
gctcctctct agaaccttct agaacctggg ctgtgctgct tttgagcctc agaccccagg    1860
tcagcatctc ggttctgcgc cacttccttt gtgtttatat ggcgttttgt ctgtgttgct    1920
gtttagagta aataaactgt ttatataaag gttttggttg cattattatc attgaaagtg    1980
agaggaggcg gcctcccagt gcccggccct ccccacccac ctgcagcccc accgcgg       2037

<210> SEQ ID NO 9
<211> LENGTH: 7108
<212> TYPE: DNA
<213> ORGANISM: artificial
<220> FEATURE:
<223> OTHER INFORMATION: synthetic

<400> SEQUENCE: 9
gtggcacttt tcggggaaat gtgcgcggaa cccctatttg tttattttttc taaatacatt    60 caaatatgta tccgctcatg agacaataac cctgataaat gcttcaataa tattgaaaaa    120
ggaagagtat gagtattcaa catttccgtg tcgcccttat ccctttttttt gcggcatttt    180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacgatggc atgcagtaa     480 gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt    1020
agattgattt aaaacttcat ttttaattta aaaggatcta ggtgaagatc cttttttgata   1080 atctcatgac caaaatccct taacgtgagt tttcgttcca ctgagcgtca gaccccgtag    1140
aaaagatcaa aggatcttct tgagatcctt ttttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
```

```
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggccttt tacggttcct ggcttttgc tggcttttg      1800 ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccggg ccccccctcg   2220
aggtcatcga attctaccgg gtaggggagg cgcttttccc aaggcagtct ggagcatgcg   2280
ctttagcagc cccgctggca cttggcgcta cacaagtggc ctctggcctc gcacacattc   2340
cacatccacc ggtaggcgcc aaccggctcc gttctttggt ggccccttcg cgccaccttc   2400
tactcctccc ctagtcagga agttccccc cgccccgcag ctcgcgtcgt gcaggacgtg    2460
acaaatggaa gtagcacgtc tcactagtct cgtgcagatg gacagcaccg ctgagcaatg   2520
gaagcgggta ggcctttggg gcagcggcca atagcagctt tgctccttcg ctttctgggc   2580
tcagaggctg gaagggggtg gtccggggg cgggctcagg ggcgggctca ggggcggggc    2640
gggcgcccga aggtcctccg gaggcccggc attctcgcac gcttcaaaag cgcacgtctg   2700
ccgcgctgtt ctcctcttcc tcatctccgg gcctttcgac cagcttgata tcgagtgcca   2760
gcgagtagag ttttctcctc cgagccgctc cgacaccggg actgaaaatg agacatatta   2820
tctgccacgg aggtgttatt accgaagaaa tggccgccag tcttttggac cagctgatcg   2880
aagaggtact ggctgataat cttccacctc ctagccattt tgaaccacct cccttcacg    2940 aactgtatga tttagacgtg acggcccccg aagatcccaa cgaggaggcg gtttcgcaga   3000
ttttttccga ctctgtaatg ttggcggtgc aggaagggat tgacttactc acttttccgc   3060
cggcgccccg ttctccggag ccgcctcacc tttcccggca gcccgagcag ccggagcaga   3120
gagccttggg tccggtttct atgccaaacc ttgtaccgga ggtgatcgat cttacctgcc   3180
acgaggctgg ctttccaccc agtgacgacg aggatgaaga gggtgaggag tttgtgttag   3240
attatgtgga gcaccccggg cacggttgca ggtcttgtca ttatcaccgg aggaatacgg   3300
gggacccaga tattatgtgt tcgctttgct atatgaggac ctgtggcatg tttgtctaca   3360
gtaagtgaaa attatgggca gtgggtgata gagtggtggg tttggtgtgg taattttttt   3420 tttaatttt acagttttgt ggtttaaaga attttgtatt gtgattttt taaaaggtcc     3480 tgtgtctgaa cctgagcctg agcccgagcc agaaccggag cctgcaagac ctacccgccg   3540
tcctaaaatg gcgcctgcta tcctgagacg cccgacatca cctgtgtcta gagaatgcaa   3600
tagtagtacg gatagctgtg actccggtcc ttctaacaca cctcctgaga tacacccggt   3660
ggtcccgctg tgccccatta aaccagttgc cgtgagagtt ggtgggcgtc gccaggctgt   3720
ggaatgtatc gaggacttgc ttaacgagcc tgggcaacct ttggacttga gctgtaaacg   3780
ccccaggcca taaggtgtaa acctgtgatt gcgtgtgtgg ttaacgcctt tgtttgctga   3840
atgagttgat gtaagtttaa taaagggtga gataatgttt aacttgcatg gcgtgttaaa   3900
```

```
tggggcgggg cttaaagggt atataatgcg ccgtgggcta atcttggtta catctgacct    3960
catgaggct  tgggagtgtt tggaagattt ttctgctgtg cgtaacttgc tggaacagag    4020
ctctaacagt acctcttggt tttggaggtt tctgtggggc tcatcccagg caaagttagt    4080
ctgcagaatt aaggaggatt acaagtggga atttgaagag cttttgaaat cctgtggtga    4140
gctgtttgat tctttgaatc tgggtcacca ggcgcttttc caagagaagg tcatcaagac    4200
tttggatttt tccacaccgg ggcgcgctgc ggctgctgtt gcttttttga gttttataaa    4260
ggataaatgg agcgaagaaa cccatctgag cgggggggtac ctgctggatt ttctggccat    4320
gcatctgtgg agagcggttg tgagacacaa gaatcgcctg ctactgttgt cttccgtccg    4380
cccggcgata taccgacgg aggagcagca gcagcagcag gaggaagcca ggcggcggcg     4440
gcaggagcag agcccatgga acccgagagc cggcctggac cctcgggaat gaatgttgta    4500
caggtggctg aactgtatcc agaactgaga cgcattttga caattacaga ggatgggcag    4560
gggctaaagg gggtaaagag ggagcggggg gcttgtgagg ctacagagga ggctaggaat    4620
ctagctttta gcttaatgac cagacaccgt cctgagtgta ttacttttca acagatcaag    4680
gataattgcg ctaatgagct tgatctgctg gcgcagaagt attccataga gcagctgacc    4740
acttactggc tgcagccagg ggatgatttt gaggaggcta ttagggtata tgcaaaggtg    4800
gcacttaggc cagattgcaa gtacaagatc agcaaacttg taaatatcag gaattgttgc    4860
tacatttctg gaacggggc cgaggtggag atagatacgg aggatagggt ggcctttaga     4920
tgtagcatga taaatatgtg gccgggggtg cttggcatgg acggggtggt tattatgaat    4980
gtaaggttta ctggccccaa ttttagcggt acggttttcc tggccaatac caaccttatc    5040
ctacacggtg taagcttcta tgggtttaac aatacctgtg tggaagcctg gaccgatgta    5100
agggttcggg gctgtgcctt ttactgctgc tggaagggg tggtgtgtcg ccccaaaagc     5160
agggcttcaa ttaagaaatg cctctttgaa aggtgtacct tgggtatcct gtctgagggt    5220
aactccaggg tgcgccacaa tgtggcctcc gactgtggtt gcttcatgct agtgaaaagc    5280
gtggctgtga ttaagcataa catggtatgt ggcaactgcg aggacagggc ctctcagatg    5340
ctgacctgct cggacggcaa ctgtcacctg ctgaagacca ttcacgtagc cagccactct    5400
cgcaaggcct ggccagtgtt tgagcataac atactgaccc gctgttcctt gcatttgggt    5460
aacaggaggg gggtgttcct accttaccaa tgcaatttga gtcacactaa gatattgctt    5520
gagcccgaga gcatgtccaa ggtgaacctg aacggggtgt ttgacatgac catgaagatc    5580
tggaaggtgc tgaggtacga tgagacccgc accaggtgca gaccctgcga gtgtggcggt    5640
aaacatatta ggaaccagcc tgtgatgctg gatgtgaccg aggagctgag gcccgatcac    5700
ttggtgctgg cctgcacccg cgctgagttt ggctctagcg atgaagatac agattgacat    5760
atgcaggtac ggggcctccg cctccggcac gggcagggct gccttagtct ccctccgga    5820
cacgtgggtc tgtggtcatt tctctgtgct gaggccgagt ctcacggtgt ctcccttca    5880
aactgctcac acccgtcttg tgttttgtc tctggcacag aaccctcccc caccttgaat    5940
tgcccgtttc catacagggt ctcttccttc ggtctttgt attttgatt gttatgtaaa     6000
actcgctttt attttaatat tgatgtcagt atttcaactg ctgtaaaatt ataaactttt    6060
atacttgggt aagtccccca ggggcgagtt cctcgctctg ggatgcaggc atgcttctca    6120
ccgtgcagag ctgcacttgg cctcagctgg ctgtatggaa atgcaccctc cctcctgccg    6180
ctcctctcta gaaccttcta gaacctgggc tgtgctgctt ttgagcctca gaccccaggg    6240
```

```
cagcatctcg gttctgcgcc acttcctttg tgtttatatg gcgttttgtc tgtgttgctg    6300
tttagagtaa ataaactgtt tatataaagg ttttggttgc attattatca ttgaaagtga    6360
gaggaggcgg cctcccagtg cccggccctc cccacccacc tgcagcccca ccgcggatcc    6420
actagttcta gagcggccgc caccgcggtg gagctccaat cgccctata gtgagtcgta    6480 ttacgcgcgc tcactggccg tcgttttaca acgtcgtgac tgggaaaacc ctggcgttac    6540
ccaacttaat cgccttgcag cacatccccc tttcgccagc tggcgtaata gcgaagaggc    6600
ccgcaccgat cgcccttccc aacagttgcg cagcctgaat ggcgaatggg acgcgccctg    6660
tagcggcgca ttaagcgcgg cgggtgtggt ggttacgcgc agcgtgaccg ctacacttgc    6720
cagcgcccta gcgcccgctc ctttcgcttt cttcccttcc tttctcgcca cgttcgccgg    6780
ctttccccgt caagctctaa atcggggggct cctttaggg ttccgattta gtgctttacg    6840
gcacctcgac cccaaaaaac ttgattaggg tgatggttca cgtagtgggc catcgccctg    6900
atagacggtt tttcgccctt tgacgttgga gtccacgttc tttaatagtg gactcttgtt    6960
ccaaactgga acaacactca accctatctc ggtctattct tttgatttat aagggatttt    7020
gccgatttcg gcctattggt taaaaaatga gctgatttaa caaaaattta acgcgaattt    7080
taacaaaata ttaacgctta caatttag                                       7108

<210> SEQ ID NO 10
<211> LENGTH: 154
<212> TYPE: DNA
<213> ORGANISM: artificial
<220> FEATURE:
<223> OTHER INFORMATION: synthetic

<400> SEQUENCE: 10
gtacggggcc tccgcctccg gcaccggcag ggctgcctta gtctcccctc cggacacgtg     60
ggtctgtggt cattctctgt ggctgaggcc gagtctcacg gtgtctccct ttcaaactgc    120
tcacacccgt cttgtgtttt tgtctctggc acag                                154

<210> SEQ ID NO 11
<211> LENGTH: 9
<212> TYPE: DNA
<213> ORGANISM: artificial
<220> FEATURE:
<223> OTHER INFORMATION: synthetic

<400> SEQUENCE: 11 caggtacgg                                                              9

<210> SEQ ID NO 12
<211> LENGTH: 15
<212> TYPE: DNA
<213> ORGANISM: artificial
<220> FEATURE:
<223> OTHER INFORMATION: synthetic

<400> SEQUENCE: 12
tgtctctggc acaga                                                       15

<210> SEQ ID NO 13
<211> LENGTH: 158
<212> TYPE: DNA
<213> ORGANISM: artificial
<220> FEATURE:
<223> OTHER INFORMATION: synthetic

<400> SEQUENCE: 13
```
caggtacggg gcctccgcct ccggcaccgg cagggctgcc ttagtctccc ctccggacac    60
gtgggtctgt ggtcattctc tgtggctgag gccgagtctc acggtgtctc cctttcaaac   120
tgctcacacc cgtcttgtgt ttttgtctct ggcacaga                           158

<210> SEQ ID NO 14
<211> LENGTH: 481
<212> TYPE: DNA
<213> ORGANISM: artificial
<220> FEATURE:
<223> OTHER INFORMATION: synthetic

<400> SEQUENCE: 14
tgaattgccc gtttccatac agggtctctt ccttcggtct tttgtatttt tgattgttat    60
gtaaaactcg ctttttatttt aatattgatg tcagtatttc aactgctgta aaattataaa   120
cttttatact tgggtaagtc ccccaggggc gagttcctcg ctctgggatg caggcatgct   180
tctcaccgtg cagagctgca cttggcctca gctggctgta tggaaatgca ccctccctcc   240
tgccgctcct ctctagaacc ttctagaacc tgggctgtgc tgcttttgag cctcagaccc   300
caggtcagca tctcggttct gcgccacttc ctttgtgttt atatggcgtt ttgtctgtgt   360
tgctgtttag agtaaataaa ctgtttatat aaaggttttg gttgcattat tatcattgaa   420
agtgagagga ggcggcctcc cagtgcccgg ccctccccac ccacctgcag ccccaccgcg   480
g                                                                  481

<210> SEQ ID NO 15
<211> LENGTH: 4007
<212> TYPE: DNA
<213> ORGANISM: artificial
<220> FEATURE:
<223> OTHER INFORMATION: synthetic

<400> SEQUENCE: 15
tcgagtttac tccctatcag tgatagagaa cgtatgtcga gtttactccc tatcagtgat    60
agagaacgat gtcgagttta ctccctatca gtgatagaga acgtatgtcg agtttactcc   120
ctatcagtga tagagaacgt atgtcgagtt tactccctat cagtgataga gaacgtatgt   180
cgagtttatc cctatcagtg atagagaacg tatgtcgagt ttactcccta tcagtgatag   240
agaacgtatg tcgaggtagg cgtgtacggt gggaggccta tataagcaga gctcgtttag   300
tgaaccgtca gatcgcctgg agaattcgag ctcggtaccc atcgagtgcc agcgagtaga   360
gttttctcct ccgagccgct ccgacaccgg gactgaaaat gagacatatt atctgccacg   420
gaggtgttat taccgaagaa atggccgcca gtcttttgga ccagctgatc gaagaggtac   480
tggctgataa tcttccacct cctagccatt ttgaaccacc tacccttcac gaactgtatg   540
atttagacgt gacggccccc gaagatccca acgaggaggc ggtttcgcag attttttccg   600
actctgtaat gttggcggtg caggaaggga ttgacttact cacttttccg ccggcgcccg   660
gttctccgga gccgcctcac ctttcccggc agcccgagca gccggagcag agagccttgg   720
gtccggtttc tatgccaaac cttgtaccgg aggtgatcga tcttacctgc cacgaggctg   780
gctttccacc cagtgacgac gaggatgaag agggtgagga gtttgtgtta gattatgtgg   840
agcaccccgg gcacggttgc aggtcttgtc attatcaccg gaggaatacg ggggacccag   900
atattatgtg ttcgctttgc tatatgagga cctgtggcat gtttgtctac agtaagtgaa   960
aattatgggc agtgggtgat agagtggtgg gtttggtgtg gtaattttttt ttttaatttt  1020

```
tacagttttg tggtttaaag aattttgtat tgtgattttt ttaaaaggtc ctgtgtctga    1080
acctgagcct gagcccgagc cagaaccgga gcctgcaaga cctacccgcc gtcctaaaat    1140
ggcgcctgct atcctgagac gcccgacatc acctgtgtct agagaatgca atagtagtac    1200
ggatagctgt gactccggtc cttctaacac acctcctgag atacacccgg tggtcccgct    1260
gtgccccatt aaaccagttg ccgtgagagt tggtgggcgt cgccaggctg tggaatgtat    1320
cgaggacttg cttaacgagc ctgggcaacc tttggacttg agctgtaaac gccccaggcc    1380
ataaggtgta aacctgtgat tgcgtgtgtg gttaacgcct ttgtttgctg aatgagttga    1440
tgtaagttta ataaagggtg agataatgtt aacttgcat ggcgtgttaa atggggcggg     1500
gcttaaaggg tatataatgc gccgtgggct aatcttggtt acatctgacc tcatggaggc    1560
ttgggagtgt ttggaagatt tttctgctgt gcgtaacttg ctggaacaga gctctaacag    1620
tacctcttgg ttttggaggt ttctgtgggg ctcatcccag gcaaagttag tctgcagaat    1680
taaggaggat tacaagtggg aatttgaaga gcttttgaaa tcctgtggtg agctgtttga    1740
ttctttgaat ctgggtcacc aggcgctttt ccaagagaag gtcatcaaga ctttggattt    1800
ttccacaccg gggcgcgctg cggctgctgt tgcttttttg agttttataa aggataaatg    1860
gagcgaagaa acccatctga gcggggggta cctgctggat tttctggcca tgcatctgtg    1920
gagagcggtt gtgagacaca agaatcgcct gctactgttg tcttccgtcc gcccggcgat    1980
aataccgacg gaggagcagc agcagcagca ggaggaagcc aggcggcggc ggcaggagca    2040
gagcccatgg aacccgagag ccggcctgga ccctcgggaa tgaatgttgt acaggtggct    2100
gaactgtatc cagaactgag acgcattttg acaattacag aggatgggca ggggctaaag    2160
ggggtaaaga gggagcgggg ggcttgtgag gctacagagg aggctaggaa tctagctttt    2220
agcttaatga ccagacaccg tcctgagtgt attactttc aacagatcaa ggataattgc     2280
gctaatgagc ttgatctgct ggcgcagaag tattccatag agcagctgac cacttactgg    2340
ctgcagccag gggatgattt tgaggaggct attagggtat atgcaaaggt ggcacttagg    2400
ccagattgca agtacaagat cagcaaactt gtaaatatca ggaattgttg ctacatttct    2460
gggaacgggg ccgaggtgga gatagatacg gaggataggg tggcctttag atgtagcatg    2520
ataaatatgt ggccggggt gcttggcatg acggggtgg ttattatgaa tgtaaggttt      2580
actggcccca atttagcgg tacggttttc ctggccaata ccaaccttat cctacacggt     2640
gtaagcttct atgggtttaa caatacctgt gtggaagcct ggaccgatgt aagggttcgg    2700
ggctgtgcct tttactgctg ctggaagggg gtggtgtgtc gccccaaaag cagggcttca    2760
attaagaaat gcctctttga aaggtgtacc ttgggtatcc tgtctgaggg taactccagg    2820
gtgcgccaca atgtggcctc cgactgtggt tgcttcatgc tagtgaaaag cgtggctgtg    2880
attaagcata acatggtatg tggcaactgc gaggacaggg cctctcagat gctgacctgc    2940
tcggacggca actgtcacct gctgaagacc attcacgtag ccagccactc tcgcaaggcc    3000
tggccagtgt ttgagcataa catactgacc cgctgttcct tgcatttggg taacaggagg    3060
ggggtgttcc taccttacca atgcaatttg agtcacacta agatattgct tgagcccgag    3120
agcatgtcca aggtgaacct gaacggggtg tttgacatga ccatgaagat ctggaaggtg    3180
ctgaggtacg atgagacccg caccaggtgc agaccctgcg agtgtggcgg taaacatatt    3240
aggaaccagc ctgtgatgct ggatgtgacc gaggagctga ggcccgatca cttggtgctg    3300
gcctgcaccc gcgctgagtt tggctctagc gatgaagata cagattgaca tatgcaggta    3360
cggggcctcc gcctccggca cgggcagggc tgccttagtc tcccctccgg acacgtgggt    3420
```

```
ctgtggtcat tctctgtggc tgaggccgag tctcacggtg tctcccttc aaactgctca    3480 cacccgtctt gtgttttgt ctctggcaca gaaccctccc ccaccttgaa ttgcccgttt    3540
ccatacaggg tctcttcctt cggtcttttg tattttgat tgttatgtaa aactcgcttt    3600
tattttaata ttgatgtcag tatttcaact gctgtaaaat tataaacttt tatacttggg    3660 taagtcccc aggggcgagt tcctcgctct gggatgcagg catgcttctc accgtgcaga    3720
gctgcacttg gcctcagctg gctgtatgga aatgcaccct ccctcctgcc gctcctctct    3780
agaaccttct agaacctggg ctgtgctgct tttgagcctc agaccccagg gcagcatctc    3840
ggttctgcgc cacttccttt gtgtttatat ggcgttttgt ctgtgttgct gtttagagta    3900
aataaactgt ttatataaag gttttggttg cattattatc attgaaagtg agaggaggcg    3960
gcctcccagt gccggccct ccccacccac ctgcagcccc accgcgg                  4007
```

<210> SEQ ID NO 16  
<211> LENGTH: 496  
<212> TYPE: PRT  
<213> ORGANISM: artificial  
<220> FEATURE:  
<223> OTHER INFORMATION: synthetic

<400> SEQUENCE: 16

```
Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
    50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
    130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
    210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255
```

| | | | | | | | | | | | |
|---|---|---|---|---|---|---|---|---|---|---|---|
|Leu|Ile|Leu|His|Gly|Val|Ser|Phe|Tyr|Gly|Phe|Asn Asn Thr Cys Val|
| | | |260| | |265| | | |270| |

Glu Ala Trp Thr Asp Val Arg Val Arg Gly Cys Ala Phe Tyr Cys Cys
          275                 280                 285

Trp Lys Gly Val Val Cys Arg Pro Lys Ser Arg Ala Ser Ile Lys Lys
          290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
              325                 330                 335

Lys Ser Val Ala Val Ile Lys His Asn Met Val Cys Gly Asn Cys Glu
              340                 345                 350

Asp Arg Ala Ser Gln Met Leu Thr Cys Ser Asp Gly Asn Cys His Leu
              355                 360                 365

Leu Lys Thr Ile His Val Ala Ser His Ser Arg Lys Ala Trp Pro Val
          370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
              405                 410                 415

Leu Leu Glu Pro Glu Ser Met Ser Lys Val Asn Leu Asn Gly Val Phe
              420                 425                 430

Asp Met Thr Met Lys Ile Trp Lys Val Leu Arg Tyr Asp Glu Thr Arg
              435                 440                 445

Thr Arg Cys Arg Pro Cys Glu Cys Gly Gly Lys His Ile Arg Asn Gln
          450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
              485                 490                 495

```
<210> SEQ ID NO 17
<211> LENGTH: 1491
<212> TYPE: DNA
<213> ORGANISM: Adenovirus serotype 5

<400> SEQUENCE: 17
atggagcgaa gaaacccatc tgagcggggg gtacctgctg attttctgg ccatgcatct      60 gtggagagcg ttgtgagac acaagaatcg cctgctactg ttgtcttccg tccgcccggc     120
gataataccg acggaggagc agcagcagca gcaggaggaa gccaggcggc ggcggcagga    180
gcagagccca tggaacccga gagccggcct ggaccctcgg gaatgaatgt tgtacaggtg    240
gctgaactgt atccagaact gagacgcatt ttgacaatta cagaggatgg gcaggggcta    300 aaggggtaa agagggagcg gggggcttgt gaggctacag aggaggctag gaatctagct    360
tttagcttaa tgaccagaca ccgtcctgag tgtattactt tcaacagat caaggataat    420 tgcgctaatg agcttgatct gctggcgcag aagtattcca tagagcagct gaccacttac    480
tggctgcagc caggggatga ttttgaggag gctattaggg tatatgcaaa ggtggcactt    540
aggccagatt gcaagtacaa gatcagcaaa cttgtaaata tcaggaattg ttgctacatt    600
tctgggaacg gggccgaggt ggagatagat acggaggata gggtggcctt tagatgtagc    660
atgataaata tgtggccggg ggtgcttggc atggacgggg tggttattat gaatgtaagg    720
tttactggcc ccaattttag cggtacggtt ttcctggcca taccaacct tatcctacac    780
```

| | |
|---|---|
| ggtgtaagct tctatgggtt taacaatacc tgtgtggaag cctggaccga tgtaagggtt | 840 |
| cggggctgtg cctttttactg ctgctggaag ggggtggtgt gtcgcccaa aagcagggct | 900 |
| tcaattaaga aatgcctctt tgaaaggtgt accttgggta tcctgtctga gggtaactcc | 960 |
| agggtgcgcc acaatgtggc ctccgactgt ggttgcttca tgctagtgaa aagcgtggct | 1020 |
| gtgattaagc ataacatggt atgtggcaac tgcgaggaca gggcctctca gatgctgacc | 1080 |
| tgctcggacg gcaactgtca cctgctgaag accattcacg tagccagcca ctctcgcaag | 1140 |
| gcctggccag tgtttgagca taacatactg acccgctgtt ccttgcattt gggtaacagg | 1200 |
| agggggtgt tcctaccta ccaatgcaat ttgagtcaca ctaagatatt gcttgagccc | 1260 |
| gagagcatgt ccaaggtgaa cctgaacggg gtgtttgaca tgaccatgaa gatctggaag | 1320 |
| gtgctgaggt acgatgagac ccgcaccagg tgcagaccct gcgagtgtgg cggtaaacat | 1380 |
| attaggaacc agcctgtgat gctggatgtg accgaggagc tgaggcccga tcacttggtg | 1440 |
| ctggcctgca cccgcgctga gtttggctct agcgatgaag atacagattg a | 1491 |

<210> SEQ ID NO 18
<211> LENGTH: 176
<212> TYPE: PRT
<213> ORGANISM: Adenovirus serotype 5

<400> SEQUENCE: 18

Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Leu Ser Ser Val Arg Pro Ala Ile Ile
    130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
                165                 170                 175

<210> SEQ ID NO 19
<211> LENGTH: 531
<212> TYPE: DNA
<213> ORGANISM: Adenovirus serotype 5

<400> SEQUENCE: 19

| | |
|---|---|
| atggaggctt gggagtgttt ggaagatttt tctgctgtgc gtaacttgct ggaacagagc | 60 |
| tctaacagta cctcttggtt tttggaggttt ctgtggggct catcccaggc aaagttagtc | 120 |
| tgcagaatta aggaggatta caagtgggaa tttgaagagc ttttgaaatc ctgtggtgag | 180 |

```
ctgtttgatt ctttgaatct gggtcaccag gcgcttttcc aagagaaggt catcaagact      240
ttggattttt ccacaccggg gcgcgctgcg gctgctgttg ctttttttgag ttttataaag     300 gataaatgga gcgaagaaac ccatctgagc gggggggtacc tgctggattt tctggccatg    360
catctgtgga gagcggttgt gagacacaag aatcgcctgc tactgttgtc ttccgtccgc     420
ccggcgataa taccgacgga ggagcagcag cagcagcagg aggaagccag gcggcggcgg     480
caggagcaga gcccatggaa cccgagagcc ggcctggacc ctcgggaatg a              531
```

<210> SEQ ID NO 20
<211> LENGTH: 84
<212> TYPE: PRT
<213> ORGANISM: Adenovirus serotype 5

<400> SEQUENCE: 20

```
Met Glu Arg Arg Asn Pro Ser Glu Arg Gly Val Pro Ala Gly Phe Ser
 1               5                  10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Ala Gly Ala Glu Pro Met
    50                  55                  60

Glu Pro Glu Ser Arg Pro Gly Pro Ser Gly Met Asn Val Val Gln Gln
65                  70                  75                  80

Pro Pro Pro Pro
```

<210> SEQ ID NO 21
<211> LENGTH: 255
<212> TYPE: DNA
<213> ORGANISM: Adenovirus serotype 5

<400> SEQUENCE: 21

```
atggagcgaa gaaacccatc tgagcggggg gtacctgctg gattttctgg ccatgcatct      60
gtggagagcg gttgtgagac acaagaatcg cctgctactg ttgtcttccg tccgccggc     120 gataataccg acggaggagc agcagcagca gcaggaggaa gccaggcggc ggcggcagga    180
gcagagccca tggaacccga gagccggcct ggaccctcgg gaatgaatgt tgtacagcag    240
ccgccgccgc catga                                                      255
```

<210> SEQ ID NO 22
<211> LENGTH: 7091
<212> TYPE: DNA
<213> ORGANISM: artificial
<220> FEATURE:
<223> OTHER INFORMATION: synthetic

<400> SEQUENCE: 22

```
gtggcacttt tcggggaaat gtgcgcggaa cccctatttg tttatttttc taaatacatt      60
caaatatgta tccgctcatg agacaataac cctgataaat gcttcaataa tattgaaaaa    120
ggaagagtat gagtattcaa catttccgtg tcgcccttat cccttttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
```

```
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca acacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt    1020
agattgattt aaaacttcat ttttaattta aaaggatcta ggtgaagatc ctttttgata    1080
atctcatgac caaaatccct taacgtgagt tttcgttcca ctgagcgtca gaccccgtag    1140
aaaagatcaa aggatcttct tgagatcctt ttttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcggc agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatggaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct gggtaccggg ccccccctcg    2220
aggtcatcga attctaccgg gtaggggagg cgcttttccc aaggcagtct ggagcatgcg    2280
ctttagcagc cccgctggca cttggcgcta cacaagtggc ctctggcctc gcacacattc    2340
cacatccacc ggtaggcgcc aaccggctcc gttctttggt ggccccttcg cgccaccttc    2400
tactcctccc ctagtcagga gttcccccc cgccccgcag ctcgcgtcgt gcaggacgtg    2460
acaaatggaa gtagcacgtc tcactagtct cgtgcagatg gacagcaccg ctgagcaatg    2520
gaagcgggta ggcctttggg gcagcggcca atagcagctt tgctccttcg ctttctgggc    2580
tcagaggctg ggaaggggtg ggtccggggg cgggctcagg ggcgggctca ggggcggggc    2640
gggcgcccga aggtcctccg gaggcccggc attctcgcac gcttcaaaag cgcacgtctg    2700
ccgcgctgtt ctcctcttcc tcatctccgg gcctttcgac cagcttgata tcgagtgcca    2760
gcgagtagag tttttctcctc cgagccgctc cgacaccggg actgaaaatg agacatatta    2820
```

```
tctgccacgg aggtgttatt accgaagaaa tggccgccag tcttttggac cagctgatcg    2880
aagaggtact ggctgataat cttccacctc ctagccattt tgaaccacct acccttcacg    2940
aactgtatga tttagacgtg acggcccccg aagatcccaa cgaggaggcg gtttcgcaga    3000 ttttcccga ctctgtaatg ttggcggtgc aggaagggat tgacttactc acttttccgc     3060
cggcgcccgg ttctccggag ccgcctcacc tttcccggca gcccgagcag ccggagcaga    3120
gagccttggg tccggtttct atgccaaacc ttgtaccgga ggtgatcgat cttacctgcc    3180
acgaggctgg ctttccaccc agtgacgacg aggatgaaga gggtgaggag tttgtgttag    3240
attatgtgga gcaccccggg cacgttgca ggtcttgtca ttatcaccgg aggaatacgg      3300
gggacccaga tattatgtgt tcgctttgct atatgaggac ctgtggcatg tttgtctaca    3360
gtaagtgaaa attatgggca gtgggtgata gagtggtggg tttggtgtgg taattttttt    3420
tttaattttt acagttttgt ggtttaaaga attttgtatt gtgattttttt taaaaggtcc   3480 tgtgtctgaa cctgagcctg agcccgagcc agaaccggag cctgcaagac ctacccgccg   3540
tcctaaaatg gcgcctgcta tcctgagacg cccgacatca cctgtgtcta gagaatgcaa   3600
tagtagtacg gatagctgtg actccggtcc ttctaacaca cctcctgaga tacacccggt   3660
ggtcccgctg tgccccatta aaccagttgc cgtgagagtt ggtgggcgtc gccaggctgt   3720
ggaatgtatc gaggacttgc ttaacgagcc tgggcaacct ttggacttga gctgtaaacg   3780
ccccaggcca taaggtgtaa acctgtgatt gcgtgtgtgg ttaacgcctt tgtttgctga   3840
atgagttgat gtaagtttaa taagggtga gataatgttt aacttgcatg gcgtgttaaa    3900
tggggcgggg cttaaagggt atataatgcg ccgtgggcta atcttggtta catctgacct   3960
catgagggct gggagtgtt tggaagattt ttctgctgtg cgtaacttgc tggaacagag     4020
ctctaacagt acctcttggt tttggaggtt tctgtggggc tcatcccagg caaagttagt   4080
ctgcagaatt aaggaggatt acaagtggga atttgaagag cttttgaaat cctgtggtga   4140
gctgtttgat tctttgaatc tgggtcacca ggcgcttttc caagagaagg tcatcaagac   4200
tttggatttt tccacaccgg ggcgcgctgc ggctgctgtt gctttttga gttttataaa     4260 ggataaatgg agcgaagaaa cccatctgag cgggggtac ctgctggatt ttctggccat     4320
gcatctgtgg agagcggttg tgagacacaa gaatcgcctg ctactgttgt cttccgtccg   4380
cccggcgata ataccgacgg aggagcagca gcagcagcag gaggaagcca ggcggcggcg   4440
gcaggagcag agcccatgga acccgagagc cggcctggac cctcgggaat gaatgttgta   4500
caggtggctg aactgtatcc agaactgaga cgcattttga caattacaga ggatgggcag   4560
gggctaaagg gggtaaagag ggagcggggg gcttgtgagg ctacagagga ggctaggaat   4620
ctagctttta gcttaatgac cagacaccgt cctgagtgta ttacttttca acagatcaag   4680
gataattgcg ctaatgagct tgatctgctg gcgcagaagt attccataga gcagctgacc   4740
acttactggc tgcagccagg ggatgatttt gaggaggcta ttagggtata tgcaaaggtg   4800
gcacttaggc cagattgcaa gtacaagatc agcaaacttg taaatatcag gaattgttgc   4860
tacatttctg ggaacggggc cgaggtggag atagatacgg aggataggt ggcctttaga    4920 tgtagcatga taaatatgtg gccgggggtg cttggcatgg acggggtggt tattatgaat   4980
gtaaggttta ctggccccaa ttttagcggt acggttttcc tggccaatac caaccttatc   5040
ctacacggtg taagcttcta tgggtttaac aatacctgtg tggaagcctg gaccgatgta   5100
agggttcggg gctgtgcctt ttactgctgc tggaagggggg tggtgtgtcg ccccaaaagc   5160
```

| | |
|---|---|
| agggcttcaa ttaagaaatg cctctttgaa aggtgtacct tgggtatcct gtctgagggt | 5220 |
| aactccaggg tgcgccacaa tgtggcctcc gactgtggtt gcttcatgct agtgaaaagc | 5280 |
| gtggctgtga ttaagcataa catggtatgt ggcaactgcg aggacagggc ctctcagatg | 5340 |
| ctgacctgct cggacggcaa ctgtcacctg ctgaagacca ttcacgtagc cagccactct | 5400 |
| cgcaaggcct ggccagtgtt tgagcataac atactgaccc gctgttcctt gcatttgggt | 5460 |
| aacaggaggg gggtgttcct accttaccaa tgcaatttga gtcacactaa gatattgctt | 5520 |
| gagcccgaga gcatgtccaa ggtgaacctg aacggggtgt ttgacatgac catgaagatc | 5580 |
| tggaaggtgc tgaggtacga tgagacccgc accaggtgca gaccctgcga gtgtggcggt | 5640 |
| aaacatatta ggaaccagcc tgtgatgctg gatgtgaccg aggagctgag gcccgatcac | 5700 |
| ttggtgctgg cctgcacccg cgctgagttt ggctctagcg atgaagatac agattgacat | 5760 |
| atgcaggtac ggggcctccg cctccggcac gggcagggct gccttagtct cccctccgga | 5820 |
| cacgtgggtc tgtggtcatt ctctgtggct gaggccgagt ctcacggtgt ctcccttttca | 5880 |
| aactgctcac acccgtcttg tgtttttgtc tctggcacag aattgcccgt ttccatacag | 5940 |
| ggtctcttcc ttcggtcttt tgtattttg attgttatgt aaaactcgct tttattttaa | 6000 |
| tattgatgtc agtatttcaa ctgctgtaaa attataaact tttatacttg ggtaagtccc | 6060 |
| ccaggggcga gttcctcgct ctgggatgca ggcatgcttc tcaccgtgca gagctgcact | 6120 |
| tggcctcagc tggctgtatg gaaatgcacc ctccctcctg ccgctcctct ctagaacctt | 6180 |
| ctagaacctg gctgtgctg cttttgagcc tcagacccca gggcagcatc tcggttctgc | 6240 |
| gccacttcct ttgtgtttat atggcgtttt gtctgtgttg ctgtttagag taaataaact | 6300 |
| gtttatataa aggttttggt tgcattatta tcattgaaag tgagaggagg cggcctccca | 6360 |
| gtgcccggcc ctccccaccc acctgcagcc caccgcgga tccactagtt ctagagcggc | 6420 |
| cgccaccgcg gtggagctcc aattcgccct atagtgagtc gtattacgcg cgctcactgg | 6480 |
| ccgtcgtttt acaacgtcgt gactgggaaa accctggcgt tacccaactt aatcgccttg | 6540 |
| cagcacatcc cccttttcgcc agctggcgta atagcgaaga ggcccgcacc gatcgccctt | 6600 |
| cccaacagtt gcgcagcctg aatggcgaat gggacgcgcc ctgtagcggc gcattaagcg | 6660 |
| cggcgggtgt ggtggttacg cgcagcgtga ccgctacact tgccagcgcc ctagcgcccg | 6720 |
| ctcctttcgc tttcttccct tcctttctcg ccacgttcgc cggctttccc cgtcaagctc | 6780 |
| taaatcgggg gctcccttta gggttccgat ttagtgcttt acggcacctc gaccccaaaa | 6840 |
| aacttgatta gggtgatggt tcacgtagtg gccatcgcc ctgatagacg ttttcgcc | 6900 |
| ctttgacgtt ggagtccacg ttctttaata gtggactctt gttccaaact ggaacaacac | 6960 |
| tcaaccctat ctcggtctat tcttttgatt tataagggat tttgccgatt tcggcctatt | 7020 |
| ggttaaaaaa tgagctgatt taacaaaaat ttaacgcgaa ttttaacaaa atattaacgc | 7080 |
| ttacaattta g | 7091 |

<210> SEQ ID NO 23
<211> LENGTH: 10706
<212> TYPE: DNA
<213> ORGANISM: artificial
<220> FEATURE:
<223> OTHER INFORMATION: synthetic

<400> SEQUENCE: 23

| | |
|---|---|
| ctcgagttta ctccctatca gtgatagaga acgtatgtcg agtttactcc ctatcagtga | 60 |
| tagagaacga tgtcgagttt actccctatc agtgatagag aacgtatgtc gagtttactc | 120 |

```
cctatcagtg atagagaacg tatgtcgagt ttactcccta tcagtgatag agaacgtatg    180
tcgagtttat ccctatcagt gatagagaac gtatgtcgag tttactccct atcagtgata    240
gagaacgtat gtcgaggtag gcgtgtacgg tgggaggcct atataagcag agctcgttta    300
gtgaaccgtc agatcgcctg gagaattcga gctcggtacc catcgagtgc cagcgagtag    360
agttttctcc tccgagccgc tccgacaccg ggactgaaaa tgagacatat tatctgccac    420
ggaggtgtta ttaccgaaga aatggccgcc agtcttttgg accagctgat cgaagaggta    480
ctggctgata atcttccacc tcctagccat tttgaaccac ctacccttca cgaactgtat    540
gatttagacg tgacggcccc cgaagatccc aacgaggagg cggtttcgca gattttccc     600 gactctgtaa tgttggcggt gcaggaaggg attgacttac tcacttttcc gccggcgccc    660
ggttctccgg agccgcctca cctttccgg cagcccgagc agccggagca gagagccttg    720
ggtccggttt ctatgccaaa ccttgtaccg gaggtgatcg atcttacctg ccacgaggct    780
ggctttccac ccagtgacga cgaggatgaa gagggtgagg agtttgtgtt agattatgtg    840
gagcaccccg ggcacggttg caggtcttgt cattatcacc ggaggaatac ggggaccca     900 gatattatgt gttcgctttg ctatatgagg acctgtggca tgtttgtcta cagtaagtga    960
aaattatggg cagtgggtga tagagtggtg ggtttggtgt ggtaattttt tttttaattt   1020
ttacagtttt gtggtttaaa gaattttgta ttgtgatttt tttaaaaggt cctgtgtctg   1080
aacctgagcc tgagcccgag ccagaaccgg agcctgcaag acctaccgc cgtcctaaaa    1140 tggcgcctgc tatcctgaga cgcccgacat cacctgtgtc tagagaatgc aatagtagta   1200
cggatagctg tgactccggt ccttctaaca cacctcctga gatacacccg gtggtccgc    1260 tgtgccccat taaaccagtt gccgtgagag ttggtgggcg tcgccaggct gtggaatgta   1320
tcgaggactt gcttaacgag cctgggcaac ctttggactt gagctgtaaa cgccccaggc   1380
cataaggtgt aaacctgtga ttgcgtgtgt ggttaacgcc tttgtttgct gaatgagttg   1440
atgtaagttt aataaagggt gagataatgt ttaacttgca tggcgtgtta aatggggcgg   1500
ggcttaaagg gtatataatg cgccgtgggc taatcttggt tacatctgac ctcatggagg   1560
cttgggagtg tttggaagat ttttctgctg tgcgtaactt gctggaacag agctctaaca   1620
gtacctcttg gttttggagg tttctgtggg gctcatccca ggcaaagtta gtctgcagaa   1680
ttaaggagga ttacaagtgg gaatttgaag agcttttgaa atcctgtggt gagctgtttg   1740
attctttgaa tctgggtcac caggcgcttt tccaagagaa ggtcatcaag actttggatt   1800
tttccacacc ggggcgcgct gcggctgctg ttgctttttt gagttttata aaggataaat   1860
ggagcgaaga aacccatctg agcgggggt accctgctgga ttttctggcc atgcatctgt   1920
ggagagcggt tgtgagacac aagaatcgcc tgctactgtt gtcttccgtc cgcccggcga   1980
taataccgac ggaggagcag cagcagcagc aggaggaagc caggcggcgg cggcaggagc   2040
agagcccatg gaacccgaga gccggcctgg accctcggga tgaatgttg tacaggtggc   2100 tgaactgtat ccagaactga gacgcatttt gacaattaca gaggatgggc aggggctaaa   2160
gggggtaaag agggagcggg gggcttgtga ggctacagag gaggctagga atctagcttt   2220
tagcttaatg accagacacc gtcctgagtg tattactttt caacagatca aggataattg   2280
cgctaatgag cttgatctgc tggcgcagaa gtattccata gagcagctga ccacttactg   2340
gctgcagcca ggggatgatt ttgaggaggc tattagggta tatgcaaagg tggcacttag   2400
gccagattgc aagtacaaga tcagcaaact tgtaaatatc aggaattgtt gctacatttc   2460
```

| | | | | |
|---|---|---|---|---|
| tgggaacggg | gccgaggtgg | agatagatac | ggaggatagg | gtggcccttta datgtagcat | 2520 |
| gataaatatg | tggccggggg | tgcttggcat | ggacggggtg | gttattatga atgtaaggtt | 2580 |
| tactggcccc | aattttagcg | gtacggtttt | cctggccaat | accaaccta tcctacacgg | 2640 |
| tgtaagcttc | tatgggttta | acaataacctg | tgtggaagcc | tggaccgatg taagggttcg | 2700 |
| gggctgtgcc | ttttactgct | gctggaaggg | ggtggtgtgt | cgccccaaaa gcagggcttc | 2760 |
| aattaagaaa | tgcctctttg | aaaggtgtac | cttgggtatc | ctgtctgagg gtaactccag | 2820 |
| ggtgcgccac | aatgtggcct | ccgactgtgg | ttgcttcatg | ctagtgaaaa gcgtggctgt | 2880 |
| gattaagcat | aacatggtat | gtggcaactg | cgaggacagg | gcctctcaga tgctgacctg | 2940 |
| ctcggacggc | aactgtcacc | tgctgaagac | cattcacgta | gccagccact ctcgcaaggc | 3000 |
| ctggccagtg | tttgagcata | acatactgac | ccgctgttcc | ttgcatttgg gtaacaggag | 3060 |
| gggggtgttc | ctaccttacc | aatgcaattt | gagtcacact | aagatattgc ttgagcccga | 3120 |
| gagcatgtcc | aaggtgaacc | tgaacggggt | gtttgacatg | accatgaaga tctggaaggt | 3180 |
| gctgaggtac | gatgagaccc | gcaccaggtg | cagaccctgc | gagtgtggcg gtaaacatat | 3240 |
| taggaaccag | cctgtgatgc | tggatgtgac | cgaggagctg | aggcccgatc acttggtgct | 3300 |
| ggcctgcacc | cgcgctgagt | ttggctctag | cgatgaagat | acagattgac atatgcaggt | 3360 |
| acggggcctc | cgcctccggc | acgggcaggg | ctgccttagt | ctcccctccg gacacgtggg | 3420 |
| tctgtggtca | ttctctgtgg | ctgaggccga | gtctcacggt | gtctcccttt caaactgctc | 3480 |
| acaccgtctc | tgtgtttttg | tctctggcac | agaaccctcc | cccaccttga attgcccgtt | 3540 |
| tccatacagg | gtctcttcct | tcggtctttt | gtattttga | ttgttatgta aaactcgctt | 3600 |
| ttatttaat | attgatgtca | gtatttcaac | tgctgtaaaa | ttataaactt ttatacttgg | 3660 |
| gtaagtcccc | caggggcgag | ttcctcgctc | tgggatgcag | gcatgcttct caccgtgcag | 3720 |
| agctgcactt | ggcctcagct | ggctgtatgg | aaatgcaccc | tccctcctgc cgctcctctc | 3780 |
| tagaaccttc | tagaacctgg | gctgtgctgc | ttttgagcct | cagacccag ggcagcatct | 3840 |
| cggttctgcg | ccacttcctt | tgtgtttata | tggcgttttg | tctgtgttgc tgtttagagt | 3900 |
| aaaataaactg | tttatataaa | ggttttggtt | gcattattat | cattgaaagt gagaggaggc | 3960 |
| ggcctcccag | tgcccggccc | tccccacccca | cctgcagccc | caccgcggat ccagacatga | 4020 |
| taagatacat | tgatgagttt | ggacaaacca | caactagaat | gcagtgaaaaa aaatgctttta | 4080 |
| tttgtgaaat | ttgtgatgct | attgctttat | ttgtaaccat | tataagctgc aataaacaag | 4140 |
| ttaacaacaa | caattgcatt | cattttatgt | ttcaggttca | ggggggaggtg tgggaggttt | 4200 |
| tttaaagcaa | gtaaaacctc | tacaaatgtg | gtatggctga | ttatgatctc tagtcaaggc | 4260 |
| actatacatc | aaatattcct | tattaaccccc | tttacaaatt | aaaaagctaa aggtacacaa | 4320 |
| tttttgagca | tagttattaa | tagcagacac | tctatgcctg | tgtggagtaa gaaaaaacag | 4380 |
| tatgttatga | ttataactgt | tatgcctact | tataaaggtt | acagaatatt tttccataat | 4440 |
| tttcttgtat | agcagtgcag | cttttttcctt | tgtggtgtaa atagcaaagc aagcaagagt | 4500 |
| tctattacta | aacacagcat | gactcaaaaa | acttagcaat | tctgaaggaa agtccttggg | 4560 |
| gtcttctacc | tttctcttct | ttttttggagg | agtagaatgt | tgagtcag cagtagcctc | 4620 |
| atcatcacta | gatggcattt | cttctgagca | aaacaggttt | tcctcattaa aggcattcca | 4680 |
| ccactgctcc | cattcatcag | ttccataggt | tggaatctaa | aatacacaaa caattagaat | 4740 |
| cagtagttta | acacattata | cacttaaaaa | tttttatattt | accttagagc tttaaatctc | 4800 |
| tgtaggtagt | ttgtccaatt | atgtcacacc | acagaagtaa | ggttccttca caaagatccg | 4860 |

```
ggaccaaagc ggccatcgtg cctccccact cctgcagttc gggggcatgg atgcgcggat    4920
agccgctgct ggtttcctgg atgccgacgg atttgcactg ccggtagaac tccgcgaggt    4980
cgtccagcct caggcagcag ctgaaccaac tcgcgagggg atcgagcccg ggtgggcga     5040 agaactccag catgagatcc ccgcgctgga ggatcatcca gccggcgtcc cggaaaacga    5100
ttccgaagcc caacctttca tagaaggcgg cggtggaatc gaaatctcgt gatggcaggt    5160
tgggcgtcgc ttggtcggtc atttcgaacc ccagagtccc gctcagaaga actcgtcaag    5220
aaggcgatag aaggcgatgc gctgcgaatc gggagcggcg ataccgtaaa gcacgaggaa    5280
gcggtcagcc cattcgccgc caagctcttc agcaatatca cgggtagcca acgctatgtc    5340
ctgatagcgg tccgccacac ccagccggcc acagtcgatg aatccagaaa agcggccatt    5400
ttccaccatg atattcggca agcaggcatc gccatgggtc acgacgagat cctcgccgtc    5460
gggcatgcgc gccttgagcc tggcgaacag ttcggctggc gcgagcccct gatgctcttc    5520
gtccagatca tcctgatcga caagaccggc ttccatccga gtacgtgctc gctcgatgcg    5580
atgtttcgct tggtggtcga atgggcaggt agccggatca agcgtatgca gccgccgcat    5640
tgcatcagcc atgatggata ctttctcggc aggagcaagg tgagatgaca ggagatcctg    5700
ccccggcact cgcccaata gcagccagtc ccttcccgct tcagtgacaa cgtcgagcac    5760
agctgcgcaa ggaacgcccg tcgtggccag ccacgatagc cgcgctgcct cgtcctgcag    5820
ttcattcagg gcaccggaca ggtcggtctt gacaaaaaga accgggcgcc cctgcgctga    5880
cagccggaac acggcggcat cagagcagcc gattgtctgt tgtgcccagt catagccgaa    5940
tagcctctcc acccaagcgg ccggagaacc tgcgtgcaat ccatcttgtt caatcatgcg    6000
aaacgatcct catcctgtct cttgatcaga tcttgatccc ctgcgccatc agatccttgg    6060
cggcaagaaa gccatccagt ttactttgca gggcttccca accttaccag agggcgcccc    6120
agctggcaat tccggttcgc ttgctgtcca taaaaccgcc cagtctagct atcgccatgt    6180
aagcccactg caagctacct gctttctctt tgcgcttgcg ttttcccttg tccagatagc    6240
ccagtagctg acattcatcc ggggtcagca ccgtttctgc ggactggctt tctacgtgtt    6300
ccgcttcctt tagcagccct tgcgccctga gtgcttgcgg cagcgtgttg ctagcttttt    6360
gcaaaagcct aggcctccaa aaaagcctcc tcactacttc tggaatagct cagaggccga    6420
ggcggcctcg gcctctgcat aaataaaaaa aattagtcag ccatggggcg gagaatgggc    6480
ggaactgggc ggagttaggg gcgggatggg cggagttagg ggcgggacta tggttgctga    6540
ctaattgaga tgcatgcttt gcatacttct gcctgctggg gagcctgggg actttccaca    6600
cctggttgct gactaattga gatgcatgct ttgcatactt ctgcctgctg gggagcctgg    6660
ggactttcca caccctaact gacacacatt ccacagctgc ctcgcgcgtt tcggtgatga    6720
cggtgaaaac ctctgacaca tgcagctccc ggagacggtc acagcttgtc tgtaagcgga    6780
tgccgggagc agacaagccc gtcagggcgc gtcagcgggt gttggcgggt gtcggggcgc    6840
agccatgacc cagtcacgta gcgatagcgg agtgtatact ggcttaacta tgcggcatca    6900
gagcagattg tactgagagt gcaccacctc gaggagcttg gcccattgca tacgttgtat    6960
ccatatcata atatgtacat ttatattggc tcatgtccaa cattaccgcc atgttgacat    7020
tgattattga ctagttatta atagtaatca attacggggt cattagttca tagcccatat    7080
atggagttcc gcgttacata acttacggta aatggcccgc ctggctgacc gcccaacgac    7140
ccccgcccat tgacgtcaat aatgacgtat gttcccatag taacgccaat agggactttc    7200
```

```
cattgacgtc aatgggtgga gtatttacgc taaactgccc acttggcagt acatcaagtg    7260
tatcatatgc caagtacgcc ccctattgac gtcaatgacg gtaaatggcc cgcctggcat    7320
tatgcccagt acatgacctt atgggacttt cctacttggc agtacatcta cgtattagtc    7380
atcgctatta ccatggtgat gcggttttgg cagtacatca atgggcgtgg atagcggttt    7440
gactcacggg gatttccaag tctccacccc attgacgtca atgggagttt gttttggcac    7500
caaaatcaac gggactttcc aaaatgtcgt aacaactccg ccccattgac gcaaatgggc    7560
ggtaggcgtg tacggtggga ggtctatata agcagagctc gtttagtgaa ccgtcagatc    7620
gcctggagac gccatccacg ctgttttgac ctccatagaa gacaccggga ccgatccagc    7680
ctccgcggcc ccgaattcac catgtctaga ctggacaaga gcaaagtcat aaacggcgct    7740
ctggaattac tcaatggagt cggtatcgaa ggcctgacga caaggaaact cgctcaaaag    7800
ctgggagttg agcagcctac cctgtactgg cacgtgaaga caagcgggc cctgctcgat    7860 gccctgccaa tcgagatgct ggacaggcat catacccact tctgcccct ggaaggcgag    7920 tcatggcaag actttctgcg gaacaacgcc aagtcattcc gctgtgctct cctctcacat    7980
cgcgacgggg ctaaagtgca tctcggcacc cgcccaacag agaaacagta cgaaaccctg    8040
gaaaatcagc tcgcgttcct gtgtcagcaa ggcttctccc tggagaacgc actgtacgct    8100
ctgtccgccg tgggccactt tacactgggc tgcgtattgg aggaacagga gcatcaagta    8160 gcaaagagg aaagagagac acctaccacc gattctatgc ccccacttct gagacaagca    8220
attgagctgt cgaccggca gggagccgaa cctgccttcc ttttcggcct ggaactaatc    8280
atatgtggcc tggagaaaca gctaaagtgc gaaagcggcg gccggccga cgcccttgac    8340 gattttgact tagacatgct cccagccgat gcccttgacg actttgacct tgatatgctg    8400
cctgctgacg ctcttgacga ttttgacctt gacatgctcc ccgggtaact aagtaaggat    8460
ccactagttc tagagcggcc gcatcgataa gcttgtcgac gatatctcta gaggatcata    8520
atcagccata ccacatttgt agaggtttta cttgctttaa aaaacctccc acacctcccc    8580
ctgaacctga acataaaat gaatgcaatt gttgttgtta acttgtttat tgcagcttat    8640
aatggttaca aataaagcaa tagcatcaca aatttcacaa ataaagcatt ttttcactg    8700 cctcgagctt cctcgctcac tgactcgctg cgctcggtcg ttcggctgcg gcgagcggta    8760
tcagctcact caaaggcggt aatacggtta tccacagaat cagggggataa cgcaggaaag    8820 aacatgtgag caaaaggcca gcaaaaggcc aggaaccgta aaaaggccgc gttgctggcg    8880 ttttccata ggctccgccc ccctgacgag catcacaaaa atcgacgctc aagtcagagg    8940
tggcgaaacc cgacaggact ataaagatac caggcgtttc cccctggaag ctccctcgtg    9000
cgctctcctg ttccgaccct gccgcttacc ggatacctgt ccgcctttct cccttcggga    9060
agcgtggcgc tttctcatag ctcacgctgt aggtatctca gttcggtgta ggtcgttcgc    9120
tccaagctgg gctgtgtgca cgaacccccc gttcagcccg accgctgcgc cttatccggt    9180
aactatcgtc ttgagtccaa cccggtaaga cacgacttat cgccactggc agcagccact    9240
ggtaacagga ttagcagagc gaggtatgta ggcggtgcta cagagttctt gaagtggtgg    9300
cctaactacg gctacactag aagaacagta tttggtatct gcgctctgct gaagccagtt    9360
accttcggaa aaagagttgg tagctcttga tccggcaaac aaaccaccgc tggtagcggt    9420 ggttttttg tttgcaagca gcagattacg cgcagaaaaa aaggatctca agaagatcct    9480
ttgatctttt ctacggggtc tgacgctcag tggaacgaaa actcacgtta agggattttg    9540
gtcatgagat tatcaaaaag gatcttcacc tagatccttt taaattaaaa atgaagtttt    9600
```

| | | | | | |
|---|---|---|---|---|---|
| aaatcaatct | aaagtatata | tgagtaaact | tggtctgaca | gttaccaatg | cttaatcagt | 9660
| gaggcaccta | tctcagcgat | ctgtctattt | cgttcatcca | tagttgcctg | actcccgtc | 9720
| gtgtagataa | ctacgatacg | ggagggctta | ccatctggcc | ccagtgctgc | aatgataccg | 9780
| cgagacccac | gctcaccggc | tccagattta | tcagcaataa | accagccagc | cggaagggcc | 9840
| gagcgcagaa | gtggtcctgc | aactttatcc | gcctccatcc | agtctattaa | ttgttgccgg | 9900
| gaagctagag | taagtagttc | gccagttaat | agtttgcgca | acgttgttgc | cattgctaca | 9960
| ggcatcgtgg | tgtcacgctc | gtcgtttggt | atggcttcat | tcagctccgg | ttcccaacga | 10020
| tcaaggcgag | ttacatgatc | ccccatgttg | tgcaaaaaag | cggttagctc | cttcggtcct | 10080
| ccgatcgttg | tcagaagtaa | gttggccgca | gtgttatcac | tcatggttat | ggcagcactg | 10140
| cataattctc | ttactgtcat | gccatccgta | agatgctttt | ctgtgactgg | tgagtactca | 10200
| accaagtcat | tctgagaata | gtgtatgcgg | cgaccgagtt | gctcttgccc | ggcgtcaaca | 10260
| cgggataata | ccgcgccaca | tagcagaact | ttaaaagtgc | tcatcattgg | aaaacgttct | 10320
| tcggggcgaa | aactctcaag | gatcttaccg | ctgttgagat | ccagttcgat | gtaacccact | 10380
| cgtgcaccca | actgatcttc | agcatctttt | actttcacca | gcgtttctgg | gtgagcaaaa | 10440
| acaggaaggc | aaaatgccgc | aaaaaaggga | ataagggcga | cacggaaatg | ttgaatactc | 10500
| atactcttcc | tttttcaata | ttattgaagc | atttatcagg | gttattgtct | catgagcgga | 10560
| tacatatttg | aatgtattta | gaaaaataaa | caaatagggg | ttccgcgcac | atttccccga | 10620
| aaagtgccac | ctgacgtcta | agaaaccatt | attatcatga | cattaaccta | taaaaatagg | 10680
| cgtatcacga | ggccctttcg | tcttca | | | | 10706

<210> SEQ ID NO 24
<211> LENGTH: 7229
<212> TYPE: DNA
<213> ORGANISM: artificial
<220> FEATURE:
<223> OTHER INFORMATION: synthetic

<400> SEQUENCE: 24

| | | | | | |
|---|---|---|---|---|---|
| gtggcacttt | tcggggaaat | gtgcgcggaa | cccctatttg | tttatttttc | taaatacatt | 60
| caaatatgta | tccgctcatg | agacaataac | cctgataaat | gcttcaataa | tattgaaaaa | 120
| ggaagagtat | gagtattcaa | catttccgtg | tcgcccttat | tcccttttt | gcggcatttt | 180
| gccttcctgt | ttttgctcac | ccagaaacgc | tggtgaaagt | aaaagatgct | gaagatcagt | 240
| tgggtgcacg | agtgggttac | atcgaactgg | atctcaacag | cggtaagatc | cttgagagtt | 300
| ttcgccccga | agaacgtttt | ccaatgatga | gcacttttaa | agttctgcta | tgtggcgcgg | 360
| tattatcccg | tattgacgcc | gggcaagagc | aactcggtcg | ccgcatacac | tattctcaga | 420
| atgacttggt | tgagtactca | ccagtcacag | aaaagcatct | tacggatggc | atgacagtaa | 480
| gagaattatg | cagtgctgcc | ataaccatga | gtgataacac | tgcggccaac | ttacttctga | 540
| caacgatcgg | aggaccgaag | gagctaaccg | cttttttgca | caacatgggg | gatcatgtaa | 600
| ctcgccttga | tcgttgggaa | ccggagctga | atgaagccat | accaaacgac | gagcgtgaca | 660
| ccacgatgcc | tgtagcaatg | gcaacaacgt | tgcgcaaact | attaactggc | gaactactta | 720
| ctctagcttc | ccggcaacaa | ttaatagact | ggatggaggc | ggataaagtt | gcaggaccac | 780
| ttctgcgctc | ggcccttccg | gctggctggt | ttattgctga | taaatctgga | gccggtgagc | 840
| gtgggtctcg | cggtatcatt | gcagcactgg | ggccagatgg | taagccctcc | cgtatcgtag | 900

```
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc cttttttgata  1080
atctcatgac caaaatccct taacgtgagt tttcgttcca ctgagcgtca gaccccgtag   1140
aaaagatcaa aggatcttct tgagatcctt ttttttctgcg cgtaatctgc tgcttgcaaa  1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag cgcagcggt cgggctgaac ggggggttcg tgcacacagc   1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatgaaaaaa cgccagcaac gcggcctttt tacggttcct ggccttttgc tggccttttg  1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
tgtgtggaat tgtgagcgga taacaatttc acacaggaaa cagctatgac catgattacg  2160
ccaagcgcgc aattaaccct cactaaaggg aacaaaagct gggtaccggg ccccccctcg  2220
aggtcatcga attctaccgg gtaggggagg cgcttttccc aaggcagtct ggagcatgcg  2280
ctttagcagc cccgctggca cttggcgcta cacaagtggc ctctggcctc gcacacattc  2340
cacatccacc ggtaggcgcc aaccggctcc gttctttggt ggccccttcg cgccaccttc  2400
tactcctccc ctagtcagga agttcccccc cgccccgcag ctcgcgtcgt gcaggacgtg  2460
acaaatggaa gtagcacgtc tcactagtct cgtgcagatg gacagcaccg ctgagcaatg  2520
gaagcgggta ggcctttggg gcagcggcca atagcagctt tgctccttcg ctttctgggc  2580
tcagaggctg ggaaggggtg ggtccggggg cgggctcagg ggcgggctca ggggcggggc  2640
gggcgcccga aggtcctccg gaggcccggc attctcgcac gcttcaaaag cgcacgtctg  2700
ccgcgctgtt ctcctcttcc tcatctccgg gcctttcgac cagcttgata tcgagtgcca  2760
gcgagtagag ttttctcctc cgagccgctc cgacaccggg actgaaaatg agacatatta  2820
tctgccacgg aggtgttatt accgaagaaa tggccgccag tcttttggac cagctgatcg  2880
aagaggtact ggctgataat cttccacctc ctagccattt tgaaccacct acccttcacg  2940
aactgtatga tttagacgtg acggcccccg aagatcccaa cgaggaggcg gtttcgcaga  3000
ttttttcccga ctctgtaatg ttggcggtgc aggaagggat tgacttactc acttttccgc 3060
cggcgcccgg ttctccggag ccgcctcacc tttcccggca gcccgagcag ccggagcaga  3120
gagccttggg tccggtttct atgccaaacc ttgtaccgga ggtgatcgat cttacctgcc  3180
acgaggctga ctttccaccc agtgacgacg aggatgaaga gggtgaggag tttgtgttag  3240
attatgtgga gcaccccggg cacggttgca ggtcttgtca ttatcaccgg aggaatacgg  3300
```

```
gggacccaga tattatgtgt tcgctttgct atatgaggac ctgtggcatg tttgtctaca    3360
gtaagtgaaa attatgggca gtgggtgata gagtggtggg tttggtgtgg taatttttt     3420 tttaatttt  acagttttgt ggtttaaaga attttgtatt gtgattttt  taaaaggtcc    3480 tgtgtctgaa cctgagcctg agcccgagcc agaaccggag cctgcaagac ctacccgccg    3540
tcctaaaatg gcgcctgcta tcctgagacg cccgacatca cctgtgtcta gagaatgcaa    3600
tagtagtacg gatagctgtg actccggtcc ttcaacaca  cctcctgaga tacacccggt    3660
ggtcccgctg tgccccatta aaccagttgc cgtgagagtt ggtgggcgtc gccaggctgt    3720
ggaatgtatc gaggacttgc ttaacgagcc tgggcaacct ttggacttga gctgtaaacg    3780
ccccaggcca taaggtgtaa acctgtgatt gcgtgtgtgg ttaacgcctt tgtttgctga    3840
atgagttgat gtaagtttaa taagggtga  gataatgttt aacttgcatg gcgtgttaaa    3900
tggggcgggg cttaaagggt atataatgcg ccgtgggcta atcttggtta catctgacct    3960
catggaggct tgggagtgtt tggaagattt ttctgctgtg cgtaacttgc tggaacagag    4020
ctctaacagt acctcttggt tttggaggtt tctgtggggc tcatcccagg caaagttagt    4080
ctgcagaatt aaggaggatt acaagtggga atttgaagag cttttgaaat cctgtggtga    4140
gctgtttgat tctttgaatc tgggtcacca ggcgcttttc caagagaagg tcatcaagac    4200
tttggatttt tccacaccgg ggcgcgctgc ggctgctgtt gcttttttga gtttataaa     4260 ggataaatgg agcgaagaaa cccatctgag cgggggtac  ctgctggatt ttctggccat    4320
gcatctgtgg agagcggttg tgagacacaa gaatcgcctg ctactgttgt cttccgtccg    4380
cccggcgata ataccgacgg aggagcagca gcagcagcag gaggaagcca ggcggcggcg    4440
gcaggagcag agcccatgga acccgagagc cggcctggac cctcgggaat gaatgttgta    4500
caggtggctg aactgtatcc agaactgaga cgcatttga  caattacaga ggatgggcag    4560
gggctaaagg gggtaaagag ggagcggggg gcttgtgagg ctacagagga ggctaggaat    4620
ctagctttta gcttaatgac cagacaccgt cctgagtgta ttacttttca acagatcaag    4680
gataattgcg ctaatgagct tgatctgctg gcgcagaagt attccataga gcagctgacc    4740
acttactggc tgcagccagg ggatgatttt gaggaggcta ttagggtata tgcaaaggtg    4800
gcacttaggc cagattgcaa gtacaagatc agcaaacttg taaatatcag gaattgttgc    4860
tacatttctg ggaacgggc  cgaggtggag atagatacgg aggatagggt ggcctttaga    4920
tgtagcatga taaatatgtg gccgggggtg cttggcatgg acggggtggt tattatgaat    4980
gtaaggttta ctggccccaa ttttagcggt acggttttcc tggccaatac caaccttatc    5040
ctacacggtg taagcttcta tgggtttaac aatacctgtg tggaagcctg gaccgatgta    5100
agggttcggg gctgtgcctt ttactgctgc tggaagggg  tggtgtgtcg ccccaaaagc    5160
agggcttcaa ttaagaaatg cctctttgaa aggtgtacct tgggtatcct gtctgagggt    5220
aactccaggt tgcgccacaa tgtggcctcc gactgtggtt gcttcatgct agtgaaaagc    5280
gtggctgtga ttaagcataa catggtatgt ggcaactgcg aggacagggc ctctcagatg    5340
ctgacctgct cggacggcaa ctgtcacctg ctgaagacca ttcacgtagc cagccactct    5400
cgcaaggcct ggccagtgtt tgagcataac atactgaccc gctgttcctt gcatttgggt    5460
aacaggaggg gggtgttcct accttaccaa tgcaatttga gtcacactaa gatattgctt    5520
gagcccgaga gcatgtccaa ggtgaacctg aacggggtgt ttgacatgac catgaagatc    5580
tggaaggtgc tgaggtacga tgagacccgc accaggtgca gaccctgcga gtgtggcggt    5640
```

```
aaacatatta ggaaccagcc tgtgatgctg gatgtgaccg aggagctgag gcccgatcac      5700
ttggtgctgg cctgcacccg cgctgagttt ggctctagcg atgaagatac agattgaggt      5760
actgaaatgg aattcaattt ttaagtgtat aatgtgttaa actactgatt ctaattgttt      5820
gtgtatttta gattccaacc tatggaactg atgaatggga gcagtggtgg aatgccctta      5880
atgaggaaaa cctgttttgc tcagaagaaa tgccatctag tgatgatgag gctactgctg      5940
actctcaaca ttctactcct ccaaaaaaga agagaaaggt agaagacccc aaggactttc      6000
cttcagaatt gctaagtttt ttgagtcatg ctgtgtttag taatagaact cttgcttgct      6060
ttgctattta caccacaaag gaaaaagctg cactgctata caagaaaatt atggaaaaat      6120
attctgtaac ctttataagt aggcataaca gttataatca taacatactg ttttttctta      6180
ctccacacag gcatagagtg tctgctatta ataactatgc tcaaaaattg tgtaccctta      6240 gcttttaat ttgtaaaggg gttaataagg aatatttgat gtatagtgcc ttgactagag      6300
atcataatca gccataccac atttgtagag gttttacttg ctttaaaaaa cctcccacac      6360
ctccccctga acctgaaaca taaatgaat gcaattgttg ttgttaactt gtttattgca      6420
gcttataatg gttacaaata aagcaatagc atcacaaatt tcacaaataa agcattttt      6480 tcactgcatt ctagttgtgg tttgtccaaa ctcatcaatg tatcttatca tgtctggatc      6540
cactagttct agagcggccg ccaccgcggt ggagctccaa ttcgccctat agtgagtcgt      6600
attacgcgcg ctcactggcc gtcgttttac aacgtcgtga ctgggaaaac cctggcgtta      6660
cccaacttaa tcgccttgca gcacatcccc ctttcgccag ctggcgtaat agcgaagagg      6720
cccgcaccga tcgcccttcc caacagttgc gcagcctgaa tggcgaatgg gacgcgccct      6780
gtagcggcgc attaagcgcg gcgggtgtgg tggttacgcg cagcgtgacc gctacacttg      6840
ccagcgccct agcgcccgct cctttcgctt tcttcccttc ctttctcgcc acgttcgccg      6900
gctttccccg tcaagctcta aatcggggc tccctttagg gttccgattt agtgctttac      6960
ggcacctcga ccccaaaaaa cttgattagg gtgatggttc acgtagtggg ccatcgccct      7020
gatagacggt ttttcgccct ttgacgttgg agtccacgtt ctttaatagt ggactcttgt      7080
tccaaactgg aacaacactc aaccctatct cggtctattc ttttgattta agggattt      7140 tgccgatttc ggcctattgg ttaaaaaatg agctgattta acaaaaattt aacgcgaatt      7200
ttaacaaaat attaacgctt acaatttag                                        7229
```

<210> SEQ ID NO 25
<211> LENGTH: 481
<212> TYPE: DNA
<213> ORGANISM: Homo sapiens

<400> SEQUENCE: 25

```
tgaattgccc gttttccatac agggtctctt ccttcggtct tttgtatttt tgattgttat       60
gtaaaactcg cttttatttt aatattgatg tcagtatttc aactgctgta aaattataaa      120
cttttatact tgggtaagtc ccccagggg gagttcctcg ctctgggatg caggcatgct      180
tctcaccgtg cagagctgca cttggcctca gctggctgta tggaaatgca ccctccctcc      240
tgccgctcct ctctagaacc ttctagaacc tgggctgtgc tgcttttgag cctcagaccc      300
cagggcagca tctcggttct gcgccacttc ctttgtgttt atatggcgtt ttgtctgtgt      360
tgctgtttag agtaaataaa ctgtttatat aaaggttttg gttgcattat tatcattgaa      420
agtgagagga ggcggcctcc cagtgcccgg ccctccccac ccacctgcag ccccaccgcg      480
g                                                                      481
```

```
<210> SEQ ID NO 26
<211> LENGTH: 35
<212> TYPE: DNA
<213> ORGANISM: artificial
<220> FEATURE:
<223> OTHER INFORMATION: synthetic

<400> SEQUENCE: 26
gttcagcata tgcaggtacg gggcctccgc ctccg                              35

<210> SEQ ID NO 27
<211> LENGTH: 44
<212> TYPE: DNA
<213> ORGANISM: artificial
<220> FEATURE:
<223> OTHER INFORMATION: synthetic

<400> SEQUENCE: 27
tcaaggtggg ggagggttct gtgccagaga caaaaacaca agac                    44

<210> SEQ ID NO 28
<211> LENGTH: 42
<212> TYPE: DNA
<213> ORGANISM: artificial
<220> FEATURE:
<223> OTHER INFORMATION: synthetic

<400> SEQUENCE: 28
gaaccctccc ccaccttgaa ttgcccgttt ccatacaggg tc                      42

<210> SEQ ID NO 29
<211> LENGTH: 26
<212> TYPE: DNA
<213> ORGANISM: artificial
<220> FEATURE:
<223> OTHER INFORMATION: synthetic

<400> SEQUENCE: 29
ctggatccgc ggtggggctg caggtg                                        26

<210> SEQ ID NO 30
<211> LENGTH: 22
<212> TYPE: DNA
<213> ORGANISM: artificial
<220> FEATURE:
<223> OTHER INFORMATION: synthetic

<400> SEQUENCE: 30
ctgaactgta tccagaactg ag                                            22

<210> SEQ ID NO 31
<211> LENGTH: 21
<212> TYPE: DNA
<213> ORGANISM: artificial
<220> FEATURE:
<223> OTHER INFORMATION: synthetic

<400> SEQUENCE: 31
actgctccca ttcatcagtt c                                             21
```